United States Patent
Bak et al.

(10) Patent No.: US 11,773,409 B2
(45) Date of Patent: Oct. 3, 2023

(54) CRISPR/CAS 9-MEDIATED INTEGRATION OF POLYNUCLEOTIDES BY SEQUENTIAL HOMOLOGOUS RECOMBINATION OF AAV DONOR VECTORS

(71) Applicant: The Board of Trustees of the Leland Stanford Junior University, Stanford, CA (US)

(72) Inventors: Rasmus O. Bak, Risskov (DK); Matthew Porteus, Stanford, CA (US); Sriram Vaidyanathan, Mountain View, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 949 days.

(21) Appl. No.: 16/607,029

(22) PCT Filed: Apr. 23, 2018

(86) PCT No.: PCT/US2018/028957
§ 371 (c)(1),
(2) Date: Oct. 21, 2019

(87) PCT Pub. No.: WO2018/195555
PCT Pub. Date: Oct. 25, 2018

(65) Prior Publication Data
US 2020/0131539 A1    Apr. 30, 2020

Related U.S. Application Data

(60) Provisional application No. 62/488,627, filed on Apr. 21, 2017.

(51) Int. Cl.
*C12N 15/00* (2006.01)
*C12N 15/90* (2006.01)
(Continued)

(52) U.S. Cl.
CPC ........... *C12N 15/902* (2013.01); *A61K 35/76* (2013.01); *C12N 9/22* (2013.01); *C12N 15/86* (2013.01);
(Continued)

(58) Field of Classification Search
None
See application file for complete search history.

(56) References Cited

FOREIGN PATENT DOCUMENTS

WO    WO 2014/152822 A2    9/2014
WO    WO 2014/170480 A1    10/2014
(Continued)

OTHER PUBLICATIONS

Chadwick et al., "Genome Editing for the Study of Cardiovascular Diseases," Curr Cardiol Rep 19(3): 22 (Year: 2017).*
(Continued)

*Primary Examiner* — M Franco G Salvoza
(74) *Attorney, Agent, or Firm* — Morgan, Lewis & Bockius LLP

(57) ABSTRACT

The present invention relates to a system and method for efficiently modifying the genome of cells to treat diseases via sequential homologous recombination using CRISPR/Cas-mediated genome editing with donor DNA delivered by two or more adeno-associated virus (AAV) vectors.

19 Claims, 36 Drawing Sheets

Specification includes a Sequence Listing.

(51) Int. Cl.
    *C12N 9/22* (2006.01)
    *C12N 15/86* (2006.01)
    *C12N 15/861* (2006.01)
    *A61K 35/76* (2015.01)
    *A61K 39/235* (2006.01)
    *A61K 48/00* (2006.01)
    *C07K 14/075* (2006.01)

(52) U.S. Cl.
    CPC ........ *C12N 15/8616* (2013.01); *A61K 39/235* (2013.01); *A61K 48/005* (2013.01); *C07K 14/075* (2013.01); *C12N 15/907* (2013.01); *C12N 2310/20* (2017.05); *C12N 2310/313* (2013.01); *C12N 2710/10043* (2013.01); *C12N 2750/14141* (2013.01); *C12N 2800/40* (2013.01)

(56) References Cited

FOREIGN PATENT DOCUMENTS

| WO | WO 2017/044776 A1 | 3/2017 | |
|---|---|---|---|
| WO | WO-2017044776 A1 * | 3/2017 | ........... C12N 15/111 |

OTHER PUBLICATIONS

Gaj et al., "Genome-Editing Technologies: Principles and Applications," Cold Spring Harb Perspect Biol 8: a023754 (Year: 2016).*

Bak et al., "CRISPR-Mediated Integration of Large Gene Cassettes Using AAV Donor Vectors", Jul. 18, 2017, pp. 750-756, vol. 20, No. 3, *Cell Reports*.

Basiri et al., "The Convenience of Single Homology Arm Donor DNA and CRISPR/Cas9-Nickase for Targeted Insertion of Long DNA Fragment", 2017, pp. 532-539, vol. 18, No. 4. *Cell Journal*.

Chamberlain et al., "Expressing Transgenes That Exceed the Packaging Capacity of Adena-Associated Virus Capsids", Feb. 1, 2016, pp. 1-12, vol. 27, No. 1, *Human Gene Therapy Methods*.

De Ravin et al., "CRISPR-Cas9 gene repair of hematopoietic stem cells from patients with X-linked chronic granulomatous disease", Jan. 11, 2017, pp. 1-10, vol. 9 , No. 372, *Science Translational Medicine*.

Dever et al., "CRISPR/Cas9 β-globin gene targeting in human haematopoietic stem cells", Nov. 7, 2016, pp. 384-389, vol. 539, No. 7629, *Nature*.

Dewitt et al., "Selection-free genome editing of the sickle mutation in human adult hematopoietic stem/progenitor cells", Oct. 12, 2016, pp. 1-20, vol. 8, No. 360, *Science Translational Medicine*.

Gaj et al., "Targeted gene knock-in by homology-directed genome editing using Cas9 ribonucleoprotein and AAV donor delivery", Mar. 2, 2017, pp. e98-e98, vol. 45, No. 11, *Nucleic Acids Research*.

Hendel et al., "Chemically modified guide RNAs enhance CRISPR-Cas genome editing in human primary cells", Jun. 29, 2015, pp. 985-989, vol. 33, No. 9, *Nature Biotechnology*.

Yang et al., "A dual AAV system enables the Cas9-mediated correction of a metabolic liver disease in newborn mice", Mar. 2016, pp. 334-338, vol. 34, No. 3, *Nature biotechnology*.

Yin et al., "Therapeutic genome editing by combined viral and non-viral delivery of CRISPR system components in vivo", Mar. 2016, pp. 328-333, vol. 34, No. 3, *Nature biotechnology*.

* cited by examiner

FIG. 20B

Sequence: CFTRcDNA1.dna (Circular / 7009 bp)
Features: 17 total

| Feature | Location | Size | | | Type |
|---|---|---|---|---|---|
| L-ITR | 1 .. 140 | 140 bp | | ↑ | misc_feature |
| LHA | 165 .. 566 | 402 bp | | ↑ | misc_feature |
| Start | 563 .. 565 | 3 bp | | ↑ | misc_feature |
| PAM | 563 .. 563 | 1 bp | | ↑ | misc_feature |
| sgRNA(mutated) | 564 .. 583 | 20 bp | | ↑ | misc_feature |
| CF-coding sequence first half | 567 .. 3445 | 2879 bp | | ↑ | misc_feature |
| gblock2 | 3322 .. 3445 | 124 bp | | ↑ | misc_feature |
| sgRNA | 3443 .. 3463 | 21 bp | | ↑ | misc_feature |
| CF-1 | 3446 .. 3446 | 1 bp | | ↑ | misc_feature |
| Stuffer | 3464 .. 3863 | 400 bp | | ↑ | misc_feature |
| RHA | 3864 .. 4263 | 400 bp | | ↑ | misc_feature |
| CF-1 | 3864 .. 3880 | 17 bp | | ↑ | misc_feature |
| R-ITR | 4272 .. 4412 | 141 bp | | ↑ | misc_feature |
| f1 origin | 4504 .. 4810 | 307 bp | | ↑ | misc_feature |
| AmpR promoter | 5259 .. 5287 | 29 bp | | ↑ | misc_feature |
| ORF 3 | 5329 .. 6189 | 861 bp | | ↑ | CDS |

/translation = MSIQHFRVALIPFFAAFCLPVFAHPETLVKVKDAEDQLGARVGYIELDLNSGKILESFRPEERFPMMSTFKVLLCGAVLS
RIDAGQEQLGRRIHYSQNDLVEYSPVTEKHLTDGMTVRELCSAATTMSDNTAANLLTTIGGPKELTAFLHNMGDHVTR
LDRWEPELNEAIPNDERDTTMPVAMATTLRKLLTGELLTLASRQQLIDWMEADKVAGPLLRSALPAGWFIADKSGAGE
RGSRGTIAALGPDGKPSRIVVIYTTGSQATMDERNRQIAEIGASLIKHW*    SEQ ID NO:21

286 amino acids = 31.6 kDa

| pBR322 origin | 6344 .. 6963 | 620 bp | | ↑ | misc_feature |

FIG. 21B

Sequence: CFTRcDNA2.dna (Circular / 7183 bp)
Features: 16 total

| Feature | Location | Size | | | Type |
|---|---|---|---|---|---|
| LHA | 1 .. 400 | 400 bp | | ⊢⊣ | misc_feature |
| CF coding sequence second half | 401 .. 1960 | 1560 bp | | ⊢⊣ | misc_feature |
| BGH polyA sequence | 1973 .. 2199 | 227 bp | | → | misc_feature |
| PGK promoter | 2206 .. 2726 | 521 bp | | ⊢⊣ | misc_feature |
| /note | = Naldini;Addgene;pLenti.PGK.LifeAct-GFP.Whttps://www.addgene.org/51010/ type=misc_feature vntifkey=21 | | | | |
| Truncated CD19 | 2727 .. 3728 | 1002 bp | | → | CDS |
| /translation | = MPPPRLLFFLLFLTPMEVRPEEPLVVKVEEGDNAVLQCLKGTSDGPTQQLTWSRESPLKPFLKLSLGLPGLGIHMRPLA IWLFIFNVSQQMGPFYLCQPGPPSEKAWQPGWTVNVEGSGELFRWNVSDLGGLGCGLKNRSSEGPSSPSGKLMS PKLYVWAKDRPEIWEGEPPCLPPRDSLNQSLSQDLTMAPGSTLWLSCGVPPDSVSRGPLSWTHVHPKGPKSLLSLE LKDQRPARDHWVMFTGLLLPSATAQDAGKYYCHRGNLTMSFHLEITARPVLWHWLLRTGGWKVSAVTLAYLIPCLCS LVGILHLQRALVLRRKRKRMTDPTRRF* SEQ ID NO:22 | | | | |
| | 333 amino acids = 37.3 kDa | | | | |
| mEYFP | 2727 .. 2729 | 3 bp | | → | CDS |
| /product | = enhanced YFP with monomerizing A206K mutation (Zacharias et al., 2002) | | | | |
| /note | = mammalian codon-optimized | | | | |
| /translation | = M | | | | |
| | 1 amino acid = 149.2 Da | | | | |
| SV40 polyA | 3755 .. 3873 | 119 bp | ■ | ⊢⊣ | polyA_site |
| /note | = vntifkey=26 | | | | |
| RHA | 3874 .. 4290 | 417 bp | | ⊢⊣ | misc_feature |
| CF-1 | 3874 .. 3890 | 17 bp | | ⊢⊣ | misc_feature |
| Stuffer | 3891 .. 4290 | 400 bp | | ⊢⊣ | misc_feature |
| R-ITR | 4299 .. 4439 | 141 bp | | → | misc_feature |
| f1 origin | 4531 .. 4837 | 307 bp | | → | misc_feature |
| AmpR promoter | 5286 .. 5314 | 29 bp | | ⊢⊣ | misc_feature |
| ORF 3 | 5356 .. 6216 | 861 bp | | → | CDS |
| /translation | = MSIQHFRVALIPFFAAFCLPVFAHPETLVKVKDAEDQLGARVGYIELDLNSGKILESFRPEERFPMMSTFKVLLCGAVLS RIDAGQEQLGRRIHYSQNDLVEYSPVTEKHLTDGMTVRELCSAAITMSDNTAANLLLTTIGGPKELTAFLHNMGDHVTR LDRWEPELNEAIPNDERDTTMPVAMATTLRKLLTGELLTLASRQQLIDWMEADKVAGPLLRSALPAGWFIADKSGAGE RGSRGIIAALGPDGKPSRIVVIYTTGSQATMDERNRQIAEIGASLIKHW* SEQ ID NO:23 | | | | |
| | 286 amino acids = 31.6 kDa | | | | |
| pBR322 origin | 6371 .. 6990 | 620 bp | | → | misc_feature |
| L-ITR | 7037 .. 7176 | 140 bp | | → | misc_feature |

CRISPR/CAS 9-MEDIATED INTEGRATION OF POLYNUCLEOTIDES BY SEQUENTIAL HOMOLOGOUS RECOMBINATION OF AAV DONOR VECTORS

CROSS-REFERENCES TO RELATED APPLICATIONS

The present application is based on International Application No. PCT/US2018/028957 filed on Apr. 23, 2018, which claims priority to U.S. Provisional Application No. 62/488,627, filed Apr. 21, 2017, the disclosures are herein incorporated by reference in their entirety.

STATEMENT AS TO RIGHTS TO INVENTIONS MADE UNDER FEDERALLY SPONSORED RESEARCH OR DEVELOPMENT

This invention was made with Government support under contracts AI097320 and AI20766 awarded by the National Institutes of Health. The Government has certain rights in the invention.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Apr. 23, 2018, entitles 068597_5034_WO_ST25.txt which is 20 kilobytes in size.

BACKGROUND OF THE INVENTION

Precise genome editing can be accomplished using designer nucleases (e.g., ZFNs and TALENs) or RNA-guided nucleases (e.g., CRISPR/Cas9), which create site-specific double-strand breaks (DSBs) that stimulate homologous recombination (HR) when supplied with a homologous donor DNA template. The CRISPR/Cas9 system has recently been shown to facilitate high levels of precise genome editing using adeno associated viral (AAV) vectors to serve as donor template DNA during homologous recombination (HR). However, the maximum AAV packaging capacity of about 4.5 kilobases (kb) limits the size of the donor. As such, a donor DNA template with an insert exceeding about 4.0 kb can not be utilized in a single AAV vector. The present invention meets this need and provides a CRISPR/Cas9-based method that enables site-specific integration of large polynucleotides, e.g., transgenes that can be split between two or more AAV donor vectors into the genome of various types of cells including primary cells and stem cells with long-term repopulation capacity.

BRIEF SUMMARY OF THE INVENTION

In one aspect, the present invention provides a system for CRISPR/Cas9-mediated integration of a target polynucleotide into a target genetic locus in a cell. The system comprises (a) a first targeting AAV vector comprising a single guide RNA (sgRNA) target site with a protospacer-adjacent motif (PAM), a first donor template, a 5' homology arm that is homologous to a first portion of the target locus, and a 3' homology arm that is homologous to a second portion of the target locus that is not overlapping or substantially not overlapping with the first portion of the target locus, wherein the sgRNA target site is recognized by a target locus-specific sgRNA, wherein the first donor template comprises a first nucleotide sequence of the target polynucleotide; (b) a second targeting AAV vector comprising a second donor template, a 5' homology arm that is homologous to a first portion of the first donor template, a 3' homology arm that is homologous to a second portion of the first targeting AAV vector, wherein the first portion of the first donor template and the second portion of the first targeting AAV vector are not overlapping or substantially not overlapping, the second donor template comprises a second nucleotide sequence of the target polynucleotide, and the nucleotide sequence of the target polynucleotide is split between the first donor template and the second donor template; (c) the target locus-specific sgRNA; and (d) a CRISPR-associated protein 9 (Cas9) polypeptide or a polynucleotide encoding a Cas9 polypeptide.

In some embodiments, the target locus-specific sgRNA and Cas9 polypeptide are complexed together to form a Cas9 ribonucleoprotein.

In some embodiments, the target locus-specific sgRNA is a CCR5 sgRNA or a CFTR sgRNA. In certain embodiments, the target locus-specific sgRNA comprises a synthetic sgRNA of SEQ ID NO: 1 or SEQ ID NO:14.

In some embodiments, the target locus-specific sgRNA comprises one or more modified nucleotides. The modified nucleotides can comprise a modification in a ribose group, a phosphate group, a nucleobase, or a combination thereof. The modification in a ribose group can comprise a modification at the 2' position of the ribose group. The modification at the 2' position of the ribose group can be selected from the group consisting of 2'-O-methyl, 2'-fluoro, 2'-deoxy, s'-O-(2-methoxyethyl), and a combination thereof. In some embodiments, the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

In some embodiments, the first targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In certain embodiments, the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In some instances, the first targeting AAV vector and the second targeting AAV vector have the same AAV capsid polypeptide.

In some embodiments, the cell is isolated from a subject, e.g., a human subject. The isolated cell can be a primary cell, such as any cell obtained from a subject. In certain embodiments, the subject has a genetic disease.

In a second aspect, the present invention provides a method of introducing a target polynucleotide into a target genetic locus in a cell. The method comprises introducing into the cell: (a) a first targeting AAV vector comprising a single guide RNA (sgRNA) target site with a protospacer-adjacent motif (PAM), a first donor template, a 5' homology arm that is homologous to a first portion of the target locus, and a 3' homology arm that is homologous to a second portion of the target locus that is not overlapping or substantially not overlapping with the first portion of the target locus, wherein the sgRNA target site is recognized by a target locus-specific sgRNA, wherein the first donor template comprises a first nucleotide sequence of the target polynucleotide; (b) a second targeting AAV vector comprising a second donor template, a 5' homology arm that is homologous to a first portion of the first donor template, a 3' homology arm that is homologous to a second portion of the first targeting AAV vector, wherein the first portion of the first donor template and the second portion of the first targeting AAV vector are not overlapping, the second donor template comprises a second nucleotide sequence of the target polynucleotide, and the nucleotide sequence of the target polynucleotide is split between the first donor template and the second donor template; (c) the target locus-specific sgRNA; and (d) a CRISPR-associated protein 9 (Cas9) polypeptide or a polynucleotide encoding a Cas9 polypeptide. In some embodiments, the method further comprises selecting (and/or isolating) the cell containing the target polynucleotide.

In some embodiments, the target locus-specific sgRNA and Cas9 polypeptide are complexed together to form a Cas9 ribonucleoprotein.

In some embodiments, the target locus-specific sgRNA is a CCR5 sgRNA or a CFTR sgRNA. In certain embodiments, the target locus-specific sgRNA comprises a synthetic sgRNA of SEQ ID NO:1 or SEQ ID NO:14.

In some embodiments, the target locus-specific sgRNA comprises one or more modified nucleotides. In some instances, the modified nucleotides comprise a modification in a ribose group, a phosphate group, a nucleobase, or a combination thereof. The modification in a ribose group can comprise a modification at the 2' position of the ribose group. The modification at the 2' position of the ribose group can be selected from the group consisting of 2'-O-methyl, 2'-fluoro, 2'-deoxy, s'-O-(2-methoxyethyl), and a combination thereof. In some embodiments, the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and/or a combination thereof.

In some embodiments, the first targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In certain embodiments, the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In some instances, the first targeting AAV vector and the second targeting AAV vector have the same AAV capsid polypeptide. In certain instances, the first targeting AAV vector and the second targeting AAV vector have different AAV capsid polypeptides.

In some embodiments, the cell is isolated from a subject, e.g., a human subject prior to performing the method. For instance, the cell is obtained from a subject before introducing the first targeting AAV vector, the second targeting AAV vector, the target-locus specific sgRNA, and the Cas9 polypeptide or polynucleotide encoding the Cas9 polynucleotide into the cell. In some cases, the cell is obtained from a subject before introducing the first targeting AAV vector, the second targeting AAV vector, and a Cas9 ribonucleoprotein into the cell.

In certain embodiments, the method further comprises administering the cell containing the target polynucleotide (e.g., a cell containing the target polynucleotide inserted into the target genetic locus) into the subject. In other words, the cell can be obtained from the subject prior to sequential homologous recombination, and then after successful incorporation of the target polynucleotide into the target genetic locus, the resulting cell can be administered to the subject.

In some embodiments, the cell is selected from the group consisting of an immune cell, a muscle cell, a liver cell, a skin cell, a retinal cell, an airway cell, a lung cell, and a stem cell. In some cases, the subject has a genetic disease.

In a third aspect, the present invention provides a method of treating a genetic disease in a subject. The method comprises administering to the subject: (a) a first targeting AAV vector comprising a single guide RNA (sgRNA) target site with a protospacer-adjacent motif (PAM), a first donor template, a 5' homology arm that is homologous to a first portion of the target locus, and a 3' homology arm that is homologous to a second portion of the target locus that is not overlapping or substantially not overlapping with the first portion of the target locus, wherein the sgRNA target site is recognized by a target locus-specific sgRNA, wherein the first donor template comprises a first nucleotide sequence of the target polynucleotide; (b) a second targeting AAV vector comprising a second donor template, a 5' homology arm that is homologous to a first portion of the first donor template, a 3' homology arm that is homologous to a second portion of the first targeting AAV vector, wherein the first portion of the first donor template and the second portion of the first targeting AAV vector are not overlapping, the second donor template comprises a second nucleotide sequence of the target polynucleotide, and the nucleotide sequence of the target polynucleotide is split between the first donor template and the second donor template; (c) the target locus-specific sgRNA; and (d) a CRISPR-associated protein 9 (Cas9) polypeptide or a polynucleotide encoding a Cas9 polypeptide.

In some embodiments, the target locus-specific sgRNA and Cas9 polypeptide are complexed together to form a Cas9 ribonucleoprotein.

In some embodiments, the target locus-specific sgRNA is a CCR5 sgRNA or a CFTR sgRNA. In certain embodiments, the target locus-specific sgRNA comprises a synthetic sgRNA of SEQ ID NO:1 or SEQ ID NO:14.

In some embodiments, the target locus-specific sgRNA comprises one or more modified nucleotides. In some instances, the modified nucleotides comprise a modification in a ribose group, a phosphate group, a nucleobase, or a combination thereof. The modification in a ribose group can comprise a modification at the 2' position of the ribose group. The modification at the 2' position of the ribose group can be selected from the group consisting of 2'-O-methyl, 2'-fluoro, 2'-deoxy, s'-O-(2-methoxyethyl), and a combination thereof. In some embodiments, the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

In some embodiments, the first targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In certain embodiments, the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In some instances, the first targeting AAV vector and the second targeting AAV vector have the same AAV capsid polypeptide. In certain instances, the first targeting AAV vector and the second targeting AAV vector have different AAV capsid polypeptides.

In some embodiments, provided herein is a system for CRISPR/Cas9-mediated integration of a transgene into a target gene in a cell comprising: (a) a first targeting AAV vector comprising a single guide RNA (sgRNA) target site, a protospacer-adjacent motif (PAM), a first donor template, a stuffer nucleotide sequence, a 5' homology arm that is homologous to a first portion of the target gene, and a 3' homology arm that is homologous to a second portion of the target gene that is not overlapping or substantially not overlapping with the first portion of the target gene, wherein the sgRNA target site is recognized by a target gene-specific sgRNA, wherein the PAM is 5' of the sgRNA target site, wherein the first donor template comprises a first nucleotide sequence of the transgene; (b) a second targeting AAV vector comprising a second donor template, a 5' homology arm that is homologous to a portion of the first donor template, a 3' homology arm that is homologous to the sgRNA target site and the stuffer nucleotide sequence of the first targeting AAV vector, wherein the second donor template comprises a second nucleotide sequence of the transgene, and the nucleotide sequence of the transgene is split between the first donor template and the second donor template; (c) the target gene-specific sgRNA; and (d) a CRISPR-associated protein 9 (Cas9) polypeptide or a polynucleotide encoding a Cas9 polypeptide.

In certain embodiments, a method of introducing a transgene into a target gene in a cell comprising introducing into the cell: (a) a first targeting AAV vector comprising an single guide RNA (sgRNA) target site, a protospacer-adjacent motif (PAM), a first donor template, a stuffer nucleotide sequence, a 5' homology arm that is homologous to a first portion of the target gene, and a 3' homology arm that is homologous to a second portion of the target gene that is not overlapping or substantially not overlapping with the first portion of the target gene, wherein the sgRNA target site is recognized by a target gene-specific sgRNA, wherein the PAM is 5' of the sgRNA target site, wherein the first donor template comprises a first nucleotide sequence of the transgene; (b) a second targeting AAV vector comprising a second donor template, a 5' homology arm that is homologous to a portion of the first donor template, a 3' homology arm that is homologous to the sgRNA target site and the stuffer nucleotide sequence of the first targeting AAV vector, wherein the second donor template comprises a second nucleotide sequence of the transgene, and the nucleotide sequence of the transgene is split between the first donor template and the second donor template; (c) the target gene-specific sgRNA; and (d) a CRISPR-associated protein 9 (Cas9) polypeptide or a polynucleotide encoding a Cas9 polypeptide.

In some embodiments, the target gene-specific sgRNA is a CCR5 sgRNA or a CFTR sgRNA. In certain embodiments, the target gene-specific sgRNA comprises a synthetic sgRNA of SEQ ID NO:1 or SEQ ID NO:14.

In other embodiments, provided herein is a method of treating a genetic disease in a subject, the method comprising administering to the subject: (a) a first targeting AAV vector comprising an single guide RNA (sgRNA) target site, a protospacer-adjacent motif (PAM), a first donor template, a stuffer nucleotide sequence, a 5' homology arm that is homologous to a first portion of the target gene, and a 3' homology arm that is homologous to a second portion of the target gene that is not overlapping or substantially not overlapping with the first portion of the target gene, wherein the sgRNA target site is recognized by a target gene-specific sgRNA, wherein the PAM is 5' of the sgRNA target site, wherein the first donor template comprises a first nucleotide sequence of the transgene; (b) a second targeting AAV vector comprising a second donor template, a 5' homology arm that is homologous to a portion of the first donor template, a 3' homology arm that is homologous to the sgRNA target site and the stuffer nucleotide sequence of the first targeting AAV vector, wherein the second donor template comprises a second nucleotide sequence of the transgene, and the nucleotide sequence of the transgene is split between the first donor template and the second donor template; (c) the target gene-specific sgRNA; and (d) a CRISPR-associated protein 9 (Cas9) polypeptide or a polynucleotide encoding a Cas9 polypeptide.

In some embodiments, the target gene-specific sgRNA is a CCR5 sgRNA or a CFTR sgRNA. In certain embodiments, the target gene-specific sgRNA comprises a synthetic sgRNA of SEQ ID NO:1 or SEQ ID NO:14.

Integration of transgenes into specific sites of the genome of primary cells using CRISPR/Cas9 and AAV donor vectors is currently hampered by the limited packaging capacity of AAV. Provided herein is a method for efficient integration of large transgenes that exceed the capacity of a single AAV. Two AAV donors can be designed to undergo sequential homologous recombination (HR). In some embodiments, a transgene split between two AAV donors can be fused during HR. CRISPR and two AAV donor can mediate integration of large transgene cassettes.

Other objects, advantages and embodiments of the invention will be apparent from the detailed description following.

BRIEF DESCRIPTION OF THE DRAWING

FIG. 1A shows a schematic overview of a 2-step HR platform, in which a gene is split between two HR donors (donor A and B), which undergo sequential HR. Donor A carries a sgRNA target site (red box) immediately after 'part A' of the transgene. This allows HR of donor B using the same sgRNA, which seamlessly fuses 'part B' of the transgene to 'part A'. Stuffer DNA (white box) after the sgRNA target site is used as homology arm for donor B to avoid re-using the right homology arm from donor A. FIG. 1B shows that K562 cells were mock-electroporated or electroporated with Cas9 mRNA and CCR5 synthetic sgRNAs (CRISPR) followed by transduction with a split GFP AAV6 donor pair (see FIGS. 4 and 5). GFP expression was measured by flow cytometry 16 days after transduction. FIG. 1B, left panel, representative FACS plots. FIG. 1B, right panel, frequencies of GFP+ cells, N=4, error bars represent SD.

FIG. 2A shows that primary human T cells and CD34+ hematopoietic stem and progenitor cells (HSPCs) were mock-electroporated or electroporated with Cas9 protein precomplexed with CCR5 chemically modified sgRNAs (CRISPR) followed by transduction with a split GFP AAV6 donor pair (FIGS. 4 and 5). GFP expression was measured by flow cytometry four days after transduction. FIG. 2A, left panel, representative FACS plots from the two cell types. FIG. 2A, right panel, frequencies of GFP+ cells for the two cell types, N=11 (T cells, all from different buffy coat donors), N=12 (HSPCs, all from different cord blood donors). FIG. 2B shows that HSPCs were treated as in FIG. 2A and at day 4 post-transduction, GFP+ cells were single-cell sorted into 96-well plates containing methylcellulose and progenitor-derived clones were visualized 14 days after seeding. FIG. 2B, top panel, fluorescent microscopy images of formed GFP+ colonies from erythroid (BFU-E), granulocyte/macrophage (CFU-GM), and multi-lineage (CFU-GEMM) progenitors (scale bars: blue=200 μm, red=1000 μm, green=400 μm). FIG. 2B, bottom panel, In-Out PCR was performed on colony-derived genomic DNA to confirm targeted integration at the 5' end (donor A) and at the 3' end (donor B) (FIG. 14). Representative gel image of 6 clones of a total of 41 clones analyzed. Input control is PCR amplification of a part of the HBB gene.

FIG. 3A shows a schematic overview of a 2-step HR platform integrating an EGFR expression cassette into the CCR5 gene. Donor A carries all elements of the expression cassette, but only 'part A' of the EGFR coding sequence followed by the same sgRNA target site (red box) used for HR of donor A. 'Part B' is introduced by HR using this sgRNA target site and is fused seamlessly with 'part A' thereby constituting a full EGFR open reading frame. FIG. 3B shows that primary human T cells and CD34+ HSPCs were mock-electroporated or electroporated with Cas9 protein precomplexed with CCR5 sgRNA (CRISPR) followed by transduction with the split EGFR AAV6 donor pair. FIG. 3B, left panel, representative FACS plots showing EGFR expression four days post-transduction.

FIG. 3B, right panel, frequencies of EGFR+ cells measured four days post-transduction, N=14 (T cells, all from different buffy coat donors), N=9 (HSPCs, all from different cord blood donors). FIG. 3C shows that HSPCs were treated as in FIG. 3B and at day 4 post-transduction, EGFR+ cells were single-cell sorted into 96-well plates containing methylcellulose and In-Out PCR was performed on genomic DNA from progenitor-derived clones 14 days after seeding. Representative gel image shows targeted integration of donor A and B, confirmed by the 5' end and 3' end PCR, respectively, in 6 out of 20 total colonies. Input control is PCR amplification of part of the HBB gene.

(FIG. 8A) K562 cells were mock-electroporated or electroporated with Cas9 mRNA and CCR5-targeting sgRNA (CRISPR) and then transduced with the split GFP AAV6 donors. GFP levels were measured by flow cytometry 4 and 16 days after electroporation. (FIG. 8B) K562 cells were treated as in FIG. 8A and analyzed by flow cytometry 16 days after electroporation. Representative FACS plots are from one of the samples shown in FIG. 2C. Almost all GFP+ cells (94.4%) are also double-positive for BFP and mCherry expression. Analogously, out of all cells double-positive for BFP and mCherry, 91.4% also express GFP. This supports the intended design, that reconstitution of the GFP cassette requires targeting of both Donor A (BFP) and Donor B (mCherry). Among all cells targeted with Donor A (all BFP+ cells: 14.5%+38.9%=53.4%), approximately 27% do not get targeted by donor B (14.5%/53.4%). (FIG. 8C) K562 cells were treated as in (FIG. 8A) using a Donor A wither either an intact PAM (NGG) or a mutated PAM (NTA). Representative FACS plots are shown from flow cytometric analysis 8 days after electroporation (left panel), and data from independent replicate experiments are shown in the bar graph (right panel), columns represent mean+SD, N=3.

FIG. 11A provides a schematic representation of the single CCR5 AAV6 donor used to assess targeted integration into the CCR5 locus. The donor contains left and right homology arms (LHA and RHA), which flank the expression cassette with either an SFFV or EF1α promoter, the GFP gene, and the BGH polyadenylation signal. Representative FACS plots 4 days after CCR5 Cas9 RNP electroporation (CRISPR) and CCR5 AAV6 donor transduction of CD34+ HSPCs (FIG. 11B). The GFP$^{high}$ population is gated, which when using a single GFP-encoding donor is the population with targeted integration. FIG. 11C depicts the percentage of targeted integration in T cells and CD34+ HSPCs using a single donor. Bars represent means, N=8 (T cells from 8 different buffy coat donors) and N=16 (CD34+ HSPCs from 16 different umbilical cords).

and N=3 (CD34+ HSPCs from 3 different umbilical cords), p<0.05; student's paired T test.

Figure 17A:
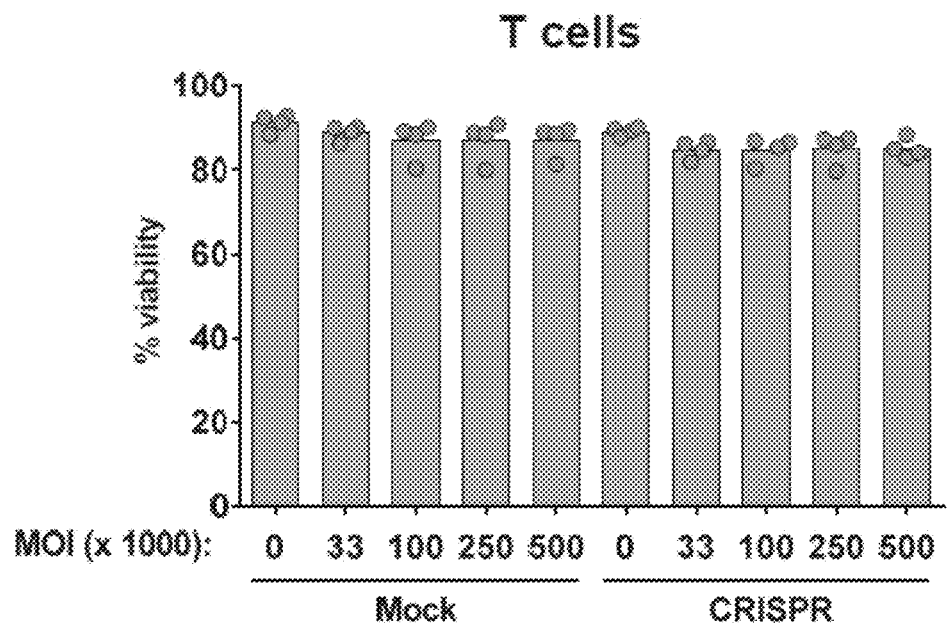
Figure 17B:
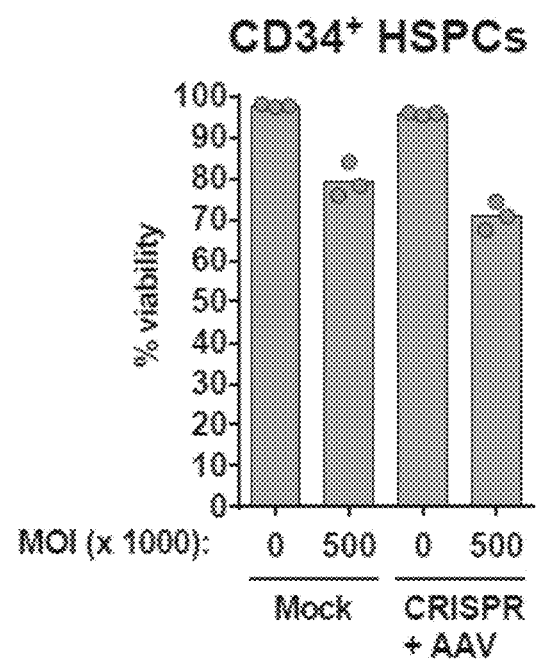

FIGS. 17A-17B show viabilities of the EGFR split donor system in primary human T cells and CD34+ HSPCs. Activated primary human T cells (FIG. 17A) or CD34+ HSPCs (FIG. 17B) were electroporated with Cas9 RNP (CRISPR) or mock-electroporated and then transduced with increasing MOIs of AAV6 split EGFR donors (MOI is per donor). Viabilities were assessed by flow cytometry three days after electroporation and transduction and live cells were discriminated as negative for an amine reactive viability dye and annexin V stain. N=4 for T cells (from four different buffy coat donors) and N=3 for CD34+ HSPCs (3 different cord blood donors).

Figure 18:
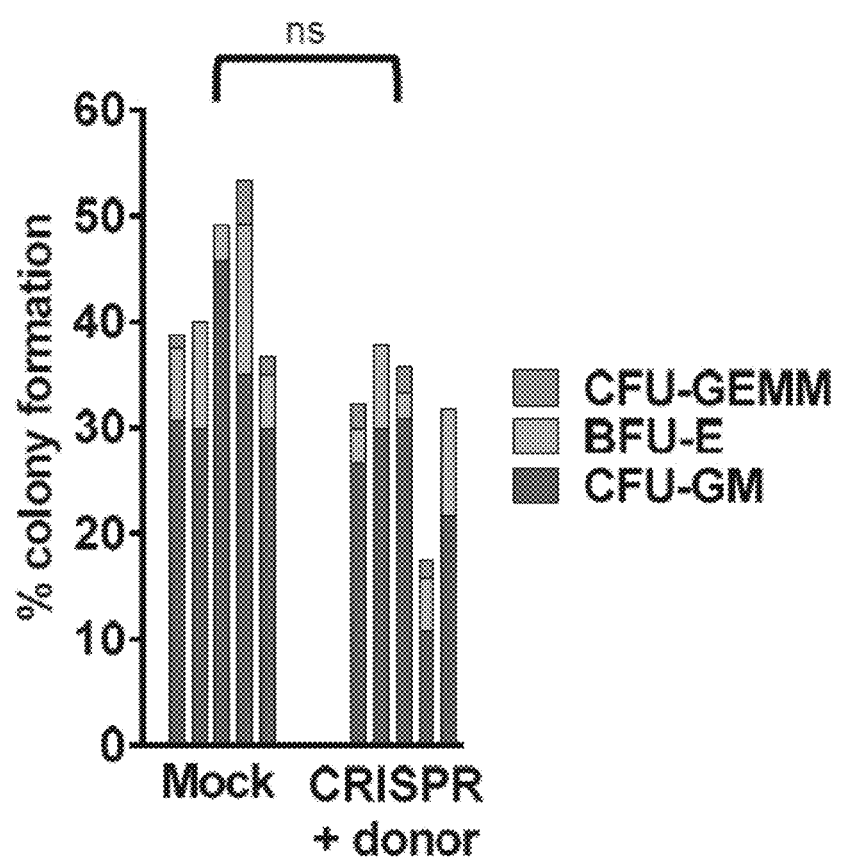

FIG. 18 provides results of a CFU assay on EGFR+ HSPCs engineered using the split EGFR donor pair. Cord blood-derived CD34+ HSPCs were cultured for two days and then electroporated with Cas9 RNP or mock-electroporated. The split EGFR AAV6 donor pair was added at an MOI of 2×500,000 and after four days, EGFR+ cells were single-cell sorted into 96-well plates containing methylcellulose. Formed colonies were counted and scored 14 days after seeding (FIG. 18). Colony type distribution showed no difference between the two groups (p≥0.39; student's paired T test) while a non-statistical significant 1.4-fold difference in total colony formation was observed (p=0.11; student's paired T test). Each bar represents results from a unique cord blood donor, N=5.

Figure 19A:
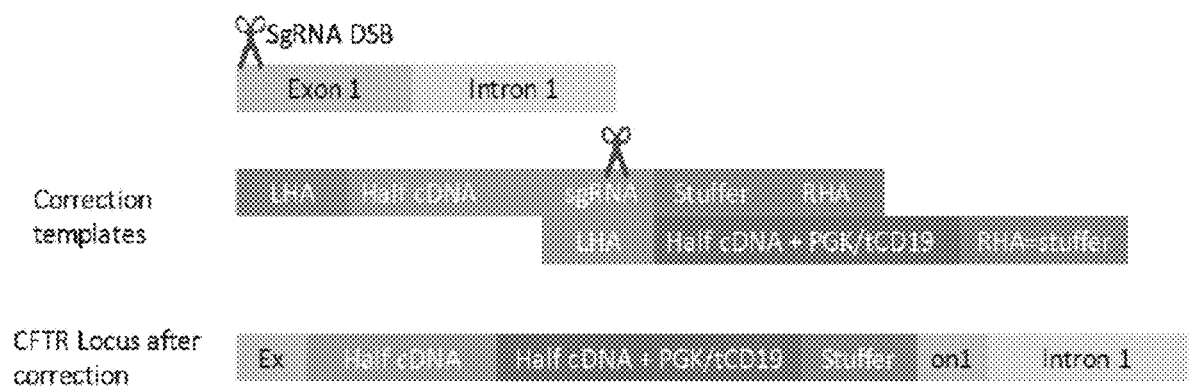
Figure 19B:
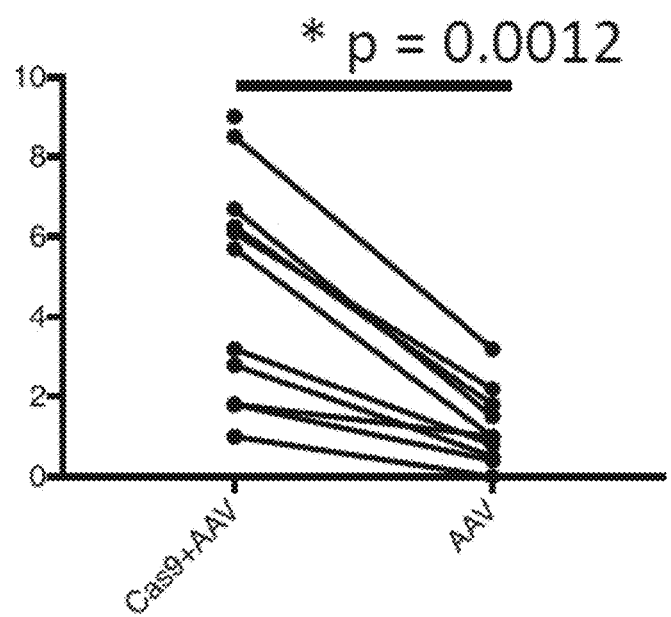
Figure 19C:
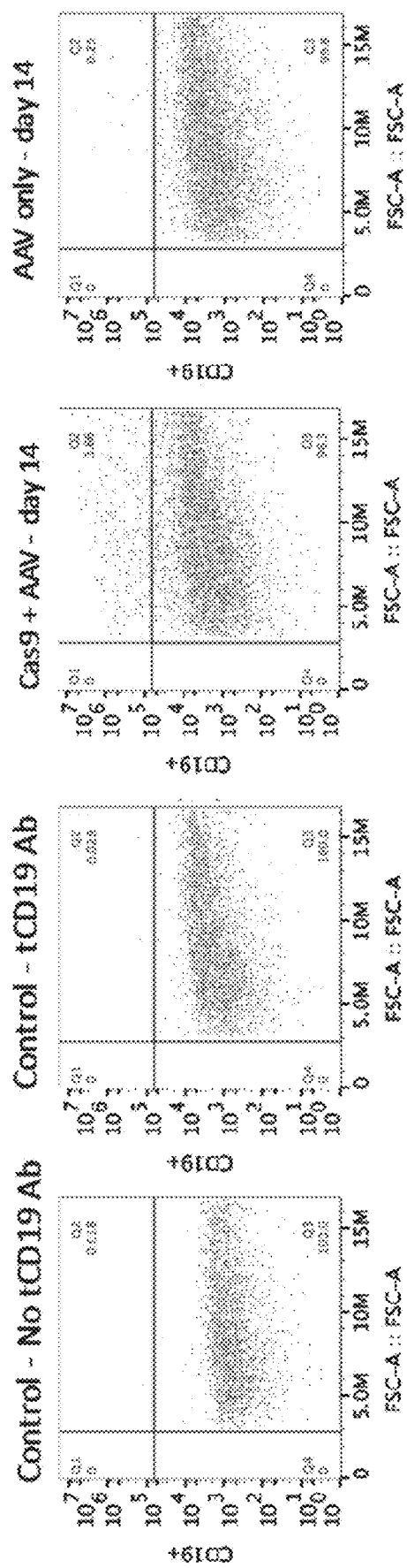
Figure 19D:
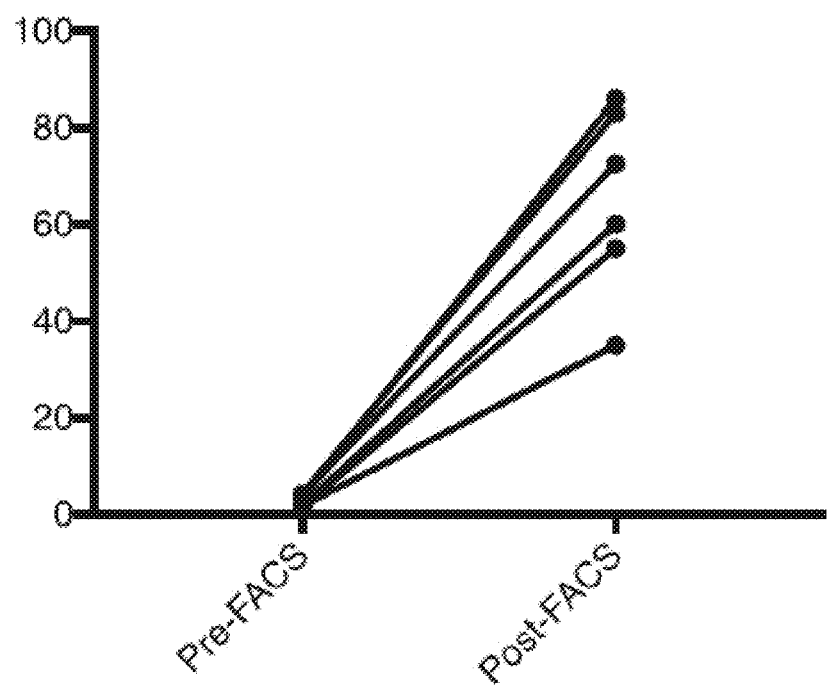

FIGS. 19A-19D show results of CFTR-Universal Correction using the split strategy described herein on stem cells, e.g., sinus stem cells. Schematics of the two correction templates and the CFTR locus after correction are provided in FIG. 19A. Correction using these two templates and the CRISPR/Cas9 system resulted in 1-10% tCD19+ cells (FIG. 19B). FACS plots show sinus cells edited using tCD19 strategy at day 14 (FIG. 19C). FACS enrichment of cells edited using tCD19 strategy resulted in 40-80% tCD19+ cells (FIG. 19D).

Figure 20A:
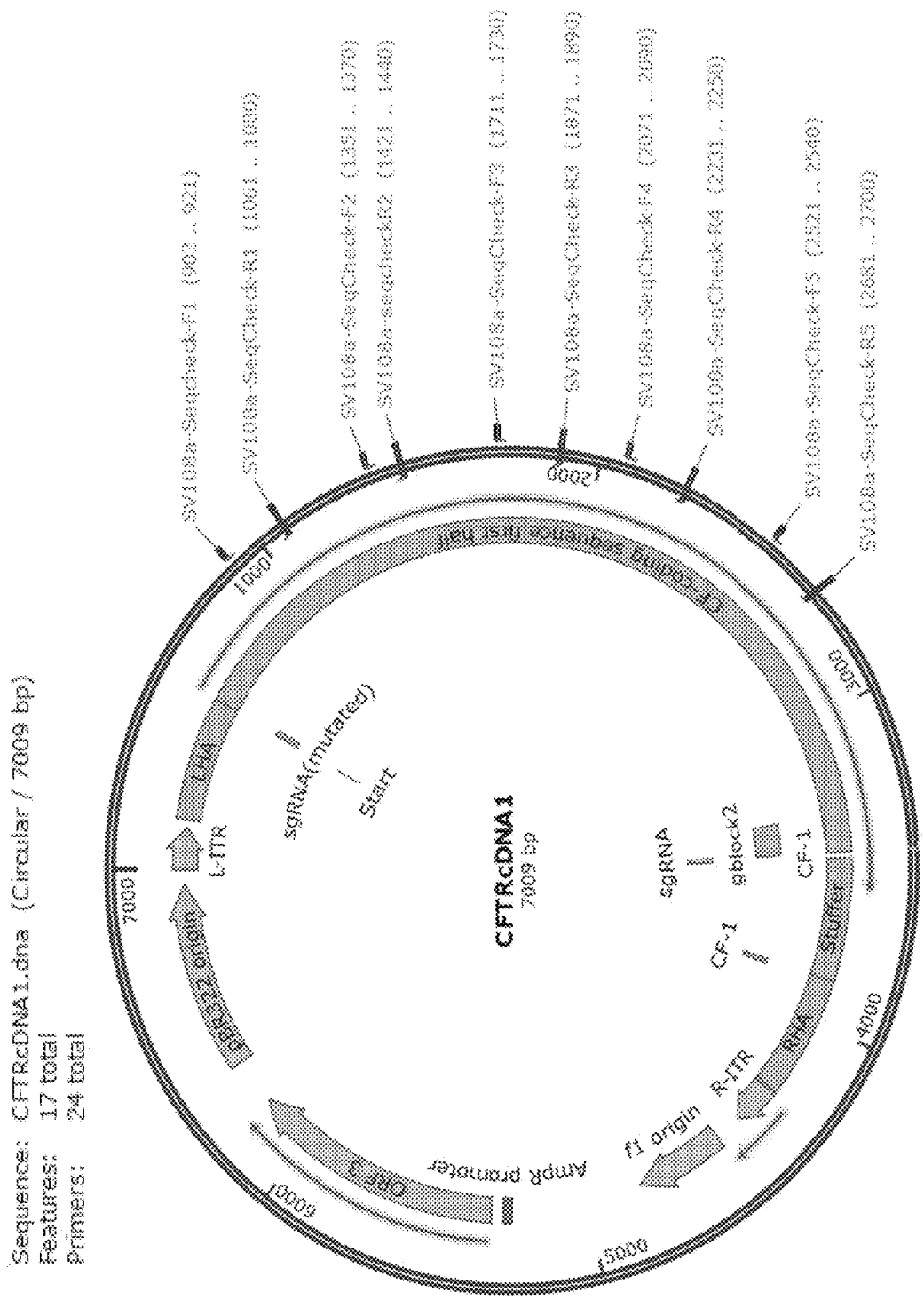

FIGS. 20A-20B show the first template for CFTR correction (SEQ ID NO: 15). FIG. 20A depicts the vector map and FIG. 20B depicts the features of the vector map.

Figure 21A:
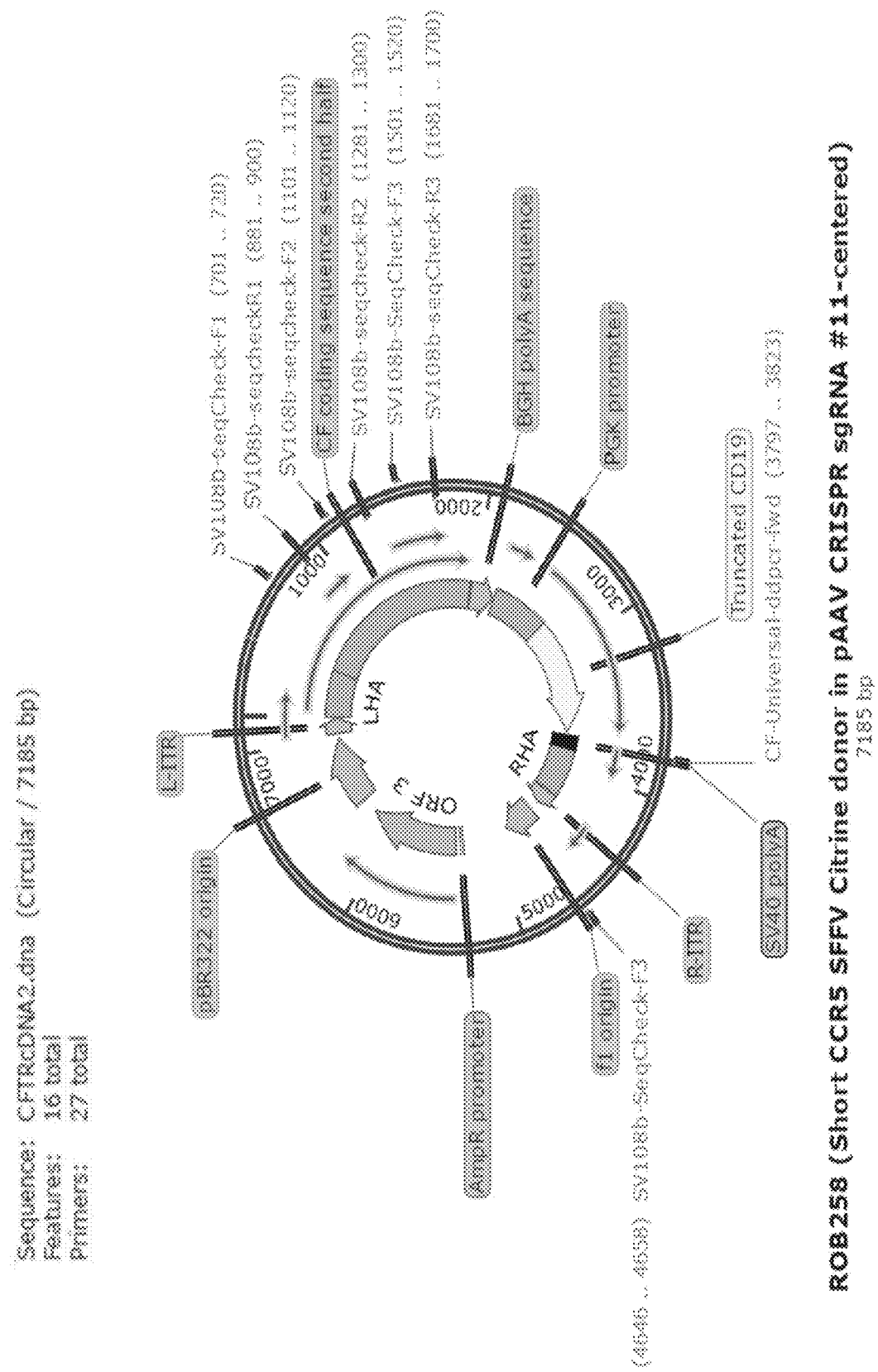

FIGS. 21A-21B show the second template for CFTR correction (SEQ ID NO:16).

FIG. 21A depicts the vector map and FIG. 21B depicts the features of the vector map.

DETAILED DESCRIPTION OF THE INVENTION

Introduction

Disclosed herein is a system and method to efficiently modify the genome of cells in order to treat diseases, e.g., genetic diseases using homologous recombination with donor DNA delivered by two or more adeno-associated virus (AAV) vectors to integrate several kilobases of DNA that exceed the packaging capacity of a single AAV vector.

The system and method can precisely insert a target polynucleotide (donor DNA) that is larger than about 4 kb into a specific genetic locus of a primary cell via sequential homologous recombination (HR) and CRISPR-mediated genome editing. The system and method generates a DNA double-stranded break (DSB) at a specific site in the genetic locus and repairs the DSB via sequential HR (two-step HR) by using two recombinant adeno-associated viruses (AAVs), each containing a portion of the HR donor template. Sequential or iterative homologous recombination in cells is effective even if the size of the target polynucleotide exceeds the packaging capacity of AAV, which is about 4.5 kb from AAV Inverted Terminal Repeat (ITR) to ITR.

Provided herein is a genomic editing system and method that can seamlessly fuse two portions of a large target polynucleotide together via consecutive homologous recombination events using two different AAV donor vectors containing different donor templates and the CRISPR/Cas9 genomic editing system. In some embodiments, the first donor template contains a first portion of the target polynucleotide and the same sgRNA target site that mediates its integration into the target genetic locus. This sgRNA site is reconstituted in the genome after integration. In the second homologous recombination event, the second donor template fuses a second portion of the target polynucleotide to the first portion using the introduced sgRNA target site.

DETAILED DESCRIPTION

The practice of the present invention employs, unless otherwise indicated, conventional techniques of immunology, biochemistry, chemistry, molecular biology, microbiology, cell biology, genomics and recombinant DNA, which are within the skill of the art. See, e.g., Sambrook, Fritsch and Maniatis, *Molecular Cloning: A Laboratory Manual*, 2nd edition (1989), *Current Protocols in Molecular Biology* (F. M. Ausubel, et al. eds., (1987)), the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)).

Oligonucleotides that are not commercially available can be chemically synthesized, e.g., according to the solid phase phosphoramidite triester method first described by Beaucage and Caruthers, *Tetrahedron Lett.* 22: 1859-1862 (1981), using an automated synthesizer, as described in Van Devanter et al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

As will be apparent to those of skill in the art upon reading this disclosure, each of the individual embodiments described and illustrated herein has discrete components and features readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

As described in the present invention, the following terms will be employed, and are defined as indicated below.

Abbreviations

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

Definitions

The term "homology-directed repair," "HDR," "homologous recombination," or "HR" refers to a mechanism in cells to accurately and precisely repair double-strand DNA breaks using a homologous template to guide repair.

The term "Cas9" refers to an RNA-guided double-stranded DNA-binding nuclease protein or nickase protein, or a variant thereof. Herein, "Cas9" refers to both naturally-occurring and recombinant Cas9s. Wild-type Cas9 nuclease has two functional domains, e.g., RuvC and HNH, that cut different DNA strands. Cas9 enzymes described herein can comprise a HNH or HNH-like nuclease domain and/or a RuvC or RuvC-like nuclease domain. Cas9 can induce double-strand breaks in genomic DNA (target locus) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor*, and *Campylobacter*. In some embodiments, the two catalytic domains are derived from different bacteria species.

The term "target genetic locus" comprises any segment or region of DNA within the genome that one desires to integrate and insert a nucleic acid. The terms "target genetic locus" and "target genomic locus" can be used interchangeably. The genomic locus of interest can be native to the cell, or alternatively can comprise a heterologous or exogenous segment of DNA that was integrated into the genome of the cell. Such heterologous or exogenous segments of DNA can include transgenes, expression cassettes, polynucleotide encoding selection makers, or heterologous or exogenous regions of genomic DNA. The term "locus" is defined herein as a segment of DNA within the genomic DNA. Genetic modifications as described herein can include one or more deletions from a locus of interest, additions to a locus of interest, replacement of a locus of interest, and/or any combination thereof. The locus can comprise coding regions or non-coding regulatory regions.

The terms "polynucleotide," "nucleotide," and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA, tRNA, lncRNA, RNA antagomirs, and inhibitory DNA or RNA (RNAi, e.g., small or short hairpin (sh)RNA, microRNA (miRNA), aptamers, small or short interfering (si)RNA, trans-splicing RNA, or antisense RNA). Polynucleotides also include non-coding RNA, which include for example, but are not limited to, RNAi, miRNAs, lncRNAs, RNA antagomirs, aptamers, and any other non-coding RNAs known to those of skill in the art. Polynucleotides include naturally occurring, synthetic, and intentionally altered or modified polynucleotides as well as analogues and derivatives. The term "polynucleotide" also refers to a polymeric form of nucleotides of any length, including deoxyribonucleotides or ribonucleotides, or analogs thereof, and is synonymous with nucleic acid sequence. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment as described herein encompassing a polynucleotide encompasses both the double-stranded form and each of two complementary single-stranded forms known or predicted to make up the double-stranded form. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

The term "nucleotide analog" or "modified nucleotide" refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate.

The term "gene" or "nucleotide sequence encoding a polypeptide" refers to the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons). For example, a gene includes a polynucleotide containing at least one open reading frame capable of encoding a particular protein or polypeptide after being transcribed and translated.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. The terms "polypeptide," "peptide," and "protein" are used interchangeably herein to refer to polymers of amino acids of any length. The terms also encompass a modified amino acid polymer; for example, disulfide bond formation, glycosylation, lipidation, phosphorylation, methylation, carboxylation, deamidation, acetylation, or conjugation with a labeling component.

The term "variant" refers to a form of an organism, strain, gene, polynucleotide, polypeptide, or characteristic that deviates from what occurs in nature, and from what is commonly referred to as wild-type.

"Recombinant" refers to a genetically modified polynucleotide, polypeptide, cell, tissue, or organism. For example, a recombinant polynucleotide (or a copy or complement of a recombinant polynucleotide) is one that has been manipulated using well known methods. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or *Current Protocols in Molecular Biology* Volumes 1-3, John Wiley & Sons, Inc. (1994-1998)). A recombinant expression cassette (or expression vector) typically comprises polynucleotides in combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide). A recombinant virus is a viral particle encapsidating a recombinant polynucleotide. The terms respectively include replicates of the original polynucleotide construct and progeny of the original virus construct.

The term "homologous" in terms of a nucleotide sequence includes a nucleotide (nucleic acid) sequence that is either identical or substantially similar to a known reference sequence. In one embodiment, the term "homologous nucleotide sequence" is used to characterize a sequence having nucleic acid sequence that is at least 70%, at least 75%, at least 80%, at least 85%, at least 90%, at least 95%, at least 96%, at least 97%, at least 98%, at least 99%, or 100% identical to a known reference sequence.

The term "substantially not overlapping" in the context of homology arms refers to a homology arm having at one end about 1 to about 5, e.g., 1, 2, 3, 4, or 5 overlapping (similar or same) base pairs with one end of a second homology arm. In some embodiments, homology arms are substantially not overlapping if they overlap by 1, 2, 3, 4 or 5 base pairs when aligned to a target genetic locus.

By the term "highly conserved" in the context of a nucleotide or amino acid sequence is meant at least about 80% sequence identity, at least about 90% sequence identity, at least about 95% sequence identity, and over about 97% sequence identity. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to about 24 nucleotides, at least about 28 to about 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids.

An "expression cassette" is a nucleic acid construct, generated recombinantly or synthetically, with a series of specified nucleic acid elements that permit transcription of a particular polynucleotide sequence in a host cell. An expression cassette or vector may be part of a plasmid, viral genome, or nucleic acid fragment. Typically, an expression cassette or vector includes a polynucleotide to be transcribed, operably linked to a promoter.

The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant protein produced from the expression vector.

The term "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

"Heterologous" means derived from a genotypically distinct entity from the rest of the entity to which it is being compared to. For example, a polynucleotide introduced by genetic engineering techniques into a plasmid or vector derived from a different species is a heterologous polynucleotide. A promoter removed from its native coding sequence and operatively linked to a coding sequence it is not naturally found linked to a heterologous promoter. Although the term "heterologous" is not always used herein in reference to polynucleotides, reference to a polynucleotide even in the absence of the modifier "heterologous" is intended to include heterologous polynucleotides in spite of the omission.

An "isolated" plasmid, nucleic acid, vector, virus, virion, host cell, or other substance refers to a preparation of the substance devoid of at least some of the other components present where the substance or a similar substance naturally occurs or from which it is initially prepared. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

An "AAV vector" as used herein refers to an AAV vector nucleic acid sequence encoding for various nucleic acid sequences, including in some embodiments a variant or chimeric capsid polypeptide (i.e., the AAV vector comprises a nucleic acid sequence encoding for a variant or chimeric capsid polypeptide). AAV vectors can also comprise a heterologous nucleic acid sequence not of AAV origin as part of the nucleic acid insert. This heterologous nucleic acid sequence typically comprises a sequence of interest for the genetic transformation of a cell. In general, the heterologous nucleic acid sequence is flanked by at least one, and generally by two AAV inverted terminal repeat sequences (ITRs).

An "AAV virion" or "AAV virus" or "AAV viral particle" or "AAV vector particle" refers to a viral particle composed of at least one AAV capsid polypeptide and an encapsidated polynucleotide AAV transfer vector. If the particle comprises a heterologous nucleic acid (i.e. a polynucleotide other than a wild-type AAV genome, such as a transgene to be delivered to a cell), it can be referred to as an "AAV vector particle" or simply an "AAV vector". Thus, production of AAV virion or AAV particle necessarily includes production of AAV vector as such a vector is contained within an AAV virion or AAV particle.

"Packaging" refers to a series of intracellular events resulting in the assembly of AAV virions or AAV particles which encapsidate a nucleic acid sequence and/or other therapeutic molecule. Packaging can refer to encapsidation of one or more nucleic acid sequence(s) and/or other therapeutic molecules into a capsid comprising the variant capsid polypeptides described herein.

AAV "rep" and "cap" genes refer to polynucleotide sequences encoding replication and encapsidation proteins of adeno-associated virus (AAV). AAV rep (replication) and cap (capsid) are referred to herein as AAV "packaging genes."

A "helper virus" for AAV refers to a virus allowing AAV (e.g. wild-type AAV) to be replicated and packaged by a mammalian cell. A variety of such helper viruses for AAV are known in the art, including adenoviruses, herpesviruses, and poxviruses, such as vaccinia. The adenoviruses encompass a number of different subgroups, although Adenovirus type 5 of subgroup C is most commonly used as a helper virus. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

An "infectious" virion, virus or viral particle is one comprising a polynucleotide component deliverable into a cell tropic for the viral species. The term does not necessarily imply any replication capacity of the virus. As used herein, an "infectious" virus or viral particle is one that upon accessing a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA) or fluorescence-activated cell sorting (FACS).

A "replication-competent" virion or virus (e.g. a replication-competent AAV) refers to an infectious phenotypically wild-type virus, and is replicable in an infected cell (i.e. in the presence of a helper virus or helper virus functions). In the case of AAV, replication competence generally requires the presence of functional AAV packaging genes. In some embodiments, AAV vectors, as described herein, lack one or more AAV packaging genes and are replication-incompetent in mammalian cells (especially in human cells). In some embodiments, AAV vectors lack any AAV packaging gene sequences, minimizing the possibility of generating replication competent AAV by recombination between AAV packaging genes and an incoming AAV vector. In many embodiments, AAV vector preparations as described herein are those containing few if any replication competent AAV (rcAAV, also referred to as RCA) (e.g., less than about 1 rcAAV per $10^2$ AAV particles, less than about 1 rcAAV per $10^4$ AAV particles, less than about 1 rcAAV per $10^8$ AAV particles, less than about 1 rcAAV per $10^{12}$ AAV particles, or no rcAAV).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The term "subject" or "patient" or "individual" typically includes humans, but can also include other animals such as, e.g., other primates, rodents, canines, felines, equines, ovines, porcines, and the like. In some cases, the term "subject" includes a bacteria cell, a yeast cell, or a plant.

As used herein and in the appended claims, the singular forms "a," "an," and "the" include plural referents unless the context clearly dictates otherwise. Thus, for example, reference to "an AAV virion" includes a plurality of such virions and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

CRISPR/Cas9 Mediated Homologous Recombination

The CRISPR/Cas system for homologous recombination (HR) includes a Cas nuclease (e.g., Cas9 nuclease) or a variant or fragment thereof, a DNA-targeting RNA (e.g., single guide RNA (sgRNA) or modified sgRNA) containing a guide sequence that targets the Cas nuclease to the target genomic DNA and a scaffold sequence that interacts with the Cas nuclease, and a donor template. The CRISPR/Cas system can be utilized to create a double-strand break at a desired target gene locus in the genome of a cell, and harness the cell's endogenous mechanisms to repair the induced break by homology-directed repair (HDR).

The CRISPR/Cas9 nuclease can facilitate locus-specific chromosomal integration of exogenous DNA delivered by AAV vectors. Typically, the size of the exogenous DNA (e.g., transgene, expression cassette, and the like) that can be integrated is limited by the DNA packaging capacity of an AAV vector which is about 4.0 kb. With the inclusion of two homology arms that are necessary for homologous recombination, a single AAV vector can only deliver less than about 3.7 kb of exogenous DNA. The method described herein allows for the delivery of exogenous DNA that is 4 kb or longer by splitting the nucleotide sequence between two different AAV vectors. The donor templates are designed for sequential homologous recombination events that can integrate and fuse the two parts of the nucleotide sequence.

Sequential homologous recombination of the present invention can be performed using an engineered nuclease system for genome editing such as, but not limited to, CRISPR/Cas nucleases, zinc finger nucleases (ZFNs), transcription activator-like effector nucleases (TALENs), engineered mega-nucleases. In one aspect, a CRISPR/Cas-based nuclease system is used. Detailed descriptions of useful nuclease system can be found, e.g., in Gaj et al., *Trends Biotechnol*, 2013, July: 31(7):397-405.

In some embodiments, a nucleotide sequence encoding the Cas nuclease is present in a recombinant expression vector. In certain instances, the recombinant expression vector is a viral construct, e.g., a recombinant adeno-associated virus construct, a recombinant adenoviral construct, a recombinant lentiviral construct, etc. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. Useful expression vectors are known to those of skill in the art, and many are commercially available. The following vectors are provided by way of example for eukaryotic host cells: pXT1, pSG5, pSVK3, pBPV, pMSG, and pSVLSV40. However, any other vector may be used if it is compatible with the host cell. For example, useful expression vectors containing a nucleotide sequence encoding a Cas9 enzyme are commercially available from, e.g., Addgene, Life Technologies, Sigma-Aldrich, and Origene.

Depending on the expression system used, any of a number of transcription and translation control elements, including promoter, transcription enhancers, transcription terminators, and the like, may be used in the expression vector. Useful promoters can be derived from viruses, or any organism, e.g., prokaryotic or eukaryotic organisms. Suitable promoters include, but are not limited to, the SV40 early promoter, mouse mammary tumor virus long terminal repeat (LTR) promoter, adenovirus major late promoter (Ad MLP), a herpes simplex virus (HSV) promoter, a cytomegalovirus (CMV) promoter (such as the CMV immediate early promoter region; CMVIE), a rous sarcoma virus (RSV) promoter, a human U6 small nuclear promoter (U6), an enhanced U6 promoter, and a human HI promoter (HI), etc.

In some embodiments, polynucleotide encoding a Cas nuclease can be used in the present invention. Such a polynucleotide (e.g., mRNA) can be commercially obtained from, for example, TriLink BioTechnologies, GE Dharmacon, ThermoFisher, and the like.

In certain embodiments, a Cas nuclease (e.g., Cas9 polypeptide) can be used in the present invention. Detailed description of useful Cas9 polypeptides can be found in, e.g., Hendel et al., *Nat Biotechnol*, 2015, 33(9): 985-989 and Dever et al., *Nature*, 2016, 539: 384-389, the disclosures are herein incorporated by reference in their entirety for all purposes.

In some embodiments, a Cas nuclease (e.g., Cas9 polypeptide) is complexed with a sgRNA to form a Cas ribonucleoprotein (e.g., Cas9 ribonucleoprotein). The molar ratio of Cas nuclease to sgRNA can be any range that facilitates sequential homologous recombination of the targeting AAV vectors and target genetic locus. In some embodiments, the molar ratio of Cas9 polypeptide to sgRNA is about 1:5; 1:4; 1:3; 1:2.5; 1:2; or 1:1. In other embodiments, the molar ratio of Cas9 polypeptide to sgRNA is about 1:2 to about 1:3. In certain embodiments, the molar ratio of Cas9 polypeptide to sgRNA is about 1:2.5.

The Cas nuclease and variants or fragments thereof can be introduced into a cell (e.g., a cell isolated from a subject, or an in vivo cell such as in a subject) as a Cas polypeptide or a variant or fragment thereof, an mRNA encoding a Cas polypeptide or a variant or fragment thereof, a recombinant expression vector comprising a nucleotide sequence encoding a Cas polypeptide or a variant or fragment thereof, or a Cas ribonucleoprotein. One skilled in the art would recognize that any method of delivering an exogenous polynucleotide, polypeptide, or a ribonucleoprotein can be used. Non-limiting examples of such methods include electroporation, nucleofection, transfection, lipofection, transduction, microinjection, electroinjection, electrofusion, nanoparticle bombardment, transformation, conjugation, and the like.

Modified sgRNA

The modified sgRNAs for use in the CRISPR/Cas system for HR typically include a guide sequence (e.g., crRNA) that is complementary to a target nucleic acid sequence (target gene locus) and a scaffold sequence (e.g., tracrRNA) that interacts with a Cas nuclease (e.g., Cas9 polypeptide) or a variant or fragment thereof. A single guide RNA (sgRNA) can include a crRNA and a tracrRNA.

The modified sgRNAs described herein can contain one or more chemical modifications that increase the activity, stability, and specificity, and/or decrease the toxicity of the modified sgRNAs compared to corresponding unmodified sgRNAs when used for CRISPR-based gene regulation systems in target cells such as primary cells isolated from a subject.

In some instances, the modified sgRNA is introduced into a cell (e.g., an in vitro cell such as a primary cell for ex vivo therapy, or an in vivo cell such as in a patient) with a recombinant expression vector comprising a nucleotide sequence encoding a Cas nuclease (e.g., Cas9 polypeptide) or a variant or fragment thereof. In some embodiments, the modified sgRNA is complexed with a Cas nuclease (e.g., a Cas9 polypeptide) or a variant or fragment thereof to form a ribonucleoprotein (RNP)-based delivery system for introduction into a cell (e.g., an in vitro cell such as a primary cell for ex vivo therapy, or an in vivo cell such as in a patient). In other instances, the modified sgRNA is introduced into a cell (e.g., an in vitro cell such as a primary cell for ex vivo therapy, or an in vivo cell such as in a patient) with an mRNA encoding a Cas nuclease (e.g., Cas9 polypeptide) or a variant or fragment thereof.

Any heterologous or foreign nucleic acid (e.g., target locus-specific sgRNA and/or polynucleotide encoding a Cas9 polynucleotide) can be introduced into a cell using any method known to one skilled in the art. Such methods include, but are not limited to, electroporation, nucleofection, transfection, lipofection, transduction, microinjection, electroinjection, electrofusion, nanoparticle bombardment, transformation, conjugation, and the like.

The nucleic acid sequence of the modified sgRNA can be any polynucleotide sequence having sufficient complementarity with a target polynucleotide sequence (e.g., target DNA sequence) to hybridize with the target sequence and direct sequence-specific binding of a CRISPR complex to the target sequence. In some embodiments, the degree of complementarity between a guide sequence of the modified sgRNA and its corresponding target sequence, when optimally aligned using a suitable alignment algorithm, is about or more than about 50%, 60%, 75%, 80%, 85%, 90%, 95%, 97.5%, 990%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 35 nucleotides, 40 nucleotides, 45 nucleotides, 50 nucleotides, 75 nucleotides, or more nucleotides in length. In some instances, a guide sequence is about 20 nucleotides in length. In other instances, a guide sequence is about 15 nucleotides in length. In other instances, a guide sequence is about 25 nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

The nucleic acid sequence of a modified sgRNA can be selected using any of the web-based software described above. Considerations for selecting a DNA-targeting RNA include the PAM sequence for the Cas nuclease (e.g., Cas9 polypeptide) to be used, and strategies for minimizing off-target modifications. Tools, such as the CRISPR Design Tool, can provide sequences for preparing the modified sgRNA, for assessing target modification efficiency, and/or assessing cleavage at off-target sites. Another consideration for selecting the sequence of a modified sgRNA includes reducing the degree of secondary structure within the guide sequence. Secondary structure may be determined by any suitable polynucleotide folding algorithm. Some programs are based on calculating the minimal Gibbs free energy. Examples of suitable algorithms include mFold (Zuker and Stiegler, *Nucleic Acids Res,* 9 (1981), 133-148), UNAFold package (Markham et al, *Methods Mol Biol,* 2008, 453:3-31) and RNAfold form the ViennaRNa Package.

The sgRNA can be about 10 to about 500 nucleotides, e.g., about 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, 100 nucleotides, 105 nucleotides, 110 nucleotides, 120 nucleotides, 130 nucleotides, 140 nucleotides, 150 nucleotides, 160 nucleotides, 170 nucleotides, 180 nucleotides, 190 nucleotides, 200 nucleotides, 210 nucleotides, 220 nucleotides, 230 nucleotides, 240 nucleotides, 250 nucleotides, 260 nucleotides, 270 nucleotides, 280 nucleotides, 290 nucleotides, 300 nucleotides, 310 nucleotides, 320 nucleotides, 330 nucleotides, 340 nucleotides, 350 nucleotides, 360 nucleotides, 370 nucleotides, 380 nucleotides, 390 nucleotides, 400 nucleotides, 410 nucleotides, 420 nucleotides, 430 nucleotides, 440 nucleotides, 450 nucleotides, 460 nucleotides, 470 nucleotides, 480 nucleotides, 490 nucleotides, or about 500 nucleotides. In some embodiments, the sgRNA is about 20 to about 500 nucleotides, e.g., 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, 100 nucleotides, 105 nucleotides 110 nucleotides, 115 nucleotides, 120 nucleotides, 125 nucleotides, 130 nucleotides, 135 nucleotides, 140 nucleotides, 145 nucleotides, 150 nucleotides, 155 nucleotides, 160 nucleotides, 165 nucleotides, 170 nucleotides, 175 nucleotides, 180 nucleotides, 185 nucleotides, 190 nucleotides, 195 nucleotides, 200 nucleotides, 205 nucleotides, 210 nucleotides, 215 nucleotides, 220 nucleotides, 225 nucleotides, 230 nucleotides, 235 nucleotides, 240 nucleotides, 245 nucleotides, 250 nucleotides, 255 nucleotides, 260 nucleotides, 265 nucleotides, 270 nucleotides, 275 nucleotides, 280 nucleotides, 285 nucleotides, 290 nucleotides, 295 nucleotides, 300 nucleotides, 305 nucleotides, 310 nucleotides, 315 nucleotides, 320 nucleotides, 325 nucleotides, 330 nucleotides, 335 nucleotides, 340 nucleotides, 345 nucleotides, 350 nucleotides, 355 nucleotides, 360 nucleotides, 365 nucleotides, 370 nucleotides, 375 nucleotides, 380 nucleotides, 385 nucleotides, 390 nucleotides, 395 nucleotides, 400 nucleotides, 405 nucleotides, 410 nucleotides, 415 nucleotides, 420 nucleotides, 425 nucleotides, 430 nucleotides, 435 nucleotides, 440 nucleotides, 445 nucleotides, 450 nucleotides, 455 nucleotides, 460 nucleotides, 465 nucleotides, 470 nucleotides, 475 nucleotides, 480 nucleotides, 485 nucleotides, 490 nucleotides, 495 nucleotides, or 500 nucleotides. In certain embodiments, the sgRNA is about 20 to about 100 nucleotides, e.g., about 20 nucleotides, e.g., 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, 50 nucleotides, 51 nucleotides, 52 nucleotides, 53 nucleotides, 54 nucleotides, 55 nucleotides, 56 nucleotides, 57 nucleotides, 58 nucleotides, 59 nucleotides, 60 nucleotides, 61 nucleotides, 62 nucleotides, 63 nucleotides, 64 nucleotides, 65 nucleotides, 66 nucleotides, 67 nucleotides, 68 nucleotides, 69 nucleotides, 70 nucleotides, 71 nucleotides, 72 nucleotides, 73 nucleotides, 74 nucleotides, 75 nucleotides, 76 nucleotides, 77 nucleotides, 78 nucleotides, 79 nucleotides, 80 nucleotides, 81 nucleotides, 82 nucleotides, 83 nucleotides, 84 nucleotides, 85 nucleotides, 86 nucleotides, 87 nucleotides, 88 nucleotides, 89 nucleotides, 90 nucleotides, 91 nucleotides, 92 nucleotides, 93 nucleotides, 94 nucleotides, 95 nucleotides, 96 nucleotides, 97 nucleotides, 98 nucleotides, 99 nucleotides, or about 100 nucleotides.

One or more nucleotides of the guide sequence and/or one or more nucleotides of the scaffold sequence of the modified sgRNA can be a modified nucleotide. For instance, a guide sequence that is about 20 nucleotides in length may have 1 or more, e.g., 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, or more modified nucleotides. In some cases, the guide sequence includes at least 2 nucleotides, 3 nucleotides, 4 nucleotides, 5 nucleotides, 6 nucleotides, 7 nucleotides, 8 nucleotides, 9 nucleotides, 10 nucleotides, or more modified nucleotides. In other cases, the guide sequence includes at least 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, or more modified nucleotides. The modified nucleotides can be located at any nucleic acid position of the guide sequence. In other words, the modified nucleotides can be at or near the first and/or last nucleotide of the guide sequence, and/or at any position in between. For example, for a guide sequence that is 20 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, and/or position 20 of the guide sequence. In certain instances, from about 10% to about 30%, e.g., about 10% to about 25%, about 10% to about 20%, about 10% to about 15%, about 15% to about 30%, about 20% to about 30%, or about 25% to about 30% of the guide sequence can comprise modified nucleotides. In other instances, from about 10% to about 30%, e.g., about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%) of the guide sequence can comprise modified nucleotides.

In some embodiments, the scaffold sequence of the modified sgRNA contains one or more modified nucleotides. For example, a scaffold sequence that is about 80 nucleotides in length may have 1 or more, e.g., 1 modified nucleotide, 2 modified nucleotides, 3 modified nucleotides, 4 modified nucleotides, 5 modified nucleotides, 6 modified nucleotides, 7, modified nucleotides 8 modified nucleotides, 9 modified nucleotides, 10 modified nucleotides, 11 modified nucleotides, 12 modified nucleotides, 13 modified nucleotides, 14 modified nucleotides, 15 modified nucleotides, 16 modified nucleotides, 17 modified nucleotides, 18 modified nucleotides, 19 modified nucleotides, 20 modified nucleotides, 21 modified nucleotides, 22 modified nucleotides, 23 modified nucleotides, 24 modified nucleotides, 25 modified nucleotides, 26 modified nucleotides, 27 modified nucleotides, 28 modified nucleotides, 29 modified nucleotides, 30 modified nucleotides, 35 modified nucleotides, 40 modified nucleotides, 45 modified nucleotides, 50 modified nucleotides, 55 modified nucleotides, 60 modified nucleotides, 65 modified nucleotides, 70 modified nucleotides, 75 modified nucleotides, 76 modified nucleotides, 77 modified nucleotides, 78 modified nucleotides, 79 modified nucleotides, 80 modified nucleotides, or more modified nucleotides. In some instances, the scaffold sequence includes at least 2 modified nucleotides, 3 modified nucleotides, 4 modified nucleotides, 5 modified nucleotides, 6 modified nucleotides, 7, modified nucleotides 8 modified nucleotides, 9 modified nucleotides, 10 modified nucleotides, or more modified nucleotides. In other instances, the scaffold sequence includes at least 2 modified nucleotides, 3 modified nucleotides, 4 modified nucleotides, 5 modified nucleotides, 6 modified nucleotides, 7, modified nucleotides 8 modified nucleotides, 9 modified nucleotides, 10 modified nucleotides, 11 modified nucleotides, 12 modified nucleotides, 13 modified nucleotides, 14 modified nucleotides, 15 modified nucleotides, 16 modified nucleotides, 17 modified nucleotides, 18 modified nucleotides, 19 modified nucleotides, 20 modified nucleotides, or more modified nucleotides. The modified nucleotides can be located at any nucleic acid position of the scaffold sequence. For example, the modified nucleotides can be at or near the first and/or last nucleotide of the scaffold sequence, and/or at any position in between. For example, for a scaffold sequence that is about 80 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, position 36, position 37, position 38, position 39, position 40, position 41, position 42, position 43, position 44, position 45, position 46, position 47, position 48, position 49, position 50, position 51, position 52, position 53, position 54, position 55, position 56, position 57, position 58, position 59, position 60, position 61, position 62, position 63, position 64, position 65, position 66, position 67, position 68, position 69, position 70, position 71, position 72, position 73, position 74, position 75, position 76, position 77, position 78, position 79, and/or position 80 of the sequence. In some instances, from about 1% to about 10%, e.g., about 1% to about 8%, about 1% to about 5%, about 5% to about 10%, or about 3% to about 7% of the scaffold sequence can comprise modified nucleotides. In other instances, from about 1% to about 10%, e.g., about 1%, about 2%, about 3%, about 4%, about 5%, about 6%, about 7%, about 8%, about 9%0, or about 10% of the scaffold sequence can comprise modified nucleotides.

The modified nucleotides of the sgRNA can include a modification in the ribose (e.g., sugar) group, phosphate group, nucleobase, or any combination thereof. In some embodiments, the modification in the ribose group comprises a modification at the 2' position of the ribose.

In some embodiments, the modified nucleotide includes a 2'fluoro-arabino nucleic acid, tricycle-DNA (tc-DNA), peptide nucleic acid, cyclohexene nucleic acid (CeNA), locked nucleic acid (LNA), ethylene-bridged nucleic acid (ENA), a phosphodiamidate morpholino, or a combination thereof.

Modified nucleotides or nucleotide analogues can include sugar- and/or backbone-modified ribonucleotides (i.e., include modifications to the phosphate-sugar backbone). For example, the phosphodiester linkages of a native or natural RNA may be modified to include at least one of a nitrogen or sulfur heteroatom. In some backbone-modified ribonucleotides the phosphoester group connecting to adjacent ribonucleotides may be replaced by a modified group, e.g., of phosphothioate group. In some sugar-modified ribonucleotides, the 2' moiety is a group selected from H, OR, R, halo, SH, SR, H2, HR, $R_2$ or ON, wherein R is $C_1$-C6 alkyl, alkenyl or alkynyl and halo is F, Cl, Br, or I.

In some embodiments, the modified nucleotide contains a sugar modification. Non-limiting examples of sugar modifications include 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), azidotriphosphate (2'-azido-2'-deoxycytidine-5'-triphosphate, 2'-azido-2'-deoxyuridine-5'-triphosphate), and combinations thereof.

In some embodiments, the modified sgRNA contains one or more 2'-fluro, 2'-amino and/or 2'-thio modifications. In some instances, the modification is a 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, 5-amino-allyl-uridine, 5-bromo-uridine, 5-iodo-uridine, 5-methyl-cytidine, ribo-thymidine, 2-aminopurine, 2'-amino-butyryl-pyrene-uridine, 5-fluoro-cytidine, and/or 5-fluoro-uridine.

There are more than 96 naturally occurring nucleoside modifications found on mammalian RNA. See, e.g., Limbach et al., *Nucleic Acids Research*, 22(12):2183-2196 (1994). The preparation of nucleotides and modified nucleotides and nucleosides are well-known in the art and described in, e.g., U.S. Pat. Nos. 4,373,071, 4,458,066, 4,500,707, 4,668,777, 4,973,679, 5,047,524, 5,132,418, 5,153,319, 5,262,530, and 5,700,642. Numerous modified nucleosides and modified nucleotides that are suitable for use as described herein are commercially available. The nucleoside can be an analogue of a naturally occurring nucleoside. In some cases, the analogue is dihydrouridine, methyladenosine, methylcytidine, methyluridine, methylpseudouridine, thiouridine, deoxycytodine, and deoxyuridine.

In some cases, the modified sgRNA described herein includes a nucleobase-modified ribonucleotide, i.e., a ribonucleotide containing at least one non-naturally occurring nucleobase instead of a naturally occurring nucleobase. Non-limiting examples of modified nucleobases which can be incorporated into modified nucleosides and modified nucleotides include m5C (5-methylcytidine), m5U (5-methyluridine), m6A (N6-methyladenosine), s2U (2-thiouridine), Um (2'-O-methyluridine), m1A (1-methyl adenosine), m2A (2-methyladenosine), Am (2-1-O-methyladenosine), ms2m6A (2-methylthio-N6-methyladenosine), i6A (N6-isopentenyl adenosine), ms2i6A (2-methylthio-N6isopentenyladenosine), io6A (N6-(cis-hydroxyisopentenyl) adenosine), ms2io6A (2-methylthio-N6-(cis-hydroxyisopentenyl)adenosine), g6A (N6-glycinylcarbamoyladenosine), t6A (N6-threonyl carbamoyladenosine), ms2t6A (2-methylthio-N6-threonyl carbamoyladenosine), m6t6A (N6-methyl-N6-threonylcarbamoyladenosine), hn6A(N6-hydroxynorvalylcarbamoyl adenosine), ms2hn6A (2-methylthio-N6-hydroxynorvalyl carbamoyladenosine), Ar(p) (2'-O-ribosyladenosine(phosphate)), I (inosine), mi 1(1-methylinosine), m'lm (1,2'-O-dimethylinosine), m3C (3-methylcytidine), Cm (2T-o-methylcytidine), s2C (2-thiocytidine), ac4C (N4-acetylcytidine), f5C (5-fonnylcytidine), m5Cm (5,2-O-dimethylcytidine), ac4Cm (N4acetyl2TOmethylcytidine), k2C (lysidine), m1G (1-methylguanosine), m2G (N2-methylguanosine), m7G (7-methylguanosine), Gm (2'-O-methylguanosine), m22G (N2,N2-dimethylguanosine), m2Gm (N2,2'-O-dimethylguanosine), m22Gm (N2,N2,2'-O-trimethylguanosine), Gr(p) (2'-O-ribosylguanosine(phosphate)), yW (wybutosine), o2yW (peroxywybutosine), OHyW (hydroxywybutosine), OHyW* (undermodified hydroxywybutosine), imG (wyosine), mimG (methylguanosine), Q (queuosine), oQ (epoxyqueuosine), galQ (galtactosyl-queuosine), manQ (mannosyl-queuosine), preQo (7-cyano-7-deazaguanosine), preQi (7-aminomethyl-7-deazaguanosine), G (archaeosine), D (dihydrouridine), m5Um (5,2'-O-dimethyluridine), s4U (4-thiouridine), m5s2U (5-methyl-2-thiouridine), s2Um (2-thio-2'-O-methyluridine), acp3U (3-(3-amino-3-carboxypropyl)uridine), ho5U (5-hydroxyuridine), mo5U (5-methoxyuridine), cmo5U (uridine 5-oxyacetic acid), mcmo5U (uridine 5-oxyacetic acid methyl ester), chm5U (5-(carboxyhydroxymethyl)uridine)), mchm5U (5-(carboxyhydroxymethyl)uridine methyl ester), mcm5U (5-methoxycarbonyl methyluridine), mcm5Um (S-methoxycarbonylmethyl-2-O-methyluridine), mcm5s2U (5-methoxycarbonylmethyl-2-thiouridine), nm5s2U (5-aminomethyl-2-thiouridine), mnm5U (5-methylaminomethyluridine), mnm5s2U (5-methylaminomethyl-2-thiouridine), mnm5se2U (5-methylaminomethyl-2-selenouridine), ncm5U (5-carbamoylmethyl uridine), ncm5Um (5-carbamoylmethyl-2'-O-methyluridine), cmnm5U (5-carboxymethylaminomethyluridine), cmnm5Um (5-carboxymethylaminomethyl-2-L-Omethyluridine), cmnm5s2U (5-carboxymethylaminomethyl-2-thiouridine), m62A (N6,N6-dimethyladenosine), Tm (2'-O-methylinosine), m4C (N4-methylcytidine), m4Cm (N4,2-O-dimethylcytidine), hm5C (5-hydroxymethylcytidine), m3U (3-methyluridine), cm5U (5-carboxymethyluridine), m6Am (N6,T-O-dimethyladenosine), rn62Am (N6,N6,0-2-trimethyladenosine), m2'7G (N2,7-dimethylguanosine), m2'2'7G (N2,N2,7-trimethylguanosine), m3Um (3,2T-O-dimethyluridine), m5D (5-methyldihydrouridine), f5Cm (5-formyl-2'-O-methylcytidine), m1Gm (1,2'-O-dimethylguanosine), m'Am (1,2-O-dimethyl adenosine)irinomethyluridine), tm5s2U (S-taurinomethyl-2-thiouridine)), imG-14 (4-demethyl guanosine), imG2 (isoguanosine), or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-(C2-C6)-alkynyluracil, 5-(hydroxymethyl)uracil, 5-chlorouracil, 5-fluorouracil, 5-bromouracil, 5-hydroxy cytosine, 5-($C_1$-$C_6$)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and combinations thereof.

In some embodiments, the phosphate backbone of the modified sgRNA is altered. The modified sgRNA can include one or more phosphorothioate, phosphoramidate (e.g., N3'-P5'-phosphoramidate (NP)), 2'-O-methoxy-ethyl (2'MOE), 2'-O-methyl-ethyl (2'ME), and/or methylphosphonate linkages.

In particular embodiments, one or more of the modified nucleotides of the guide sequence and/or one or more of the modified nucleotides of the scaffold sequence of the modified sgRNA include a 2'-O-methyl (M) nucleotide, a 2'-O-methyl 3'-phosphorothioate (MS) nucleotide, a 2'-O-methyl 3'-thioPACE (MSP) nucleotide, or a combination thereof. In some instances, the modified sgRNA includes one or more MS nucleotides. In other instances, the modified sgRNA includes one or more MSP nucleotides. In yet other instances, the modified sgRNA includes one or more MS nucleotides and one or more MSP nucleotides. In further instances, the modified sgRNA does not include M nucleotides. In certain instances, the modified sgRNA includes one or more MS nucleotides and/or one or more MSP nucleotides, and further includes one or more M nucleotides. In certain other instances, MS nucleotides and/or MSP nucleotides are the only modified nucleotides present in the modified sgRNA.

Any of the modifications described herein can be combined and incorporated into any part of the modified sgRNA. In some cases, the modified sgRNA includes a structural modification, such as a stem loop (e.g., a M2 stem loop or tetraloop).

The modified sgRNA can be synthesized by any method known by one of ordinary skill in the art. In some embodiments, the modified sgRNA is chemically synthesized. Modified sgRNAs can be synthesized using 2'-O-thionocarbamate-protected nucleoside phosphoramidites. Methods are described in, e.g., Dellinger et al., *J. American Chemical Society,* 133, 11540-11556 (2011); Threlfall et al., *Organic & Biomolecular Chemistry,* 10, 746-754 (2012); and Dellinger et al, *J. American Chemical Society.* 125, 940-950 (2003). Modified sgRNAs are commercially available from, e.g., TriLink BioTechnologies (San Diego, Calif.).

Additional detailed description of useful modified sgRNAs can be found in, e.g., Hendel et al., *Nat Biotechnol,* 2015, 33(9): 985-989 and Dever et al., *Nature,* 2016, 539: 384-389, the disclosures are herein incorporated by reference in their entirety for all purposes.

Target Polynucleotides

The system and method of the present disclosure utilize two or more donor targeting AAV vectors to insert a target polynucleotide into a specific target genetic locus in a site-specific manner. The target polynucleotide can include one or more transgenes, expression cassettes, polynucleotide encoding selection makers, heterologous or exogenous regions of genomic DNA, and the like. The target polynucleotide can be divided into two or more segments, wherein each segment is contains in one donor AAV vector. An expression cassette can contain a polynucleotide of interest, a polynucleotide encoding a selection marker and/or a reporter gene along with various regulatory elements (e.g., a promoter, an enhancer, and/or a transcriptional repressor-binding element). In some embodiments, the promoter is a constitutively active promoter, an inducible promoter, including but not limited to, a chemically-regulated promoter or a physically regulated promoter (e.g., light-, heat-, or mechanically-inducible promoter), a tissue-specific promoter, a cell-specific promoter, or a synthetic promoter.

The target polynucleotide can include at least two polynucleotides of interest. For instance, the target polynucleotide inserted into the target gene locus can include two or more transgenes. In other instances, the target polynucleotide can include two or more expression cassettes, reporter genes, selectable marker genes, and the like.

In some embodiments, the nucleic acid sequence of a target polynucleotide can be divided or split into two donor templates such that the templates can be joined together by way of CRISPR/Cas9-mediated HR to produce the nucleic acid sequence of the target polynucleotide. In other words, "part A" of the nucleic acid sequence can be included in a first donor template and "part B" of the nucleic acid sequence can be included in a second donor template such that upon seamless fusion of "part A" and "part B" corresponds to the nucleic acid sequence of the target polynucleotide.

In some embodiments, a target polynucleotide introduces one or more exogenous coding and/or non-coding regions into the target gene locus. In some instances, the target polynucleotide can be multicistronic, such as containing more than one, e.g., 2, 3, or more coding regions.

One skilled in the art would recognize that the system and methods of the present invention can be applied to any polynucleotide. Non-limiting examples of target polynucleotides can include the coding regions for dystrophin, dysferlin, cystic fibrosis transmembrane conductance regulator (CFTR), myosin VIIA, ATP-binding cassette, sub-family A, member 4 (ABCA4), Factor VIII, centrosomal protein of 290 kDa (CEP290), and usherin.

The sequential homologous recombination disclosed herein can include deletion of an endogenous nucleotide sequence at a genetic locus of interest and insertion of one or more target polynucleotides at the genetic locus. In some embodiments, the target polynucleotide can change one or more base pairs of the target gene locus. In some embodiments, the target polynucleotide can replace a mutant target gene locus with a wild-type gene. In some embodiments, the target polynucleotide can replace a non-functional target gene locus with a functional gene. In other embodiments, the target polynucleotide can replace an incorrectly functioning (over functioning or under functioning) gene with a normal or wild-type functioning gene.

For instance, insertion of target polynucleotide into the target gene locus can introduce mutations, deletions, alterations, reversions, integrations, gene correction, gene replacement, gene tagging, transgene insertion, nucleotide deletion, gene disruption, translocations, gene mutation, and the like.

The target polynucleotide can be at least about 4 kb, e.g., about 4 kb, 4.1 kb, 4.2 kb, 4.3 kb, 4.4 kb, 4.5 kb, 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb or more. The target polynucleotide can be inserted into any genetic locus of a cell. The genetic locus can include a coding region, an intron, an exon, an untranslated region, a regulatory region, a promoter, or an enhancer or any combination thereof or any portion thereof. In certain embodiments, the genetic locus is a safe harbor genomic region such as an intragenic or extragenic region of the genome that can accommodate the expression of heterologous DNA without adverse effects on the host cell or organism, while permitting sufficient expression of the heterologous DNA to yield the desirable levels of the polypeptide or polynucleotide of interest.

Targeting AAV Vectors

One aspect of the present invention provides a targeting AAV vector (e.g., a first targeting AAV) comprising a sgRNA target site with a protospacer-adjacent motif (PAM), a donor template (e.g., first donor template), a 5' homology arm that can undergo homologous recombination with the target genetic locus, and a 3' homology arm that can undergo homologous recombination with the target genetic locus. The homology arms contain sequence homology to non-overlapping sequences of the target genetic locus.

In some embodiments, the first targeting AAV vector is designed such that the donor template does not include a stop codon in any reading frame downstream of the sgRNA target site. In certain embodiments, the first targeting AAV can include microRNA binding sites downstream of the sgRNA target site. In other embodiments, the first target AAV can contain a reporter gene or selectable marker for selection of target cells that have undergone both homologous recombination steps.

Another aspect of the present invention provides a targeting AAV vector (e.g., a second targeting AAV) comprising a second donor template, a 5' homology arm that can undergo homologous recombination with the first targeting AAV vector, and a 3' homology arm that can undergo homologous recombination with a different portion of the first targeting AAV vector. The homology arms contain sequence homology to non-overlapping sequences of the first targeting vector. For instance, the 5' arm can be homologous to a portion of the first donor template, and the 3' arm is homologous to the sgRNA target site.

In the first sequence of homologous recombination events, the first targeting AAV vector recombines into the target genetic locus to insert the first donor template and sgRNA target site with PAM in a site-specific manner. In the second sequence of homologous recombination events, the second targeting vector recombines with the targeted genetic locus to fuse the second donor template with the first donor template.

The first targeting AAV vector can include two homology arms for HR-mediated integration into the target gene locus. In some embodiments, each homology arm for HR into the target gene locus can be about 400 bp to about 1000 bp, e.g., about 400 bp, 450, 500, 550, 600, 650, 700, 750, 800, 850, 900, 950, or about 1000 bp in length. In certain embodiments, each homology arm is about 400 bp or longer, e.g, about 400 bp, 450, 500, 550, 600, 650, 700, 750, 800, 850, 900, 950, about 1000 bp, or longer. The homology arms of the first target AAV can be homologous to the nucleic acid sequence flanking the sgRNA target site and PAM of the target gene locus.

The second AAV vector can comprise two homology arms for HR-mediated integration into the first AAV vector such as the first donor template. In some embodiments, each homology arm of the second targeting AAV vector can be about 100 bp to about 1000 bp, e.g., about 100 bp, 150 bp, 200 bp, 250 bp, 300 bp, 350 bp, 400 bp, 450, 500, 550, 600, 650, 700, 750, 800, 850, 900, 950, or about 1000 bp. The homology arms in the second targeting AAV can have homology to the nucleic acid sequence flanking the sgRNA target site and PAM of the first targeting AAV.

The AAV capsid type of the targeting AAV vector can be selected based on the target cell. The cell can be a eukaryotic cell. In some embodiments, the eukaryotic cell is an animal cell. In some instances, the animal cell is a mammalian cell. In some instances, the mammalian cell is a human cell. In some cases, the mammalian cell (e.g., human cell) is an immune cell, hematopoietic stem cell, hematopoietic progenitor cell, muscle cell, liver cell, skin cell, neural cell, neuronal cell, retinal cell, lung cell, airway cell, stem cell, or other cell of the body. The cell can be a primary cell, such as a cell obtained or isolated from a subject, such as a human subject. In some embodiments, the primary cell is a primary human T cell. In certain embodiments, the primary cell is a CD34+ hematopoietic stem cell or a hematopoieitic progenitor cell.

In some embodiments, the stem cell (e.g., human stem cell) includes but is not limited to an embryonic stem cell, adult tissue stem cell, (i.e., somatic stem cell), bone marrow cell, progenitor cell, induced pluripotent stem cell, and reprogrammed stem cells. In some embodiments, adult stem cells can include stem cells derived from any organ or organ system of interest within the body.

The AAV capsid type of the targeting AAV vector can be selected based on the target cell from an organ or organ system of the body. Organs of the body include, but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include, but are not limited, to the integumentary system, skeletal system, muscular system, nervous system, endocrine system, cardiovascular system, lymphatic system, respiratory system, digestive system, urinary system, and reproductive system.

AAV Capsid and Vector Features

AAV vectors of the present invention can have numerous features. In some embodiments, the vectors comprise nucleic acid sequences encoding for wild-type, mutant, variant, or chimeric capsid polypeptides. In some embodiments, the AAV vectors are selected from the group consisting of AAV-DJ vectors, AAV1 vectors, AAV2 vectors, AAV3 vectors, AAV4 vectors, AAV5 vectors, AAV6 vectors, AAV7 vectors, AAV8 vectors, AAV9 vectors, AAVbb2 vectors, AAVcy5 vectors, AAVrh10 vectors, AAVrh20 vectors, AAVrh39 vectors, AAVrh43 vectors, AAVrh64R1 vectors, AAVhu37 vectors, engineered AAV vectors, and chimeric AAV vectors.

In some instances, the first targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. In certain instances, the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide. The first targeting AAV vector and the second targeting AAV vector can contain the same AAV capsid polypeptide. In other cases, the first targeting AAV vector and the second targeting AAV vector can contain different AAV capsid polypeptides.

An exemplary AAV vector can comprise a nucleic acid encoding for a wild-type (native) AAV capsid protein or a variant AAV capsid protein differing in amino acid sequence by at least one amino acid from a wild-type or parent capsid protein. The amino acid difference(s) can be located in a solvent accessible site in the capsid, e.g., a solvent-accessible loop, or in the lumen (i.e., the interior space of the AAV capsid). In some embodiments, the lumen includes the interior space of the AAV capsid. For example, the amino acid substitution(s) can be located in a GH loop in the AAV capsid polypeptide. In some embodiments, the variant capsid polypeptide comprises one or more amino acid substitution(s) in AAV1, AAV2, AAV3, AAV4, AAV5, AAV6, AAV7, AAV8, AAV9 capsid polypeptides, and the like.

In some embodiments, the present invention provides an isolated nucleic acid comprising a nucleotide sequence that encodes an AAV vector comprising an amino acid sequence having at least about 85% at least about 90%, at least about 95%, at least about 98%, at least about 99%, or 100% sequence identity to a polypeptide sequence of a wild-type (native) AAV or a sub-portion of a wild-type (native) AAV.

In some embodiments, the AAV vector packaged by the capsid polypeptides is at least about 2000 nucleic acids in total length and up to about 5000 nucleic acids in total length. In some embodiments, the AAV vector packaged by the capsid polypeptides is about 2000 nucleic acids, about 2400 nucleic acids, about 2800 nucleic acids, about 3000 nucleic acids, about 3200 nucleic acids, about 3400 nucleic acids, about 3600 nucleic acids, about 3800 nucleic acids, about 4000 nucleic acids, about 4200 nucleic acids, about 4400 nucleic acids, about 4600 nucleic acids, about 4700 nucleic acids, or about 4800 nucleic acids. In some embodiments, the AAV vector packaged by the capsid polypeptides is between about 2000 nucleic acids (2 kb) and about 5000 nucleic acids (5 kb). In some embodiments, the AAV vector packaged by the variant capsid polypeptides is between about 2400 nucleic acids (2.4 kb) and about 4800 nucleic acids (4.8 kb). In some embodiments, the AAV vector packaged by the capsid polypeptides is between about 3000 nucleic acids (3 kb) and about 5000 nucleic acids (5 kb). In some embodiments, the AAV vector packaged by the variant capsid polypeptides is between about 3000 nucleic acids (3 kb) and about 4000 nucleic acids (4 kb).

Purified infectious AAV virions can contain three major structural proteins designated VP1, VP2, and VP3 (87, 73, and 62 kDa, respectively) in an approximate ratio of 1:1:8. In some embodiments, the AAV vector has portions of the AAV vector deleted, in order to allow for more space during AAV vector packaging into an AAV virion. In some embodiments, additional sequences are deleted from the AAV vector, including but not limited to the VP2 capsid proteins (a capsid protein not required for viral infectivity), as well as other portions of the AAV vector including those described herein. In some embodiments, the deleted sequences allow for increased volume in order to package AAV vectors with increased nucleic acid insert lengths into the AAV virion as described herein. In some embodiments, the deleted sequences allow for increased interaction with a positive charge in order to package AAV vectors with increased nucleic acid insert lengths into the AAV virion as described herein.

The AAV vectors or AAV virions disclosed herein can also include conventional control elements operably linked to the heterologous nucleotide sequence (e.g., donor template) in a manner permitting transcription, translation and/or expression in a cell transfected with the AAV vector or infected with the AAV virion produced according to the present invention. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters selected from native, constitutive, inducible and/or tissue-specific, are known in the art and may be utilized.

In various embodiments, AAV vectors or AAV virions carrying a heterologous nucleotide sequence (e.g., donor template) also include selectable markers or reporter genes, e.g., sequences encoding geneticin, hygromycin or puromycin resistance, among others. Selectable reporters or marker genes can be used to signal the presence of the plasmids/vectors in bacterial cells, including, for example, examining ampicillin resistance. Other components of the plasmid may include an origin of replication. Selection of these and other promoters and vector elements are conventional and many such sequences are available (see, e.g., Sambrook et al., and references cited therein).

Host Cells and Packaging

Host cells are necessary for generating infectious AAV vectors as well as for generating AAV virions based on the disclosed AAV vectors. Various host cells are known in the art and find use in the methods of the present invention. Any host cells described herein or known in the art can be employed with the compositions and methods described herein.

A targeting AAV vector can be introduced stably or transiently into a host cell, using established techniques, including, but not limited to, electroporation, calcium phosphate precipitation, liposome-mediated transfection, baculovirus infection, and the like. For stable transformation, a targeting vector will generally further include a selectable marker, e.g., any of several well-known selectable markers such as neomycin resistance, and the like.

Generally, when delivering the AAV vector according to the present invention by transfection, the AAV vector is delivered in an amount from about 5 µg to about 100 µg DNA, about 10 to about 50 µg DNA to about $1\times10^4$ cells to about $1\times10^{13}$ cells, or about $1\times10^5$ cells. However, the relative amounts of vector DNA to host cells may be adjusted, taking into consideration such factors as the selected vector, the delivery method and the host cells selected and such adjustments are within the level of skill of one in the art.

In some embodiments, the host cell for use in generating infectious virions can be selected from any biological organism, including prokaryotic (e.g., bacterial) cells, and eukaryotic cells, including, insect cells, yeast cells and mammalian cells. A variety of cells, e.g., mammalian cells, including, e.g., murine cells, and primate cells (e.g., human cells) can be used. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, W138, HeLa, CHO, 293, Vero, NIH 3T3, PC12, Huh-7 Saos, C2C12, RAT1, Sf9, L cells, HT1080, human embryonic kidney (HEK), human embryonic stem cells, human adult tissue stem cells, pluripotent stem cells, induced pluripotent stem cells, reprogrammed stem cells, organoid stem cells, bone marrow stem cells, HLHepG2, HepG2 and primary fibroblast, hepatocyte and myoblast cells derived from mammals including human, monkey, mouse, rat, rabbit, and hamster. The requirement for the cell used is it is capable of infection or transfection by an AAV vector. In some embodiments, the host cell is one that has rep and cap stably transfected in the cell.

In some embodiments, the preparation of a host cell according to the invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods for providing the desired nucleotide sequence.

In some embodiments, introduction of the AAV vector into the host cell may also be accomplished using techniques known to the skilled artisan and as discussed throughout the specification. In some embodiments, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes providing trans-acting E1 proteins).

In addition to the AAV vector, the host cell can contain sequences to drive expression of the AAV capsid polypeptide (in the host cell and rep (replication) sequences of the same serotype as the serotype of the AAV Inverted Terminal Repeats (ITRs) found in the AAV vector, or a cross-complementing serotype. The AAV capsid and rep (replication) sequences may be independently obtained from an AAV source and may be introduced into the host cell in any manner known to one of skill in the art or as described herein. Additionally, when pseudotyping an AAV vector in an AAV8 capsid for example, the sequences encoding each of the essential rep (replication) proteins may be supplied by AAV8, or the sequences encoding the rep (replication) proteins may be supplied by different AAV serotypes (e.g., AAV1, AAV2, AAV3, AAV4, AAV5, AAV6, AAV7, and/or AAV9).

In some embodiments, the host cell stably contains the capsid protein under the control of a suitable promoter. In some embodiments, the capsid protein is supplied to the host cell in trans. When delivered to the host cell in trans, the capsid protein may be delivered via a plasmid containing the sequences necessary to direct expression of the selected capsid protein in the host cell. In some embodiments, when delivered to the host cell in trans, the vector encoding the capsid protein also carries other sequences required for packaging the AAV, e.g., the rep (replication) sequences.

In some embodiments, the host cell stably contains the rep (replication) sequences under the control of a suitable promoter. In another embodiment, the rep (replication) proteins are supplied to the host cell in trans. When delivered to the host cell in trans, the rep (replication) proteins may be delivered via a plasmid containing the sequences necessary to direct expression of the selected rep (replication) proteins in the host cell. In some embodiments, when delivered to the host cell in trans, the vector encoding the capsid protein (also carries other sequences required for packaging the AAV vector, e.g., the rep (replication) sequences.

In some embodiments, the rep (replication) and capsid sequences may be transfected into the host cell on a single nucleic acid molecule and exist stably in the cell as an unintegrated episome. In another embodiment, the rep (replication) and capsid sequences are stably integrated into the chromosome of the cell. Another embodiment has the rep (replication) and capsid sequences transiently expressed in the host cell. For example, a useful nucleic acid molecule for such transfection comprises, from 5' to 3', a promoter, an optional spacer interposed between the promoter and the start site of the rep (replication) gene sequence, an AAV rep (replication) gene sequence, and an AAV capsid gene sequence.

Although the molecule(s) providing rep (replication) and capsid can exist in the host cell transiently (i.e., through transfection), in some embodiments, one or both of the rep (replication) and capsid proteins and the promoter(s) controlling their expression be stably expressed in the host cell, e.g., as an episome or by integration into the chromosome of the host cell. The methods employed for constructing embodiments of the invention are conventional genetic engineering or recombinant engineering techniques such as those described in the references above.

In some embodiments, the packaging host cell can require helper functions in order to package the AAV vector of the invention into an AAV virion. In some embodiments, these functions may be supplied by a herpesvirus. In some embodiments, the necessary helper functions are each provided from a human or non-human primate adenovirus source, and are available from a variety of sources, including the American Type Culture Collection (ATCC), Manassas, Va. (US). In some embodiments, the host cell is provided with and/or contains an E1a gene product, an E1b gene product, an E2a gene product, and/or an E4 ORF6 gene product. In some embodiments, the host cell may contain other adenoviral genes such as VAI RNA. In some embodiments, no other adenovirus genes or gene functions are present in the host cell.

Methods for Generating an AAV Virion

A variety of methods of generating AAV virions are known in the art and can be used to generate AAV virions comprising the AAV vectors described herein. Generally, the methods involved inserting or transducing an AAV vector of the invention into a host cell capable of packaging the AAV vector into an AAV virion. Exemplary methods are described and referenced below; however, any method known to one of skill in the art can be employed to generate the AAV virions of the invention.

An AAV vector comprising a heterologous nucleic acid (e.g., a donor template) and used to generate an AAV virion can be constructed using methods that are well known in the art. See, e.g., Koerber et al. (2009) *Mol. Ther.,* 17:2088; Koerber et al. (2008) *Mol Ther.,* 16: 1703-1709; as well as U.S. Pat. Nos. 7,439,065, 6,951,758, and 6,491,907. For example, the heterologous sequence(s) can be directly inserted into an AAV genome with the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) *Molec. Cell. Biol.* 8:3988-3996; Vincent et al. (1990) Vaccines 90 (Cold Spring Harbor Laboratory Press); Carter, B. J. (1992) *Current Opinion in Biotechnology* 3:533-539; Muzyczka, N. (1992) *Curr. Topics Microbiol. Immunol.* 158:97-129; Kotin, R. M. (1994) *Human Gene Therapy* 5:793-801; Shelling and Smith (1994) *Gene Therapy* 1:165-169; and Zhou et al. (1994) *J. Erp. Med.* 179:1867-1875.

In order to produce AAV virions, an AAV vector is introduced into a suitable host cell using known techniques, such as by transfection. A number of transfection techniques are generally known in the art. See, e.g., Graham et al. (1973) *Virology,* 52:456, Sambrook et al. (1989) *Molecular Cloning, A Laboratory Manual*, Cold Spring Harbor Laboratories, New York, Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome mediated gene transfer (Mannino et al. (1988) *BioTechniques* 6:682-690), lipid-mediated transduction (Feigner et al. (1987)*Proc. Natl. Acad. Sci. USA* 84:7413-7417), and nucleic acid delivery using high-velocity microprojectiles (Klein et al. (1987) *Nature* 327:70-73).

Suitable host cells for producing AAV virions include microorganisms, yeast cells, insect cells, and mammalian cells, that can be, or have been, used as recipients of a heterologous DNA molecule. The term includes the progeny of the original cell transfected. Thus, a "host cell" as used herein generally refers to a cell transfected with an exogenous DNA sequence. Cells from the stable human cell line, 293 (readily available through, e.g., the American Type Culture Collection under Accession Number ATCC CRL 1573) can be used. For example, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a convenient platform in which to produce AAV virions. Methods of producing an AAV virion in insect cells are known in the art, and can be used to produce a subject AAV virion. See, e.g., U.S. Patent Publication No. 2009/0203071; U.S. Pat. No. 7,271,002; and Chen (2008) *Mol. Ther.* 16:924. The AAV virion or AAV vector can be packaged into an infectious virion or virus particle, by any of the methods described herein or known in the art.

In another aspect, provided herein is a kit comprising packaging material and one or more components of the present invention. A kit typically includes a label or packaging insert including a description of the components or instructions for use in vitro, in vivo, or ex vivo, of the components therein. A kit can contain a collection of such components, e.g., an AAV vector or AAV virion described herein, a sgRNA, a Cas9 polypeptide (or a polynucleotide encoding the Cas9 polypeptide, or a combination thereof. In some cases, the kit includes one or more components comprising one or more AAV vectors or AAV virions described herein, and a Cas9 ribonucleoprotein.

Methods for Using CRISPR/Cas9-Mediated Homologous Recombination of Multiple Donor Vectors Methods described herein can be used to introduce a target polynucleotide (e.g., one or more transgene, expression cassettes, etc.) into a target genetic locus in a cell such as a primary cell obtained from a subject. In some embodiments, the subject can have a genetic disease. The method includes introducing into the cell a first targeting AAV vector, a second targeting AAV vector, a target locus-specific sgRNA, and either a Cas9 polypeptide or a polynucleotide encoding the Cas9 polypeptide or a Cas9 ribonucleoprotein. In some cases, the cell is removed from the subject; the components of the system described herein are delivered to the cell, and the genome-edited cell is administered or returned to the subject. In other cases, the components of the system described herein are delivered in vivo to the subject by direct administration to the subject.

In some embodiments, the target locus-specific sgRNA and the Cas9 polypeptide (or the polynucleotide encoding the Cas9 polypeptide), or the Cas9 ribonucleoprotein are introduced into the cell at the same time as the targeting AAV vectors. Any method for introducing polynucleotides, polypeptides, and ribonucleoproteins into cells can be used including, but not limited to, electroporation, nucleofection, transfection, lipofection, transduction, microinjection, electroinjection, electrofusion, nanoparticle bombardment, transformation, conjugation, and the like.

The first targeting AAV vector and second targeting AAV vector can be introduced to the cell simultaneously or sequentially. In some embodiments, the first targeting AAV vector and the second second targeting AAV vector are delivered to the cell at the same time.

After the target polynucleotide has been correctly integrated into the target genetic locus, the resulting cell can be administered to the subject.

Methods described herein can also be used for treating a genetic disease in a subject, e.g., a human subject. A subject in need thereof can be administered a first targeting AAV vector, a second targeting AAV vector, a target locus-specific sgRNA, and either a Cas9 polypeptide or a polynucleotide encoding the Cas9 polypeptide or a Cas9 ribonucleoprotein to the subject. In some embodiments, all the components of the method are administered to the subject simultaneously. In other embodiments, all the components of the method are administered to the subject sequentially in any order.

In some cases, the first targeting AAV vector and second targeting AAV vector can be administered to the subject simultaneously or sequentially. In some embodiments, the first targeting AAV vector and the second second targeting AAV vector are administered at the same time.

AAV vectors or AAV virions can be administered systemically, regionally or locally, or by any route, for example, by injection, infusion, orally (e.g., ingestion or inhalation), or topically (e.g., transdermally). Such delivery and administration include intravenously, intramuscularly, intraperitoneally, intradermally, subcutaneously, intracavity, intracranially, transdermally (topical), parenterally, e.g. transmucosally or rectally. Exemplary administration and delivery routes include intravenous (i.v.), intraperitoneal (i.p.), intraarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, and intralymphatic.

In some embodiments, a therapeutically effective amount of a target polynucleotide packaged by the AAV vector or virion is an amount that, when administered to a subject in one or more doses, is effective to slow the progression of the disease or disorder in the subject, or is effective to ameliorate symptoms. For example, a therapeutically effective amount of a target polynucleotide packaged by the AAV vector or virion can be an amount that, when administered to an individual in one or more doses, is effective to slow the progression of the disease by at least about 15%, at least about 20%, at least about 25%, at least about 30%, at least about 40%, at least about 50%, at least about 60%, at least about 70%, at least about 80%, or more than about 80%, compared to the progression of the disease in the absence of treatment with the target polynucleotide packaged by the AAV virion.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Improvement of clinical symptoms can also be monitored by one or more methods known to the art, and used as an indication of therapeutic effectiveness. Clinical symptoms may also be monitored by anatomical or physiological means. In some embodiments, a therapeutic molecule packaged by the AAV vector or virion, when introduced into a subject, provides for production of the target gene product for a period of time of from about 2 days to about 6 months, e.g., from about 2 days to about 7 days, from about 1 week to about 4 weeks, from about 1 month to about 2 months, or from about 2 months to about 6 months. In some embodiments, a therapeutic molecule packaged by the AAV vector or virion, when introduced into a subject, provides for production of the target gene product for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years.

Multiple doses of an AAV vector or virus can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject AAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the target polynucleotide or expression product (protein), and the stability of the protein expressed. One skilled in the art can readily determine a virion dose range to treat a patient having a particular disease or disorder based on the aforementioned factors, as well as other factors. Generally, doses will range from at least about, or more, for example, about $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect.

An effective amount or a sufficient amount can, but need not be, provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol.

An effective amount or a sufficient amount need not be effective in each and every subject treated, or a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

With regard to a disease or symptom thereof, or an underlying cellular response, a detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

DETAILED DESCRIPTION OF EMBODIMENTS

Provided herein is a method of gene correction using a split strategy (e.g., two AAV vector strategy) for integration of a large gene cassette (e.g., large transgene) into a target locus. The two AAV vectors undergo sequential homologous recombination at the target locus. In some embodiments, the method, system, or kit of the present invention comprises a target locus-specific sgRNA, a correction template(s) (e.g., a universal template), and a delivery strategy (e.g., an AAV system). In some embodiments, the target locus-specific sgRNA is a CCR5 sgRNA. In other embodiments, the target locus-specific sgRNA is a CFTR sgRNA. In some embodiments, two correction templates are used. For instance, the universal template can be delivered to the cell of interest using two AAV donors. In some embodiments of a CFTR transgene, a first AAV virus comprises 400 base pair (bp) left homology arm (LHA) consisting of 400 bp upstream of the double-stranded break (DSB) site, the first 2883 bp of the CFTR cDNA sequence, CF-Universal sgRNA (CFTR sgRNA) sequence (SEQ ID NO: 14), 400 bp stuffer DNA and 400 base pair (bp) right homology arm (RHA) consisting of 400 bp upstream of the original double-stranded break (DSB) site (see, SEQ ID NO: 15).

In some embodiments of a CFTR transgene, a second AAV virus comprises the last 400 bp of the CFTR cDNA sequence as the second left homology arm (LHA-II), the second 1560 bp of the CFTR cDNA sequence, a BGH poly-A tail, a PGK promoter, a truncated-CD19 (or other cell marker), a SV40 poly-A tail, and stuffer DNA from the first AAV virus as the second right homology arm (RHA-II) (see, SEQ ID NO: 16).

Provided herein are kits for performing the methods described herein. In some embodiments, the kit comprises (1) a first targeting AAV vector comprising a single guide RNA (sgRNA) target site with a protospacer-adjacent motif (PAM), a first donor template, a 5' homology arm that is homologous to a first portion of the target locus, and a 3' homology arm that is homologous to a second portion of the target locus that is not overlapping or substantially not overlapping with the first portion of the target locus; (2) a second targeting AAV vector comprising a second donor template, a 5' homology arm that is homologous to a first portion of the first donor template, a 3' homology arm that is homologous to a second portion of the first targeting AAV vector; (3) a target locus-specific sgRNA; and (4) a CRISPR-associated protein 9 (Cas9) polypeptide or a polynucleotide encoding the Cas9 polypeptide. In some embodiments, the sgRNA target site is recognized by a target locus-specific sgRNA, wherein the first donor template comprises a first nucleotide sequence of the target polynucleotide. In some embodiments, the first portion of the first donor template and the second portion of the first targeting AAV vector are not overlapping, the second donor template comprises a second nucleotide sequence of the target polynucleotide, and the nucleotide sequence of the target polynucleotide is split between the first donor template and the second donor template.

In certain embodiments, the target locus-specific sgRNA comprises one or more modified nucleotides such as those described herein. In some embodiments, the target locus-specific sgRNA is a CCR5 sgRNA with the modified nucleotides (SEQ ID NO: 1). In some embodiments, the target locus-specific sgRNA is a CFTR sgRNA (SEQ ID NO: 14).

In particular embodiments, the kit also comprises a reagent (e.g., a buffer, a stabilization buffer, a dilution buffer, a reconstitution buffer, etc.) for reconstituting and/or diluting a targeting AAV vector. In particular embodiments, the kit also comprises a cell such as, but not limited to, an immune cell, a muscle cell, a liver cell, a skin cell, a retinal cell, an airway cell, a lung cell, a stem cell (e.g., a pluripotent stem cell, an adult stem cell, an induced pluripotent stem cell, etc.), a proliferating cell, a progenitor cell, and a precursor cell.

In some instances, the kit also includes instructions for practicing the method.

EXAMPLES

Example 1: CRISPR-Mediated Integration of Large Gene Cassettes Using AAV Donor Vectors Detailed description of the Example can be found in Bak and Porteus, Cell Reports, 2017:20, 750-756, which is expressly incorporated herein by reference in its entirety, with particular reference to the results, discussion, experimental procedures, figures, legends, and references therein.

The CRISPR/Cas9 system has recently been shown to facilitate high levels of precise genome editing using adeno associated viral (AAV) vectors to serve as donor template DNA during homologous recombination (HR). However, the maximum AAV packaging capacity of ~4.5 kilobases limits the size of the donor. Provided herein are systems and methods to overcome this constraint by showing that two co-transduced AAV vectors can serve as donors during consecutive HR events for integration of large transgenes. Importantly, the method involves a single-step procedure applicable to primary cells with relevance to therapeutic genome editing. The method was used in primary human T cells and CD34+ hematopoietic stem and progenitor cells to site-specifically integrate an expression cassette that as a single donor vector would otherwise amount to a total of 6.5 kilobases. This approach provides an efficient way to integrate large transgene cassettes into the genomes of primary human cells using HR-mediated genome editing with AAV vectors.

I. Introduction

Precise genome editing can be accomplished using designer nucleases (e.g. ZFNs and TALENs) or RNA-guided nucleases (e.g., CRISPR/Cas9), which create site-specific double-strand breaks (DSBs) that stimulate homologous recombination (HR) when supplied with a homologous donor DNA template. This method can facilitate targeted integration of transgenes for gene therapy or studies of gene function.

Viral vectors derived from the non-pathogenic, single-stranded DNA virus, adeno-associated virus (AAV), can transduce both dividing and non-dividing cells and have recently been effectively used as donor vectors for HR both in vitro and in vivo (Sather et al., 2015, Wang et al., 2015, DeWitt et al., 2016, Yang et al., 2016, Yin et al., 2016, Dever et al., 2016, De Ravin et al., 2017). However, despite decades of research, the 4.5 kb packaging capacity of recombinant AAV (rAAV) vectors has not been successfully extended, though strategies that enable episomal expression of transgenes that exceed the packaging capacity have been devised (Grieger and Samulski, 2005, Chamberlain et al., 2016, Nakai et al., 2000, Sun et al., 2000, Halbert et al., 2002). The constraint in vector capacity limits applications of genome editing with AAV donor vectors since the homology arms required for efficient HR add a minimum of 2×0.4 kilobases (kb) to the vector (Hendel et al., 2014), leaving 3.7 kb for promoter, polyadenylation signal, and transgene. Several genetic diseases involve mutations in genes that exceed this limit, such as Duchenne Muscular Dystrophy (dystrophin: 11 kb), hemophilia A (Factor VIII: 7 kb), and Cystic Fibrosis (CFTR: 4.4 kb). If required, posttranscriptional regulatory elements would add further to the vector, and depending on gene size the use of multi-cistronic cassettes would be limited.

Provided herein is a CRISPR/Cas9-based methodology that enables site-specific integration of large transgenes that are split between two AAV donor vectors, and show that this process occurs at high frequencies in the K562 cell line, primary human T cells, and in CD34+ hematopoietic stem and progenitor cells (HSPCs) with long-term repopulation capacity.

II. Results

Figure 1A:
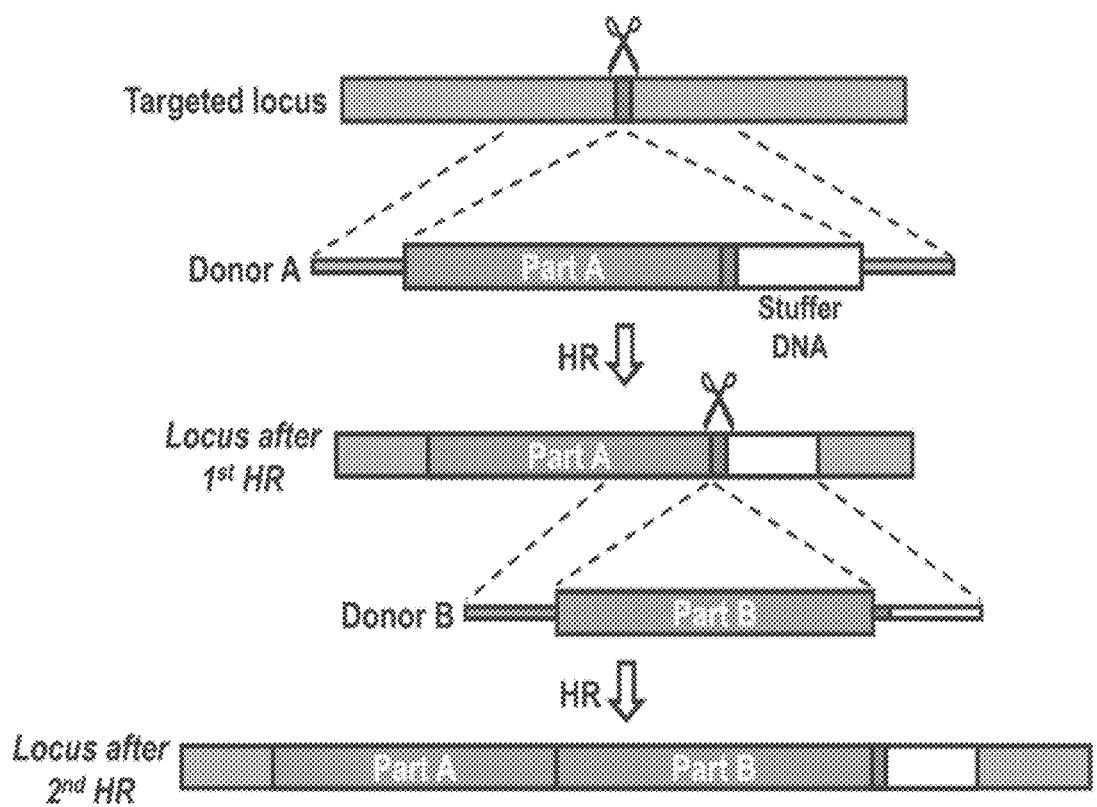
FIGS. 1A and 1B illustrate sequential homologous recombination of two AAV6 donors with a split GFP gene in K562 cells.

Since HR is a seamless process, it was envisaged that two parts of a large transgene could be fused together by consecutive HR events using two different AAV donor vectors (FIG. 1A). Donor A integrates 'Part A' of the transgene and a key feature of Donor A is that it contains the same sgRNA target site that mediated its integration so that the site is reconstituted in the genome after integration. 400 bp stuffer DNA after the target site serves as homology arm for donor B to avoid using the same homology arm as donor A, which could enable donor B to be integrated instead of donor A during the first HR step using only a single homology arm as has previously been reported (Basiri et al., 2017, Lombardo et al., 2007). Homologous recombination of donor B fuses 'Part B' of the transgene to 'Part A' using the introduced sgRNA target site.

Figure 1B:
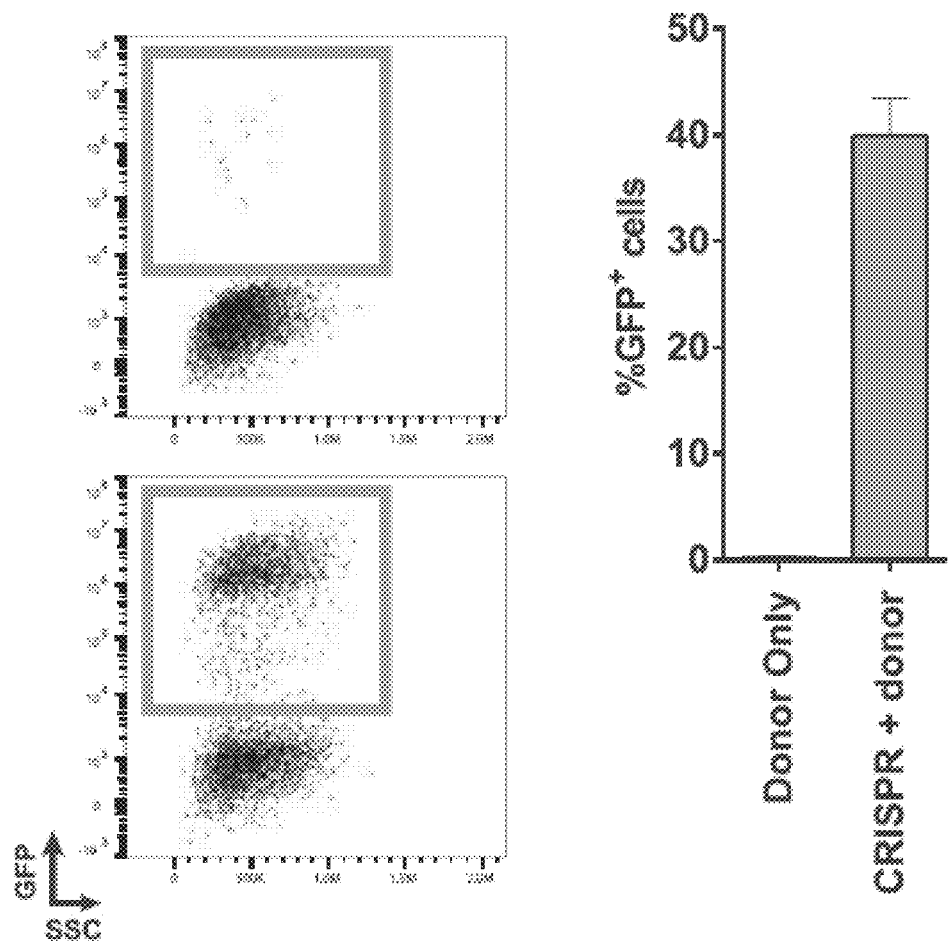
Figure 5:
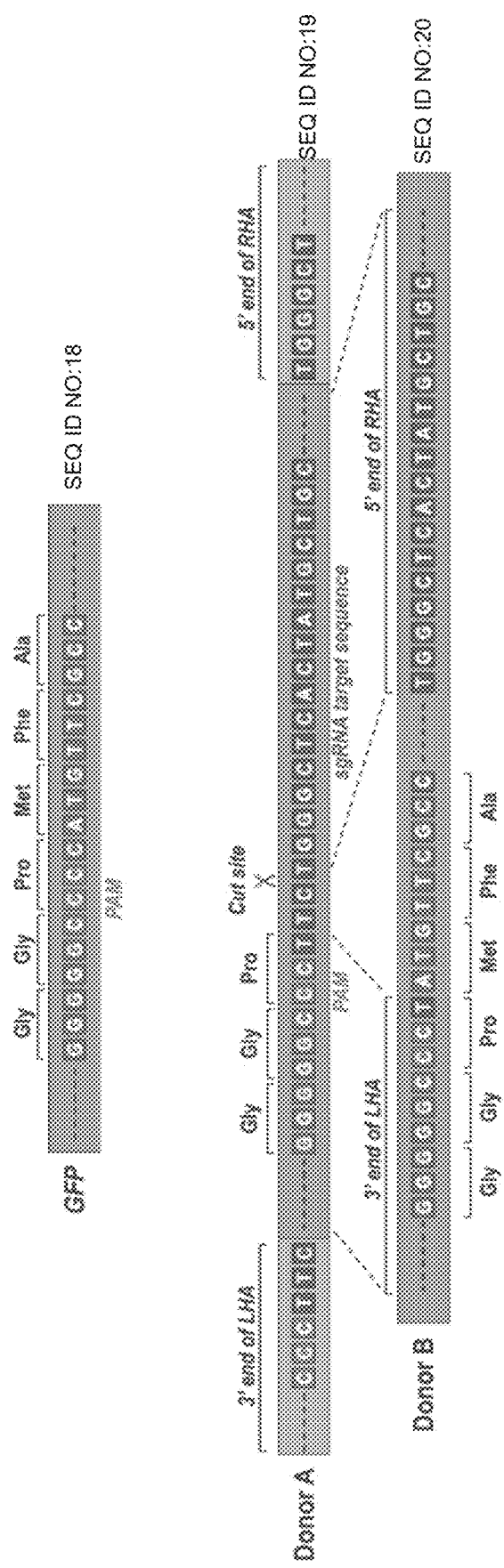
FIG. 5 provides details of the split GFP donor design. GFP was split at a PAM site for the CCR5 sgRNA (NGG=GGG). Note that the PAM sequence is located on the non-coding strand and that the sequence of the coding strand is depicted. Codons are depicted above nucleotides. The endogenous CCR5 sgRNA target site is depicted with the PAM in red and the 20 nt target site in purple. Donor A carries the left and right homology arms (LHA and RHA) which are split directly at the Cas9 cut site (depicted with scissors) between nucleotide 17 and 18 of the CCR5 sgRNA target site. Donor A carries a truncated GFP sequence that stops after a PAM site identified in the GFP gene. Directly after the PAM, the 20 nt target site for the same CCR5 sgRNA is introduced. Note that the last codon (Pro) of the truncated GFP sequence is maintained with the fusion to the sgRNA target sequence. Thus, the left homology arm (LHA) of donor B ends right after this proline codon. The right homology arm begins immediately after the Cas9 cut site (scissors). The homology arms flank the remaining part of GFP (and an mCherry expression cassette, see FIG. 4) that upon seamless HR of donor B will reconstitute a functional GFP open reading frame. In principal, there are no sequence requirements for the site at which the transgene is split between the two donors. However, if possible the homology arms of donor B should be located as close to the Cas9 cut site for optimal HR rates. For the same reason, the sgRNA target site in donor A is preferably oriented with the NGG PAM on the non-coding strand. This leaves only a maximum of 6-nt distance between the cut site and the left homology arm in case a stretch of those 6-nt cannot be found at a suitable site to split the transgene.
Figure 6A:
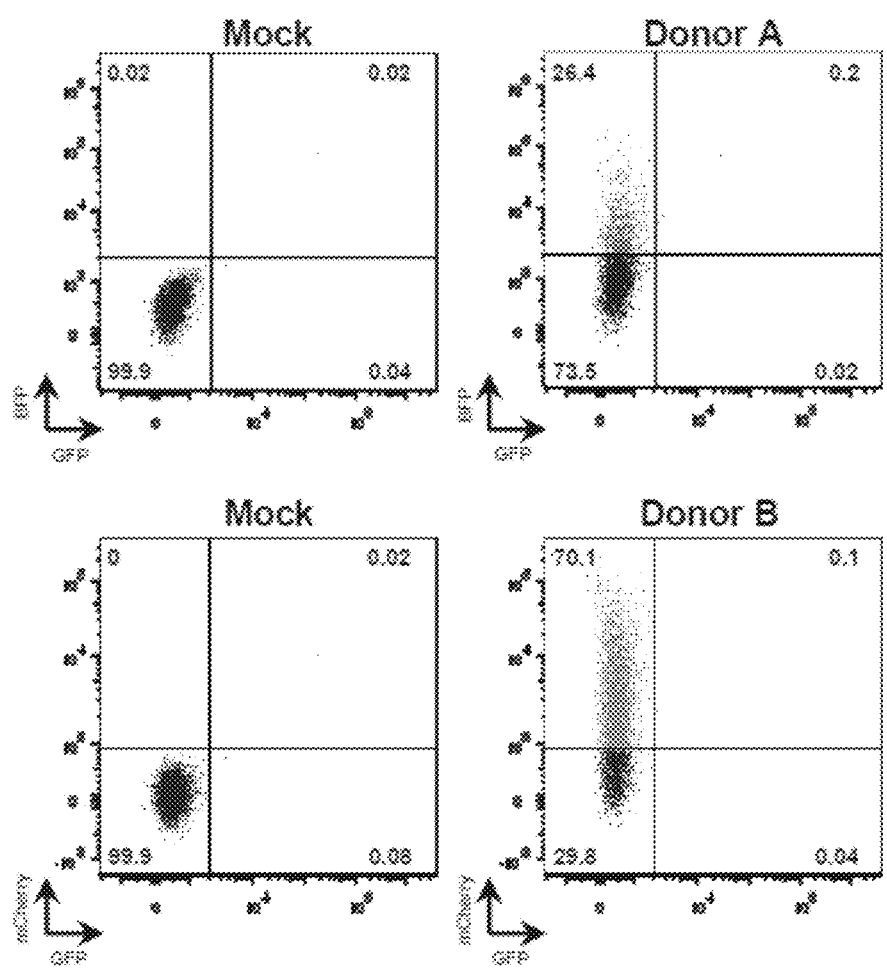
FIGS. 6A-6D show that neither of the two donors of the split GFP system express GFP on their own, only donor A works as a homologous CCR5 donor, and low levels of GFP reconstitution when using plasmid donors. Donor A and donor B of the split GFP system depicted in FIG. 4 were delivered to K562 cells either by plasmid electroporation (FIG. 6A) or AAV6 transduction (FIG. 6B). Representative FACS plots show BFP, mCherry, and GFP fluorescence as measured by flow cytometry four days after delivery and data show that neither donor alone expresses GFP. Donor A and donor B plasmids were electroporated into K562 cells with or without Cas9 mRNA and CCR5 sgRNA (CRISPR). Representative FACS plots show BFP and mCherry expression measured by flow cytometry 16 days after electroporation when episomal plasmid DNA was diluted out (FIG. 6C). Data show that only donor A can serve as donor template for homologous recombination at CCR5 (40.1% of cells stably expressing BFP) while low integration rates of donor B was observed (2.8% of cells stably expressing mCherry), which are consistent with rates observed for random integration in K562 cells. K562 cells were electroporated with donor A and donor B plasmids with or without Cas9 mRNA and CCR5 sgRNA (CRISPR). Representative FACS plots show GFP expression measured 14 days after electroporation by flow cytometry with the targeted population gated as the GFP$^{high}$ population (FIG. 6D, left panel, see also FIG. 7). Bar graph (FIG. 6D, right panel) shows data from different biological replicates, N=7.
Figure 6B:
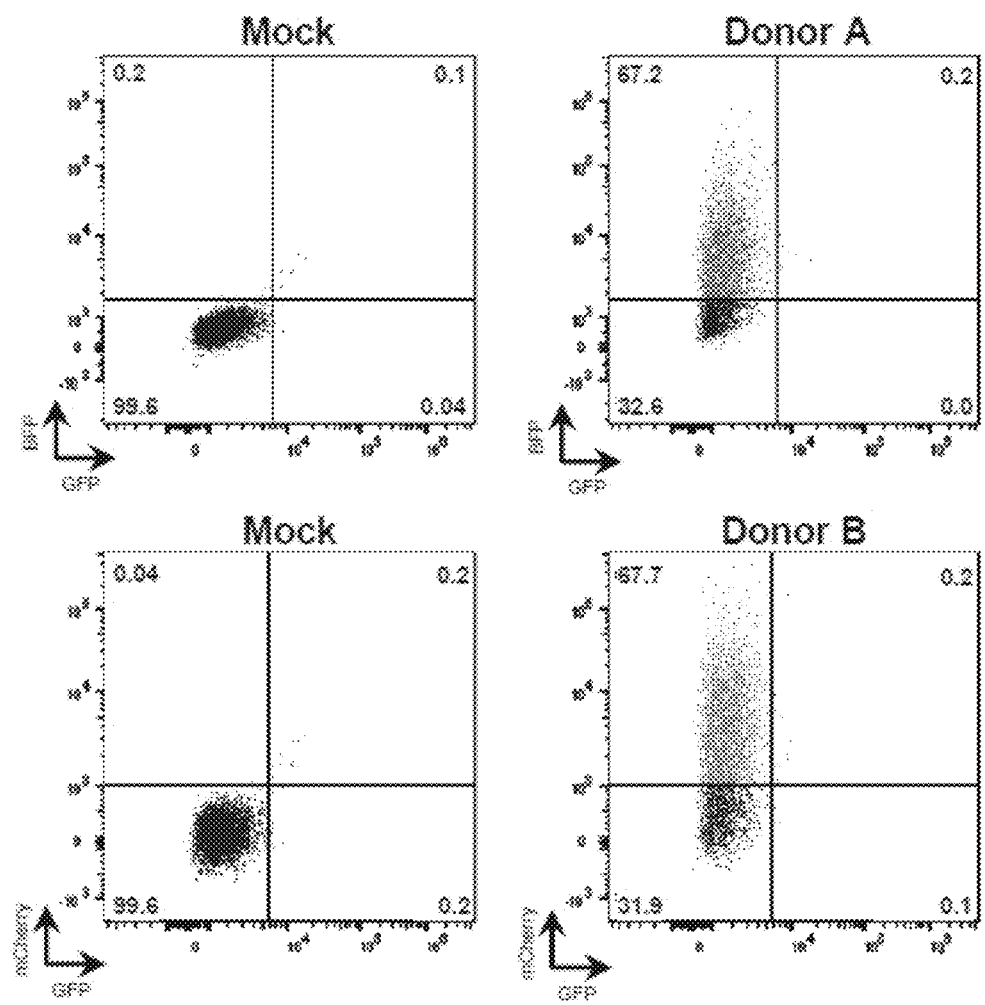
Figure 6C:
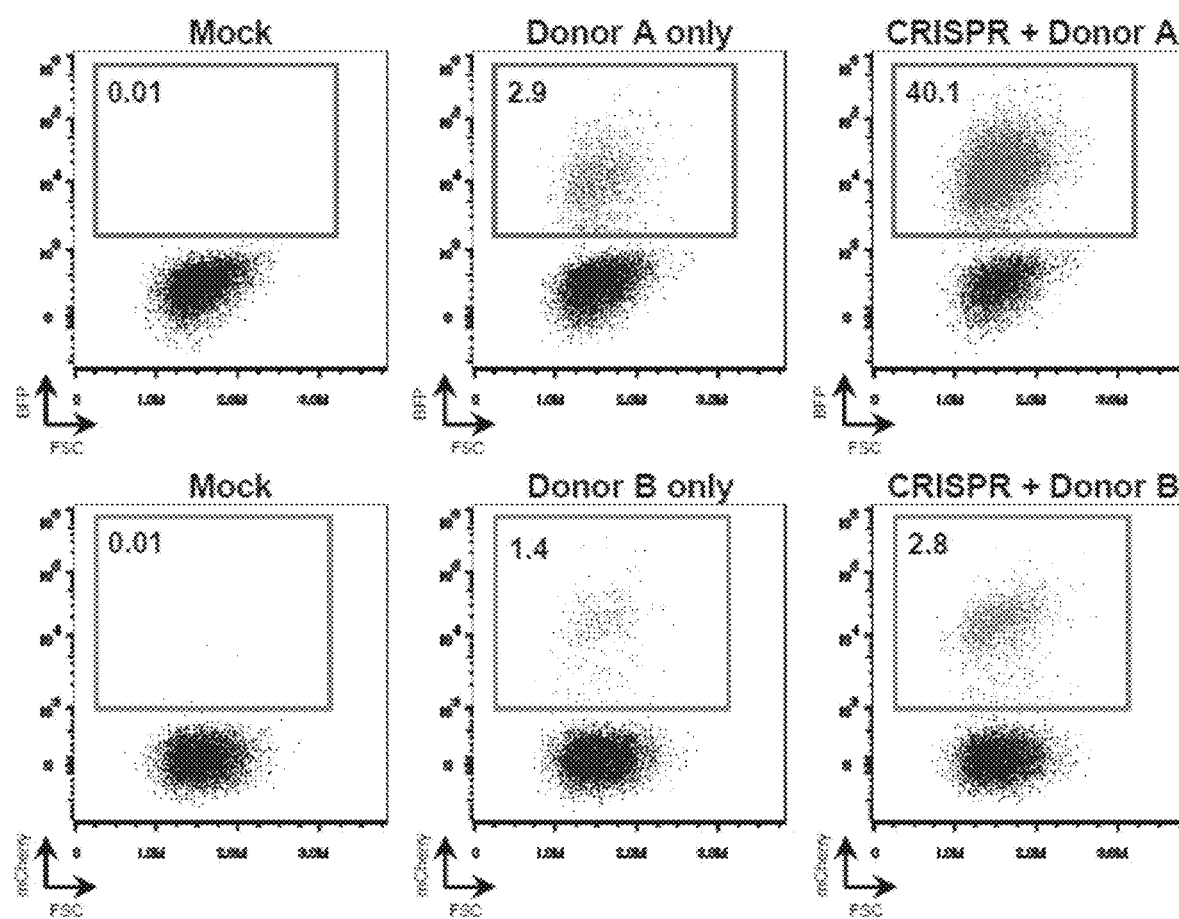
Figure 6D:
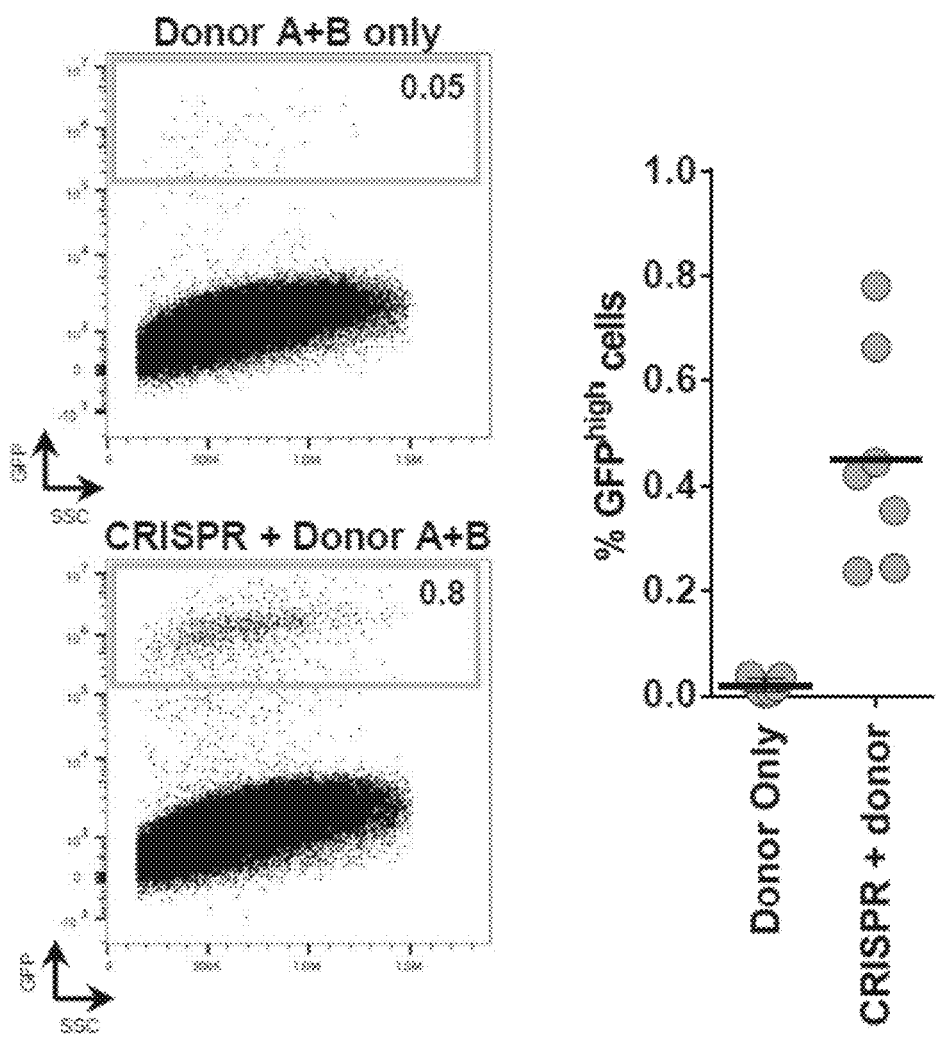
Figure 7:
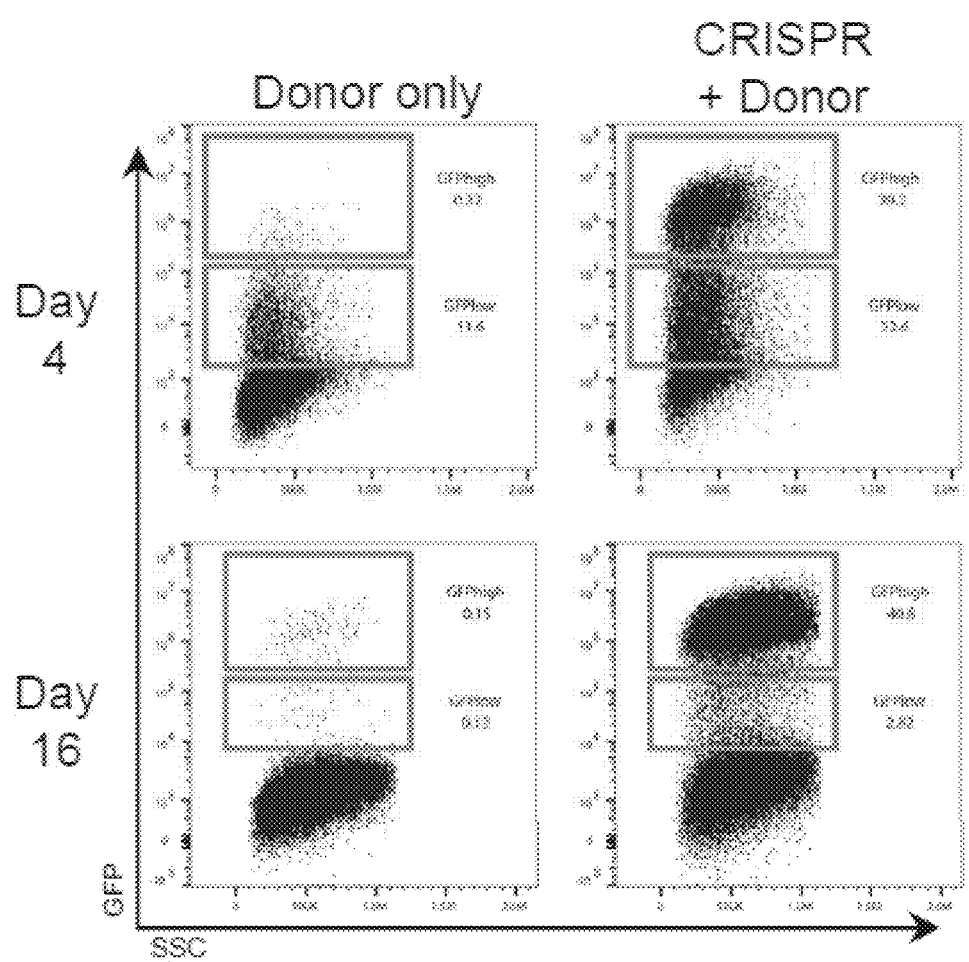
FIG. 7 shows that targeting with the split GFP donor pair leads to transient episomal GFP expression and a stable GFP$^{high}$ population. K562 cells were mock-electroporated or electroporated with Cas9 mRNA and CCR5-targeting sgRNA (CRISPR) and then transduced with the split GFP AAV6 donors. GFP levels were measured by flow cytometry 4 and 16 days after electroporation.
Figure 8A:
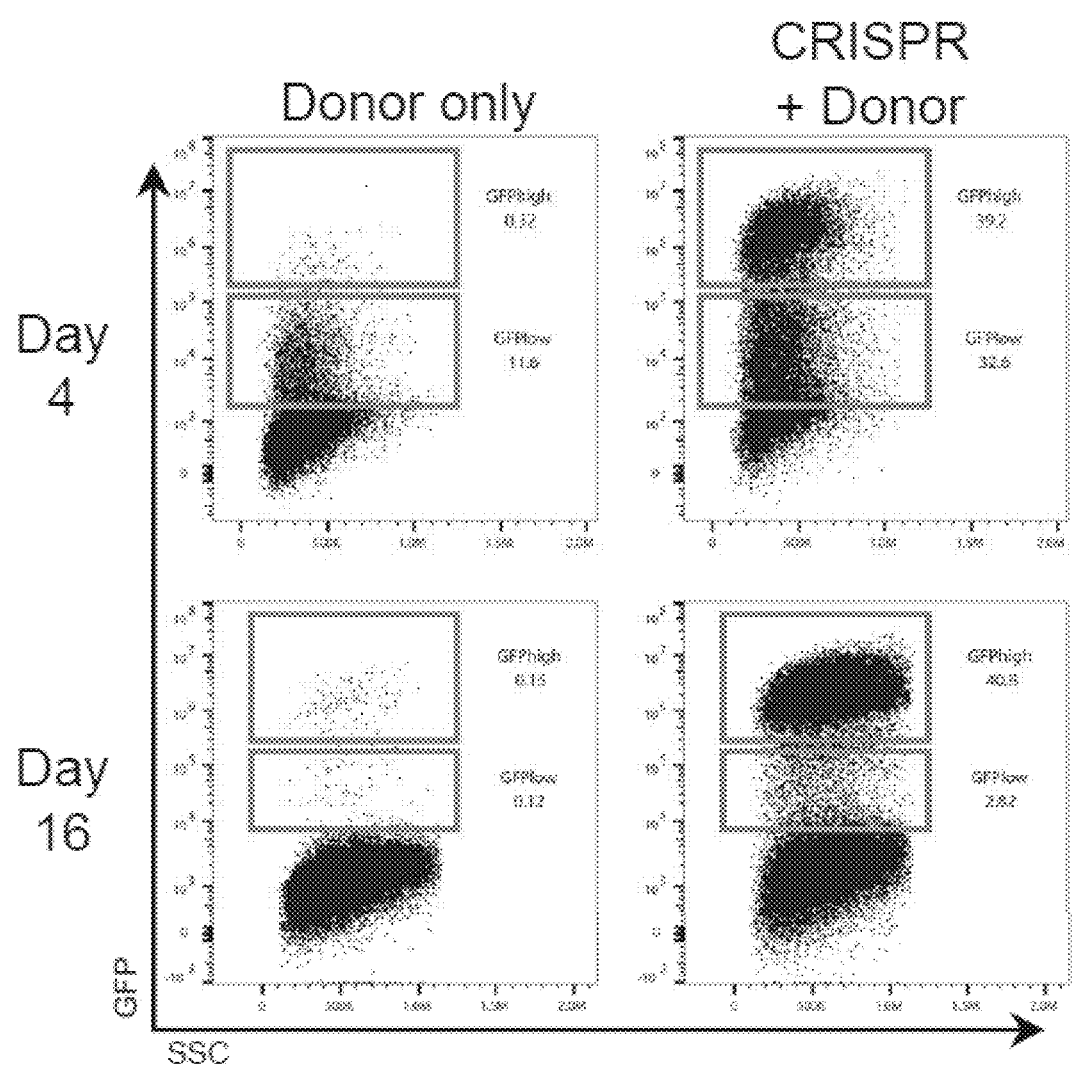
FIGS. 8A-8C show that targeting with the split GFP donor pair leads to transient episomal GFP expression and a stable GFPhigh population, which is also mCherry+ and BFP+. Related to FIGS. 2A-2C.
Figure 8B:
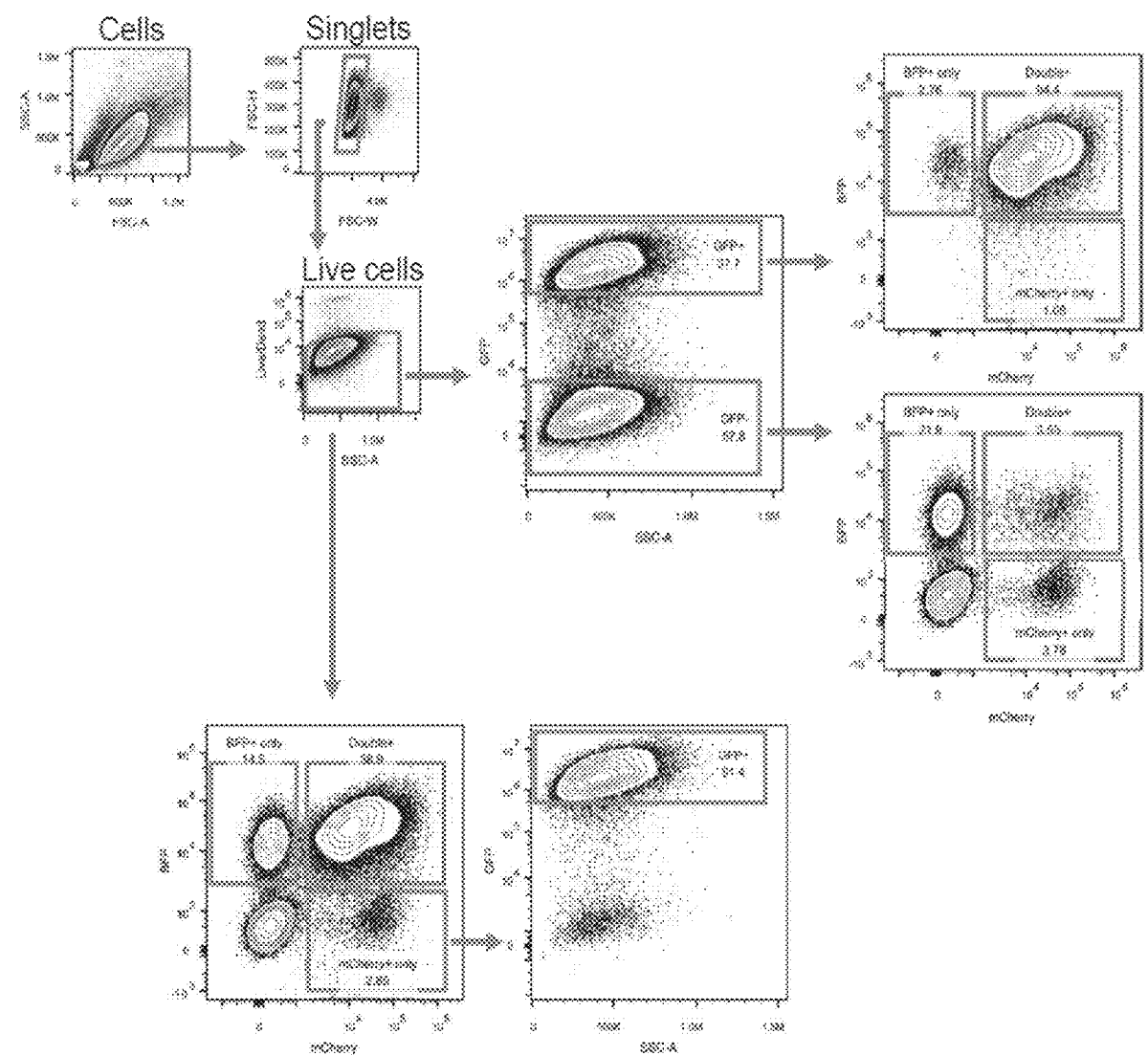
Figure 8C:
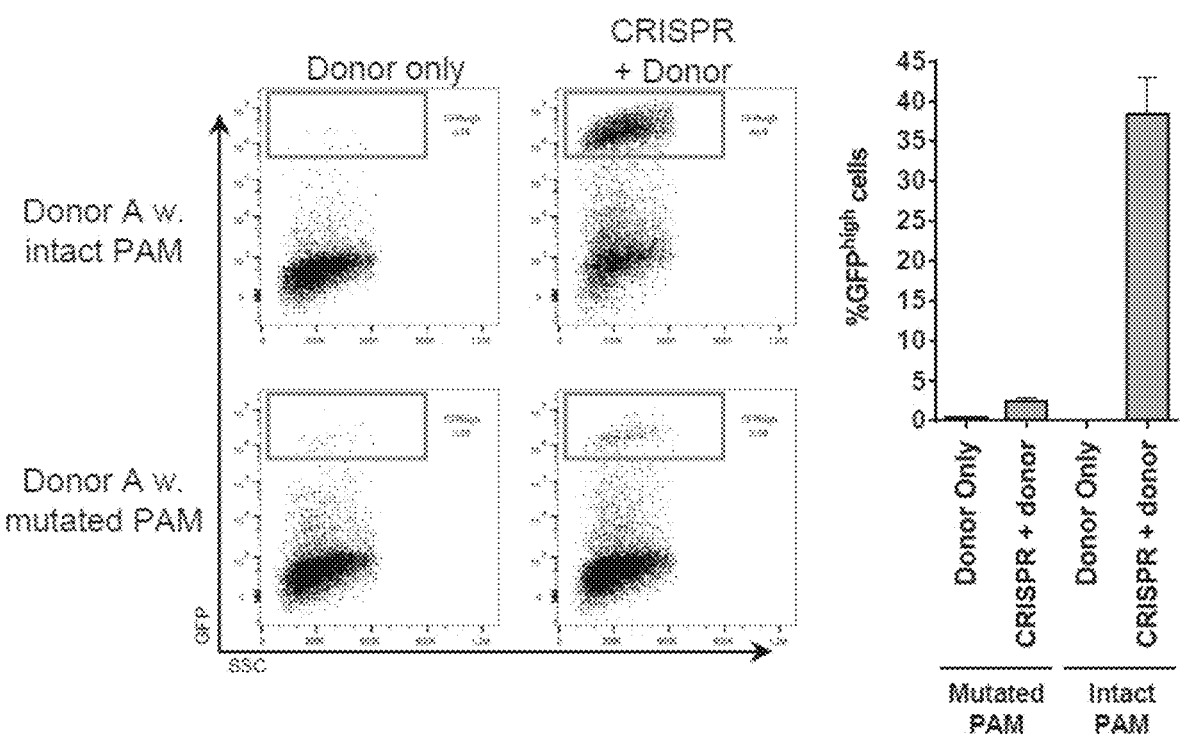

As a first proof of principle of this approach, a donor pair targeting the proposed safe harbor locus CCR5 was designed, where GFP was split between two donors designed as described above (see also FIGS. 4 and 5 for design details). In addition, the two donors each carried different expression cassettes for other fluorescent proteins (BFP and mCherry, respectively) allowing us to confirm that neither donor alone expressed GFP (FIGS. 6A and 6B), and that only donor A could serve as the initial HR donor during CCR5 targeting FIG. 6C). The system was first tested in the K562 cell line by co-electroporation of Cas9 mRNA, CCR5-targeting chemically modified sgRNAs (Hendel et al., 2015), and the two plasmid donors with the split GFP. An average of 0.02% GFP+ cells was observed when only the two plasmid donors were delivered while 0.45% of cells stably expressed GFP when the CRISPR components were co-electroporated (FIG. 6D). Next, the system was tested with the two donors delivered as AAV6 vectors immediately following electroporation. In mock-electroporated cells receiving both AAV6 donors, transient and low expression of GFP was observed at day 4 after electroporation and transduction, which was lost by day 16 (FIGS. 1B and 7). In contrast, electroporation of the CRISPR components and transduction with both AAV6 donors gave rise to a stable population of GFP$^{high}$-expressing cells observed at both day 4 and day 16 in about 40% of the cells (FIGS. 1B and 7), indicative of chromosomal expression of the GFP expression cassette as previously observed (Dever et al., 2016). As expected, the GFP+ population was highly enriched for BFP/mCherry double-positive cells confirming that integration of both donors is required for reconstitution of the GFP expression cassette (FIG. 8).

Figure 2A:
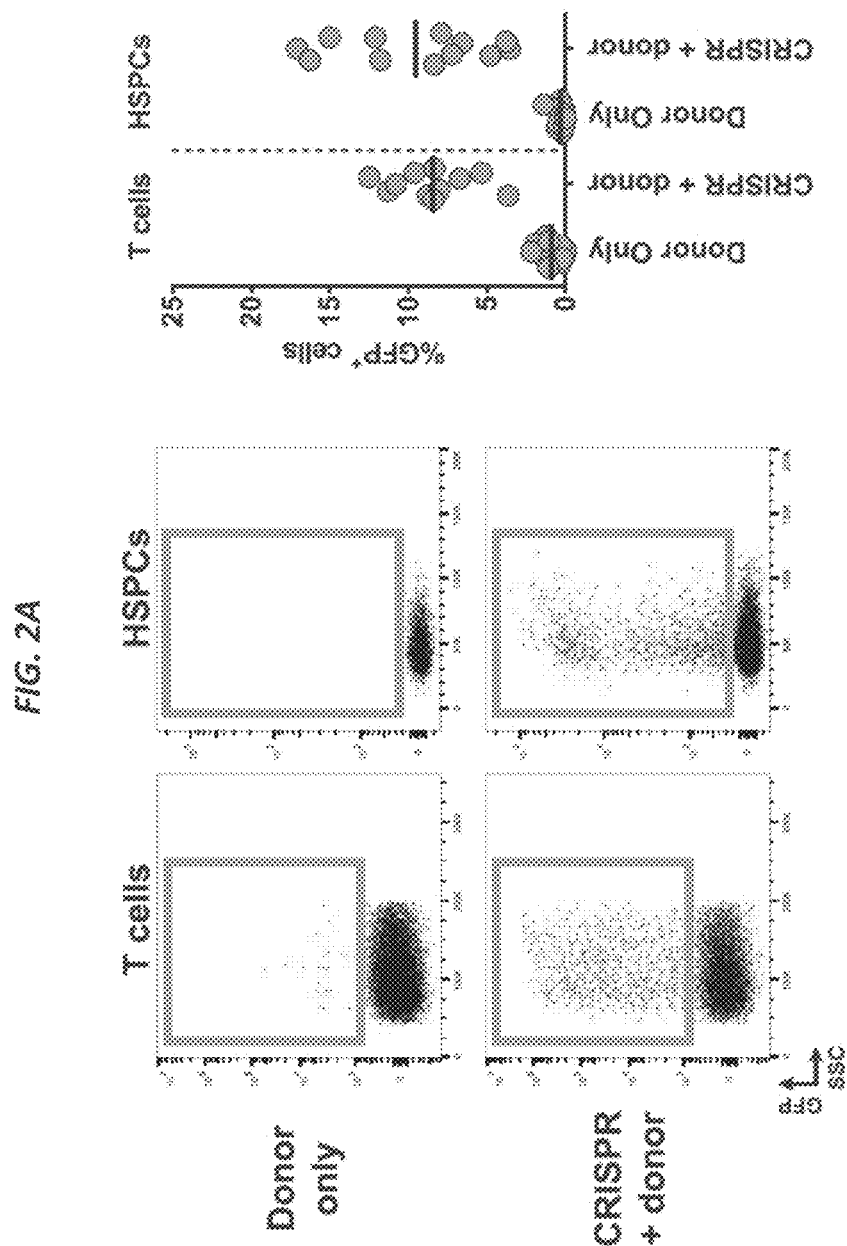
FIGS. 2A-2C illustrate sequential homologous recombination of two AAV6 donors with a split GFP gene in human T cells and CD34+ hematopoietic stem and progenitor cells.
Figure 2B:
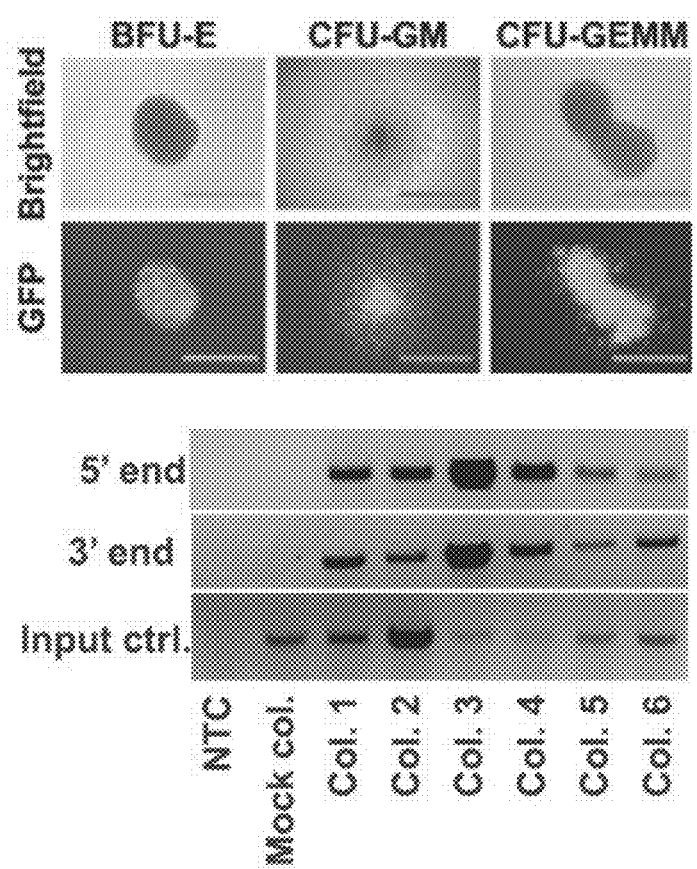
Figure 9A:
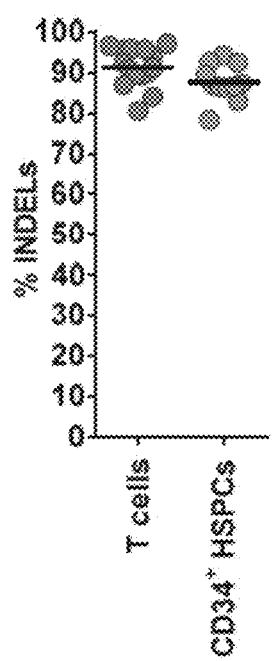
FIGS. 9A-9C depict INDEL rates in T cells and CD34+ HSPCs. T cells and CD34+ HSPCs were electroporated with CCR5 Cas9 (ribonucleoprotein) RNP and genomic DNA was extracted after four days. The targeted CCR5 locus was PCR-amplified, amplicons were Sanger-sequenced, and INDEL rates were analyzed using TIDE (Tracking of Indels by Decomposition) (FIG. 9A). Bars represent means, N=15 (T cells from 15 different buffy coat donors) and N=11 (CD34+ HSPCs from 11 different umbilical cords). The PCR amplicons derived from genomic DNA extracted from RNP-electroporated T cells were TOPO-cloned, transformed into *E. coli* and a total of 160 individual colonies (representing different CCR5 alleles) were sequenced. The sequences were aligned to the CCR5 sequence of unedited cells and frequencies of total INDELs and open reading frame-disruptive INDELs are plotted (FIG. 9B). Bars represent means, N=6 (T cells from 6 different buffy coat donors). Representative FACS plots from Mock and RNP-electroporated T cells stained for CCR5 surface expression four days after electroporation (FIG. 9C). The CCR5+ gate was set based on an isotype antibody control.
Figure 9B:
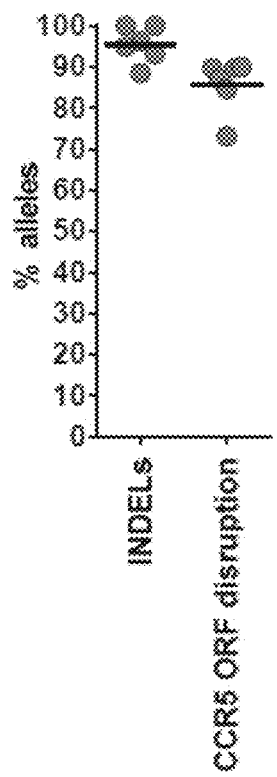
Figure 9C:
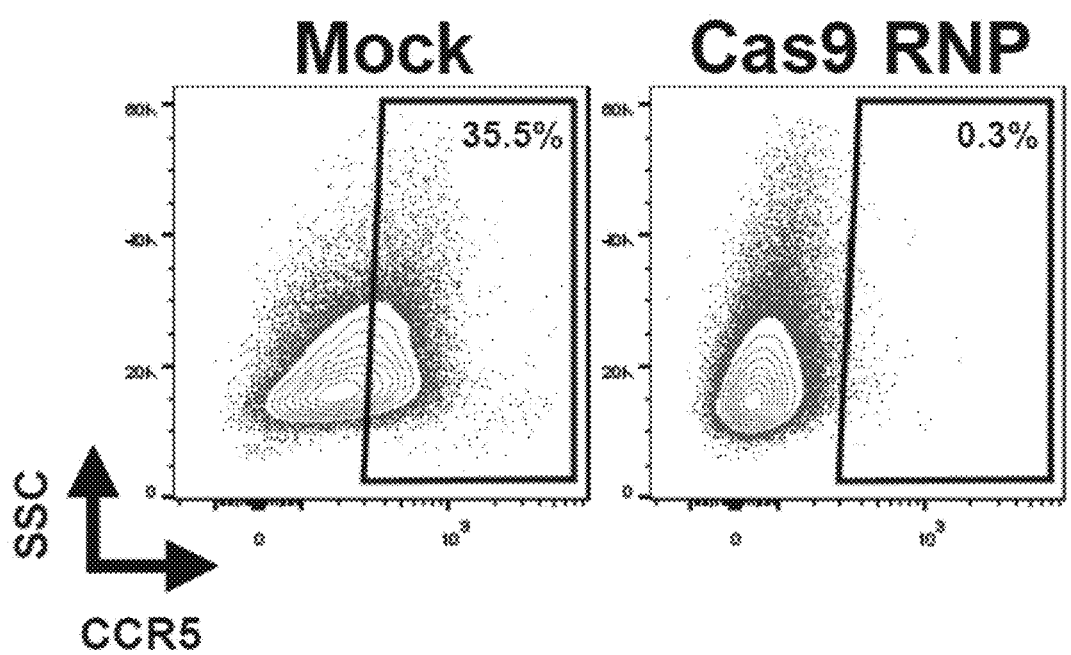
Figure 10:
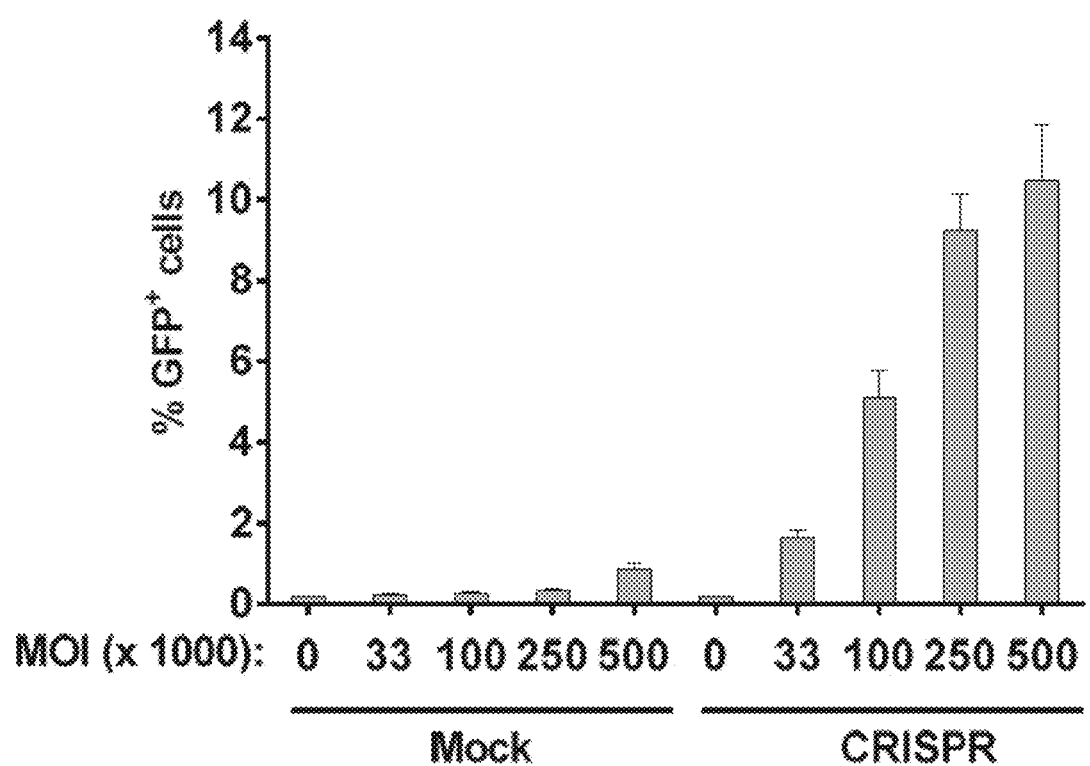
FIG. 10 provides targeting rates with increasing MOIs of the split GFP AAV6 donor pair in primary human T cells. Primary human T cells were stimulated for three days and then electroporated with CCR5 Cas9 RNP (CRISPR) or mock-electroporated, and then transduced with increasing MOIs of AAV6 split GFP donors (MOI is per donor). GFP expression was analyzed by flow cytometry after four days. Bars represent mean±SEM, N=4 (T cells from 4 different buffy coat donors).
Figure 11A:
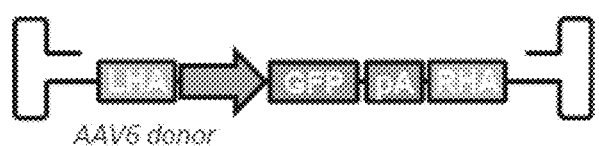
FIGS. 11A-11C illustrate HR rates in T cells and CD34+ HSPCs with a single GFP-encoding AAV6 donor vector. T cells and CD34+ HSPCs were electroporated with CCR5 Cas9 RNP and transduced with a single AAV6 donor vector encoding GFP.
Figure 11B:
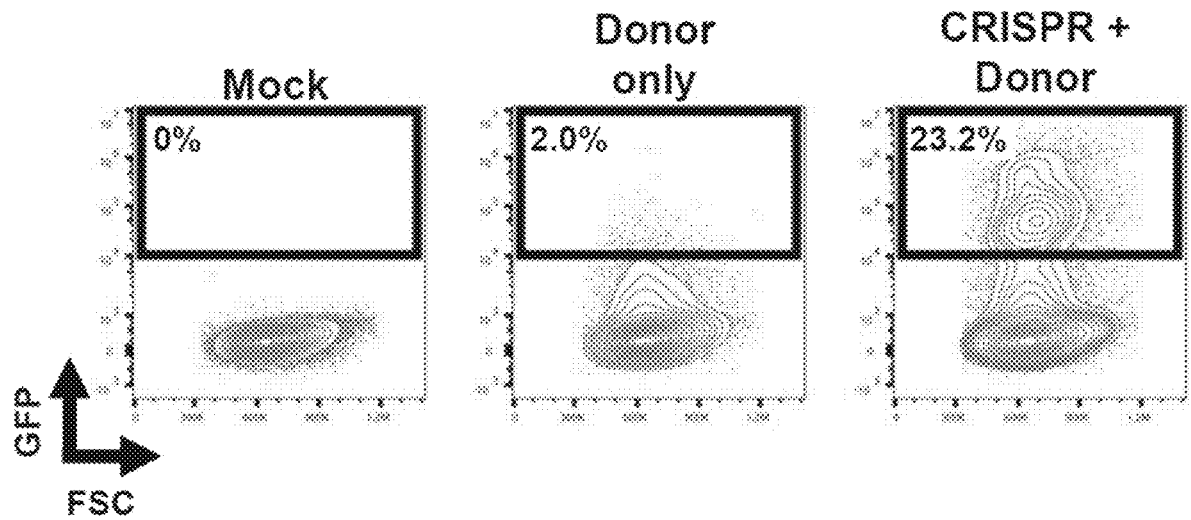
Figure 11C:
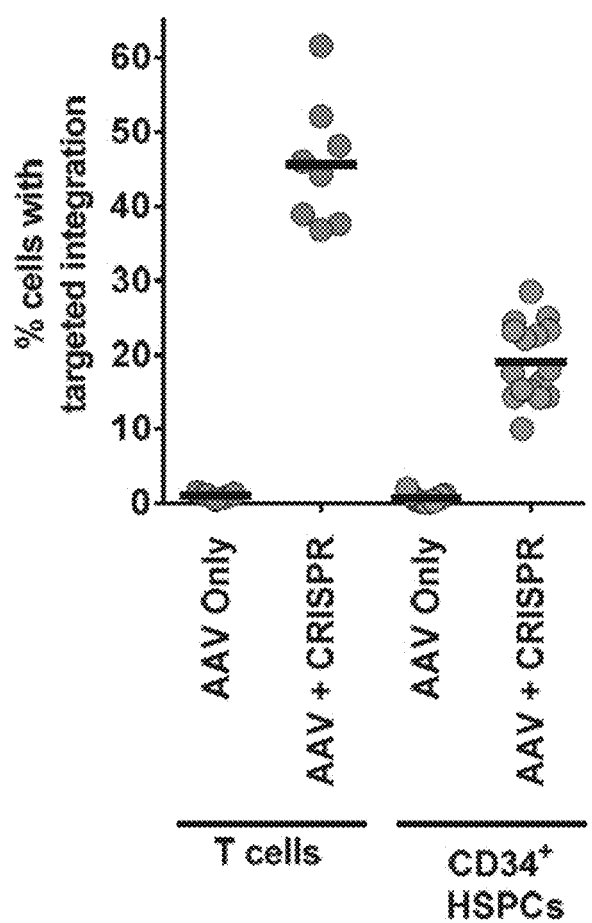
Figure 12:
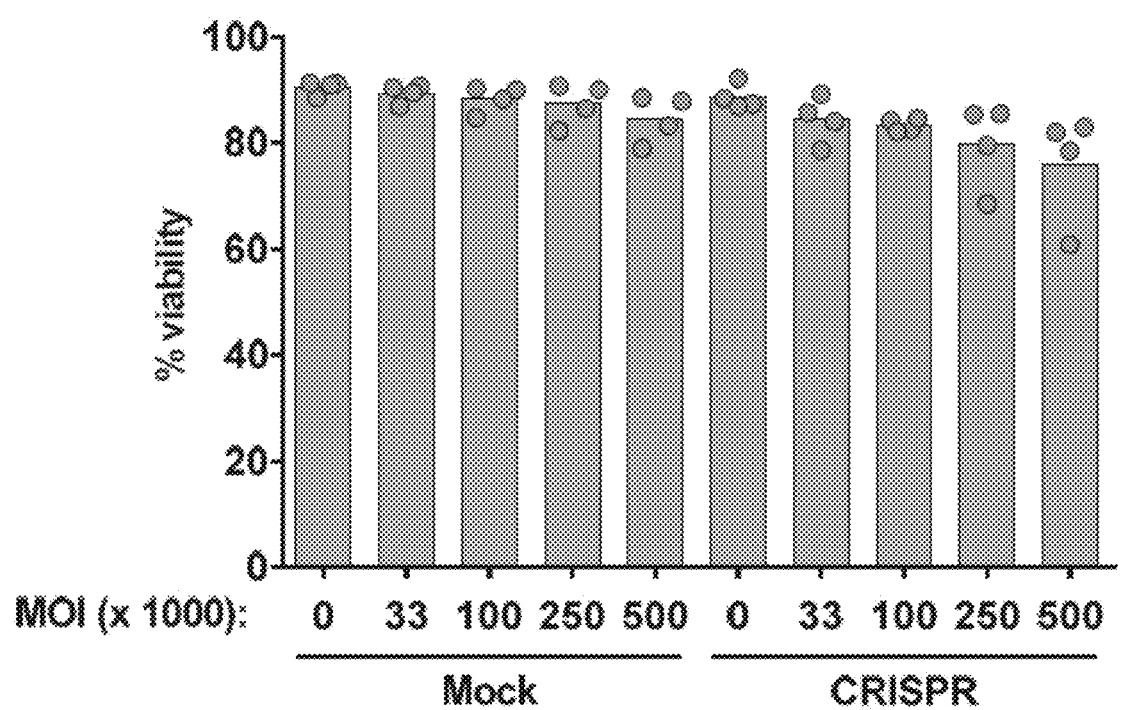
FIG. 12 shows viabilities using the split GFP AAV6 donor pair in primary human T cells. Primary human T cells were stimulated for three days and then electroporated with CCR5 Cas9 RNP (CRISPR) or mock-electroporated and then transduced with increasing MOIs of AAV6 split GFP donors (MOI is per donor). Viable cells were quantified by flow cytometry three days after electroporation and transduction as negative for an amine reactive viability dye and annexin V stain. N=4 (T cells from four different buffy coat donors).
Figure 13:
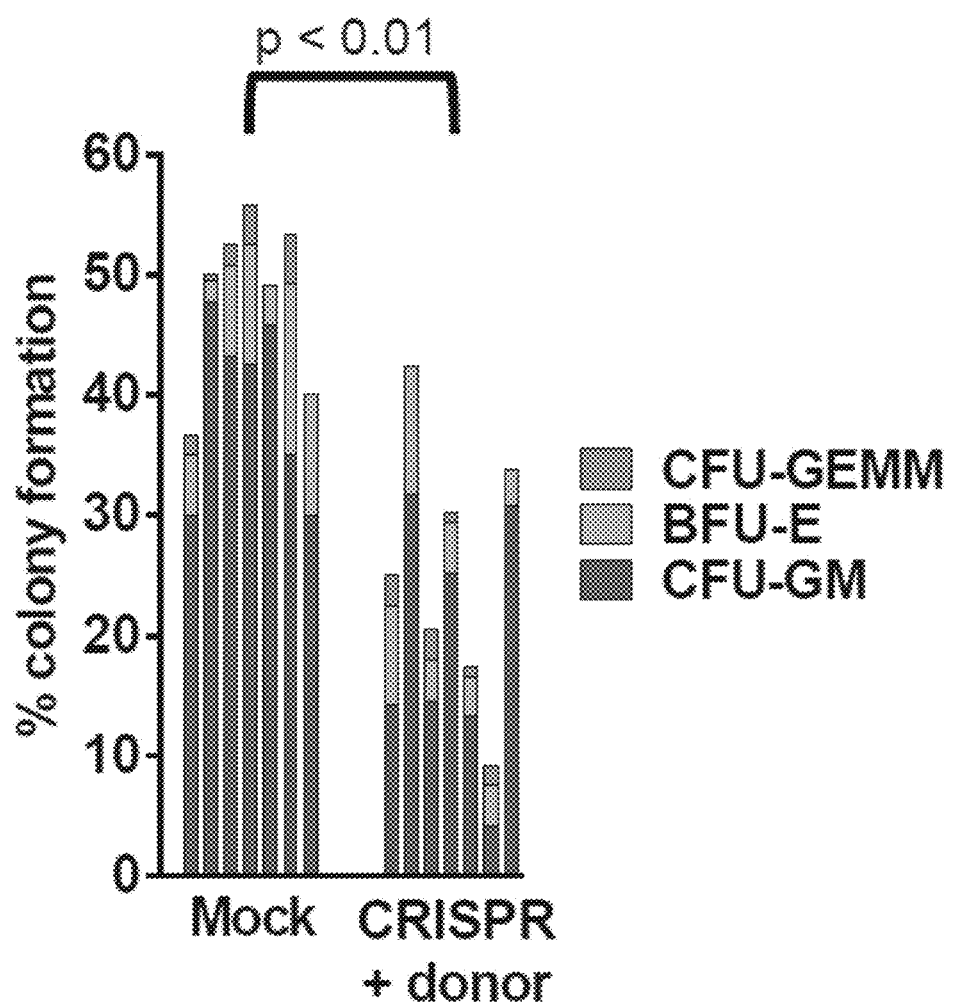
FIG. 13 shows CFU assay on GFP+ HSPCs engineered using the AAV6 split GFP donor pair. Cord blood-derived CD34+ HSPCs were cultured for two days and then electroporated with Cas9 RNP or mock-electroporated. The split GFP AAV6 donor pair was added at an MOI of 2×500,000 and after four days, mock-electroporated or GFP+ cells were single-cell sorted into 96-well plates containing methylcellulose. Formed colonies were counted and scored 14 days after seeding. Colony type distribution showed no difference between the two groups (p≥0.11; student's paired T test) while a 1.9-fold difference in total colony formation was observed (p<0.01; student's paired T test), although with great donor-donor variability. Each bar represents results from a unique cord blood donor, N=7.
Figure 14:
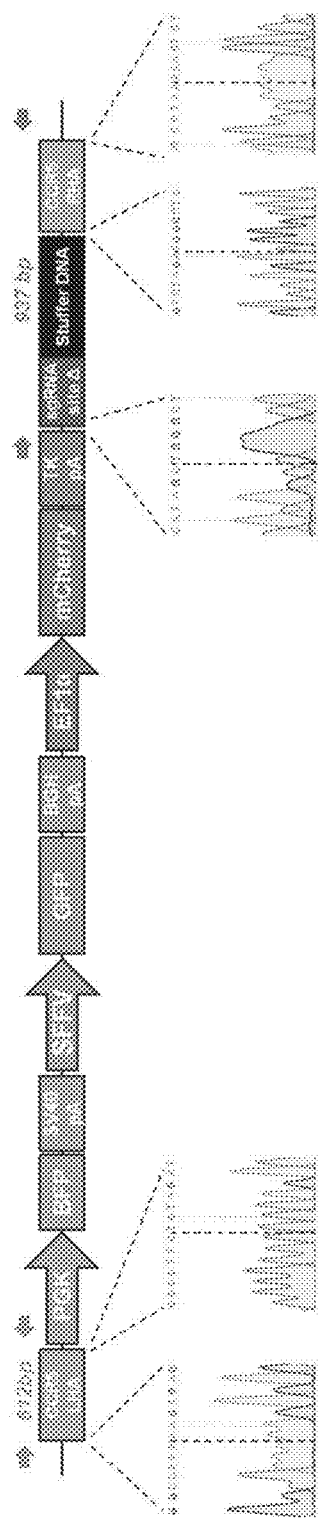
FIG. 14 provides an overview of PCRs confirming targeted integration of both donors of the split GFP system. PCR primers were designed to confirm targeted integration of donor A (blue primers) and donor B (red primers) of the split GFP donor system. Both PCRs are In-Out PCRs where one primer is located in the CCR5 gene outside the region of the homology arm and the other primer is located inside the donor vector insert. PCR fragments from four colonies were gel-purified and sequencing showed seamless HR at all chromosomal junctions (shown with dashed lines) in all four colonies. Representative sequencing chromatograms are shown.

Next this split GFP system was tested in activated primary human T cells and CD34+ HSPCs with the CRISPR system delivered by electroporation of precomplexed Cas9 ribonucleoprotein (RNP) and the two AAV donors delivered immediately after. In cells electroporated with Cas9 RNP but not receiving AAV6 donors, >90% INDEL rates were measured, confirming high activity of the Cas9 RNP system in both cells types (FIG. 9). In mock-electroporated cells receiving only the AAV6 donor pair, the frequency of GFP+ cells was less than 1.0% in both cell types on day 4 after transduction. In contrast, electroporation with Cas9 RNP and transduction with both AAV6 donors gave rise to 8.5% and 9.5% GFP+ T cells and HSPCs, respectively (FIGS. 2A and 10). In comparison, with a single AAV6 donor vector encoding GFP, average targeting rates were 46% and 19% (FIG. 11). Evaluation of cell death and apoptosis in T cells showed little impact of the treatment on viability of the cells (FIG. 12). Next, it was assessed if the sequential HR process was able to target early progenitor cells in the HSPC population capable of forming colonies in methylcellulose. Sorted GFP+ cells formed erythroid, myeloid, and mixed colonies at ratios comparable to mock-electroporated cells, but an overall lower colony formation frequency indicated a lower frequency of progenitor cells in the GFP+ population than in the mock-electroporated population (FIG. 2B, upper panel and FIG. 13). However, the extent of this decrease was donor-dependent. In-Out PCRs, in which one primer is located in the targeted genomic locus outside the region of the homology arm and the other primer located in the donor DNA, was used to confirm on-target integration (FIG. 14). On genomic DNA derived from GFP+ colonies, on-target integration of both Donor A and Donor B was confirmed in all colonies analyzed (41 colonies total), and sequencing confirmed seamless HR (FIG. 2B, lower panel and FIG. 14).

Figure 2C:
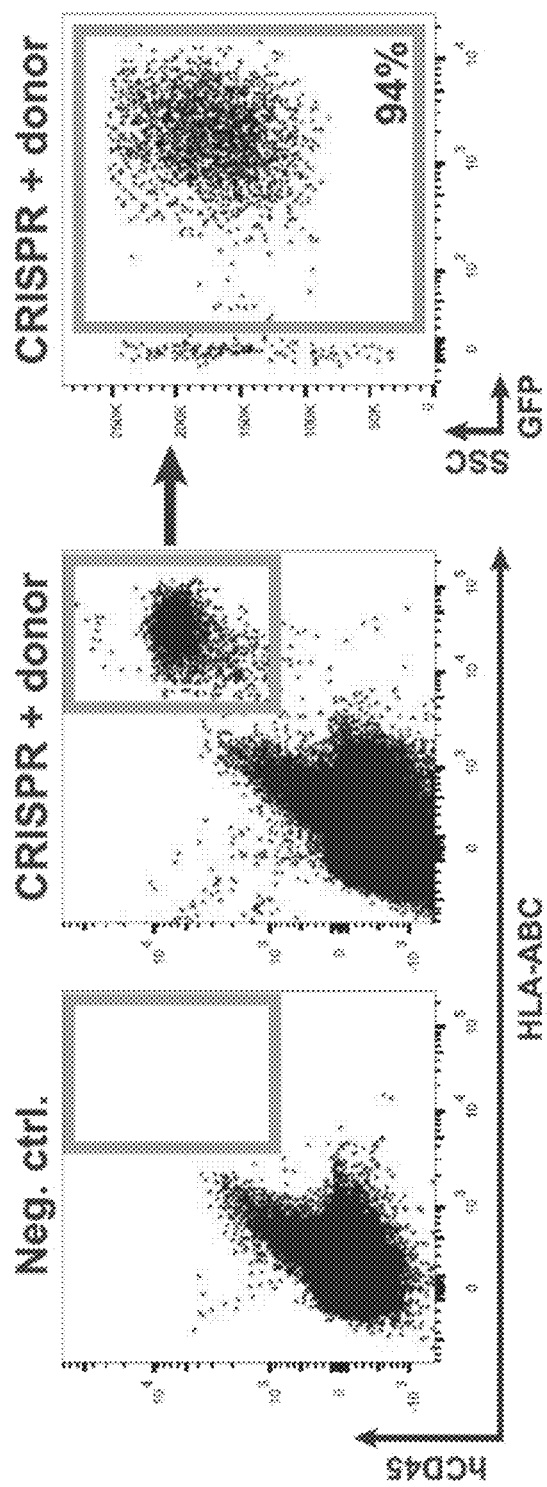

Only a small fraction of the CD34+ HSPCs are stem cells that are capable of long-term repopulation. To examine if the two-step HR process occurred in long-term repopulating stem cells, sorted GFP+ HSPCs were transplanted into three irradiated immunodeficient NOD scid gamma (NSG) mice. 16 weeks after transplant, all mice showed human chimerism in the bone marrow with an average of 91% GFP+ cells in the human population (FIG. 2C). Collectively, these data show that a split rAAV donor system can efficiently undergo sequential HR stimulated by the CRISPR system in the K562 cell line, in primary human T cells, and in HSPCs.

Figure 3A:
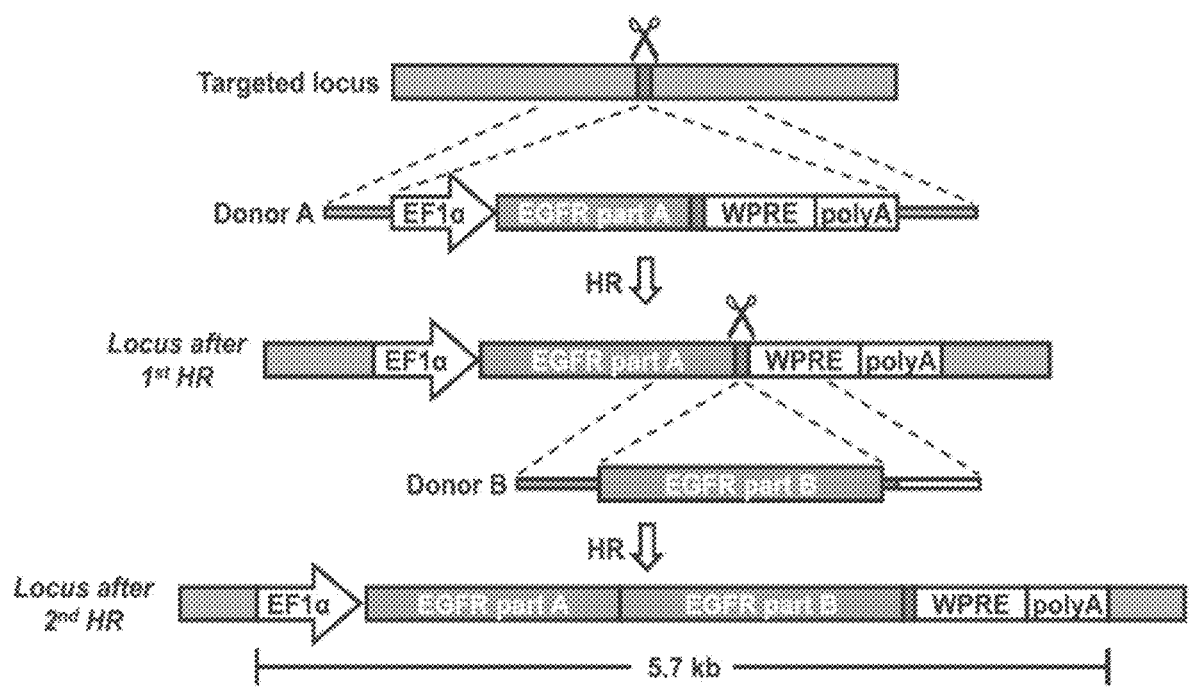
FIGS. 3A-3C show sequential homologous recombination of two AAV6 donors with a split EGFR gene in human T cells and CD34+ hematopoietic stem and progenitor cells.
Figure 3B:
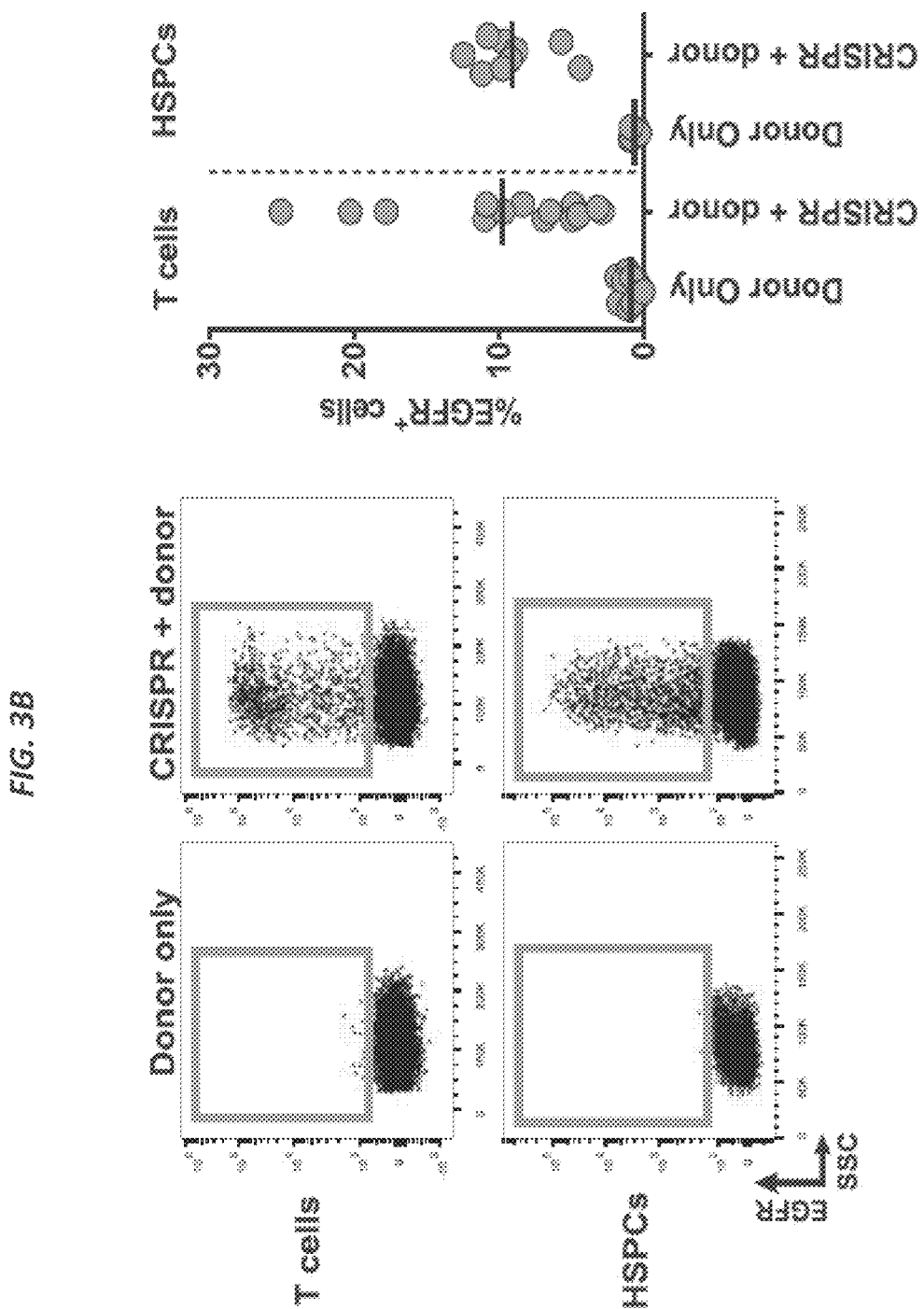
Figure 3C:
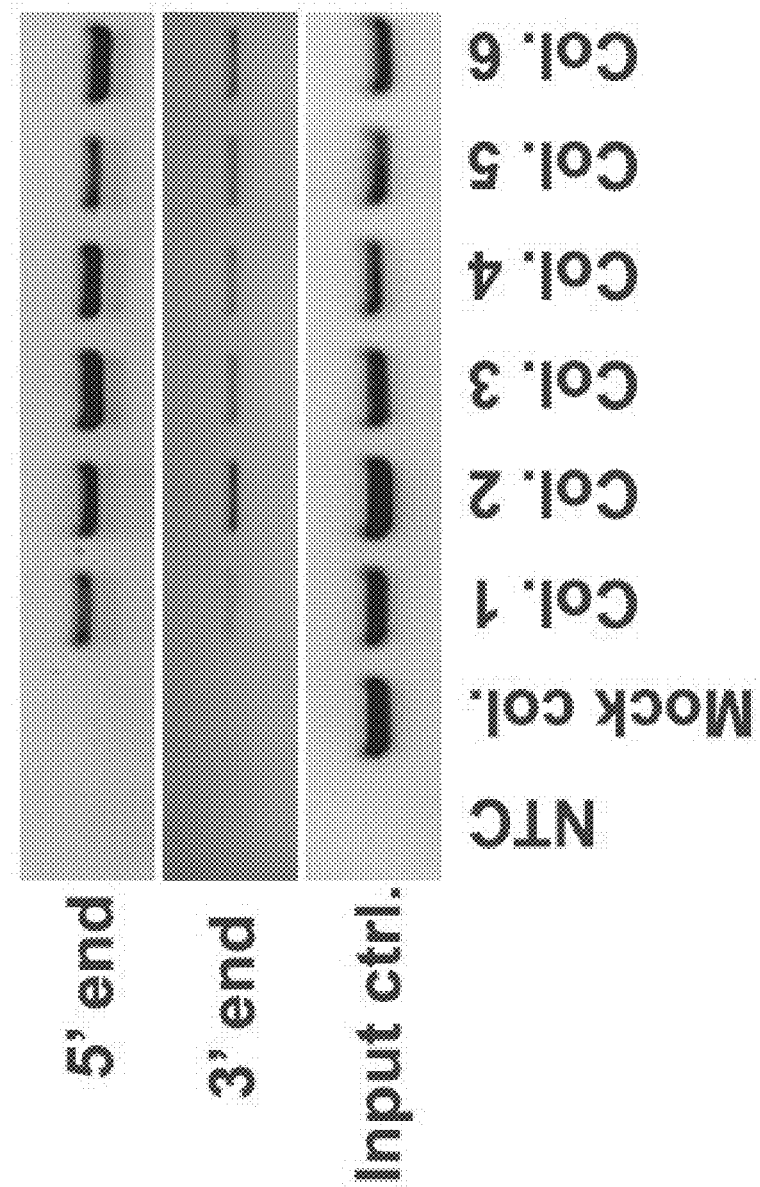
Figure 15:
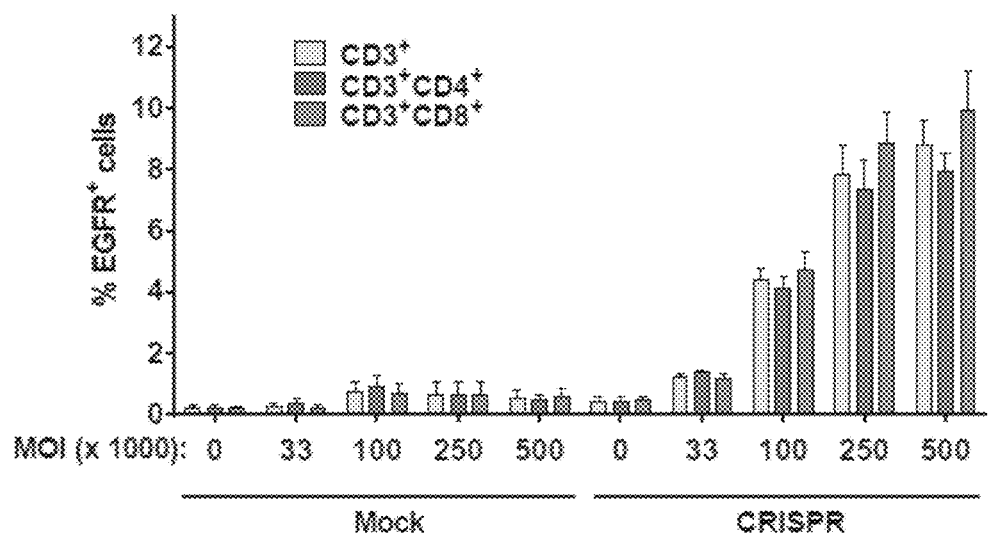
FIG. 15 depicts AAV6 dose response of the split EGFR system in primary human T cells. Primary human T cells were stimulated for three days and then electroporated with Cas9 RNP (CRISPR) or mock-electroporated, and then transduced with increasing MOIs of AAV6 split EGFR donors (MOI is per donor). EGFR expression was analyzed by flow cytometry after four days in total CD3+ cells and CD4+ and CD8+ subpopulations. Bars represent mean±SEM, N=4 (T cells from four different buffy coat donors).
Figure 16:
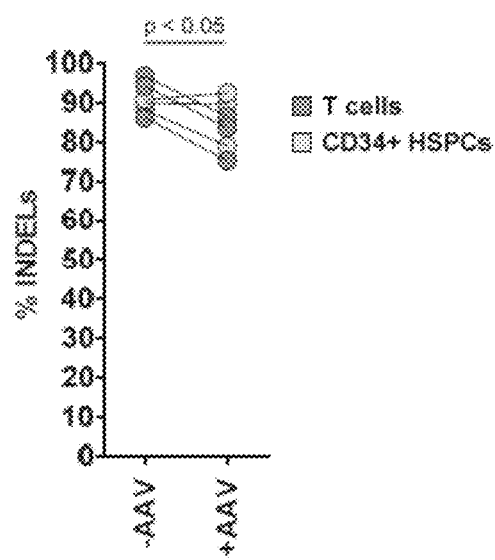
FIG. 16 shows a comparison of INDEL rates in cells electroporated with Cas9 RNP with and without transduction of donors of the split EGFR system. Primary human T cells or CD34+ HSPCs were electroporated with Cas9 RNP and split into two populations that were either left untransduced or transduced with the two AAV6 donors of the EGFR system. Four days after electroporation and transduction, genomic DNA was extracted and the targeted CCR5 locus was PCR-amplified, amplicons were Sanger-sequenced, and INDEL rates analyzed using TIDE (Tracking of Indels by Decomposition). Note that the PCR only amplifies alleles that have not undergone HR, i.e. WT alleles or alleles with INDELs. N=3 (T cells from 3 different buffy coat donors)

The epidermal growth factor receptor (EGFR) with an open reading frame of 3.6 kb can modulate cell migration and proliferation, and has been shown to play roles in HSPC expansion and G-CSF-induced HSPC mobilization (Takahashi et al., 1998, Ryan et al., 2010). The methodology was then applied to try and integrate EGFR into the CCR5 gene. With the EF1α promoter, the Woodchuck Hepatitis Virus Posttranscriptional Regulatory Element (WPRE), bovine growth hormone (BGH) polyadenylation signal (polyA), and two 400 bp homology arms, such targeting vector would be 6.5 kb, greatly exceeding the packaging capacity of AAV. The EGFR gene was split between two donors as before, but to avoid introducing stuffer DNA as in the split GFP system, the WPRE and BGH polyA was introduced along EGFR part A after the sgRNA target site, so that part of WPRE could serve as homology arm for 'Donor B' (FIG. 3A). Using this split AAV6 donor pair in T cells and HSPCs, donor only controls yielded less than 1.0% EGFR+ cells in both cell types, but with Cas9 RNP electroporation an average of 9.8% and 9.1% EGFR+ cells was detected in the two cell types, respectively, with similar rates of EGFR+ cells in the CD4 and CD8 sub-populations (FIGS. 3B and 15). Quantification of INDEL rates showed that alleles that had not undergone HR mainly harbored INDELs (FIG. 16). Minimal toxicity was observed in T cells, while modest toxicity was observed in CD34+ HSPCs, which was mainly caused by the high MOI used for AAV6 transduction (FIG. 17). Colony-forming unit assays on the EGFR+ HSPC population showed formation of erythroid, myeloid, and mixed colonies at comparable ratio to mock-electroporated cells and a small, but non-statistical significant decrease in overall formation frequency (FIG. 18). Finally, In-Out PCRs on colony-derived genomic DNA confirmed on-target integration in all analyzed colonies (20 colonies total), and sequencing confirmed seamless integration by HR (FIG. 3C).

III. Discussion

The findings establish that efficient iterative homologous recombination after simultaneous delivery of the genome editing components can occur in human cells, which may enable complex genome engineering through intracellular genomic DNA assembly.

Importantly, the system is not only highly efficient in human cancer cell lines, but is also very efficient in primary human blood cells including primary T cells and CD34+ HSPCs. A key aspect of the system is that it does not involve having to serially transfect and transduce cells, but instead can be performed in a single step in which the intracellular homologous recombination machinery naturally iterates the process. This is particularly important when working with stem cells like CD34+ HSPCs that do not tolerate repeated genetic manipulations well and differentiate during extended culturing. While other viral vectors with larger carrying capacity have been used to deliver HR templates, e.g. gutless adenoviral vectors and integration defective lentiviral vectors (IDLV) (Knipping et al., 2017, Hoban et al., 2016, Holkers et al., 2014, Zhang et al., 2014a, Genovese et al., 2014, Zhang et al., 2014b), AAV is currently the vector platform of choice for gene editing in primary T cells and HSPCs since it supports high rates of homologous recombination (Sather et al., 2015). However, in other cell types, different viral vectors may be superior in donor template delivery. Nonetheless, since rates of homologous recombination decrease with increasing insert size, a sequential two-step HR approach may prove to be equivalent to or even more efficient than a single-step integration of a large insert (Perez et al., 2005, Kung et al., 2013). Of note, the principle of sequential HR should be applicable to other viral vectors system as well.

Existing methods for expression of long transgenes split between two AAV vectors rely either on an approach where two overlapping vectors after transduction recombine or anneal before second strand-synthesis to produce the full-length large expression cassette, or on an approach where two vectors are designed with splice donor and acceptor in each vector so that upon intermolecular head-to-tail concatemerization the full-length mRNA transcript is produced. Both these approaches rely on interaction between the two donor vectors and the production of a full-length episomal expression vector. The approach disclosed herein differs mechanistically from these as it relies on two sequential events of homologous recombination between the donor vectors and the genome, thus reestablishing the full-length expression cassette upon integration into the genome.

Figure 4:
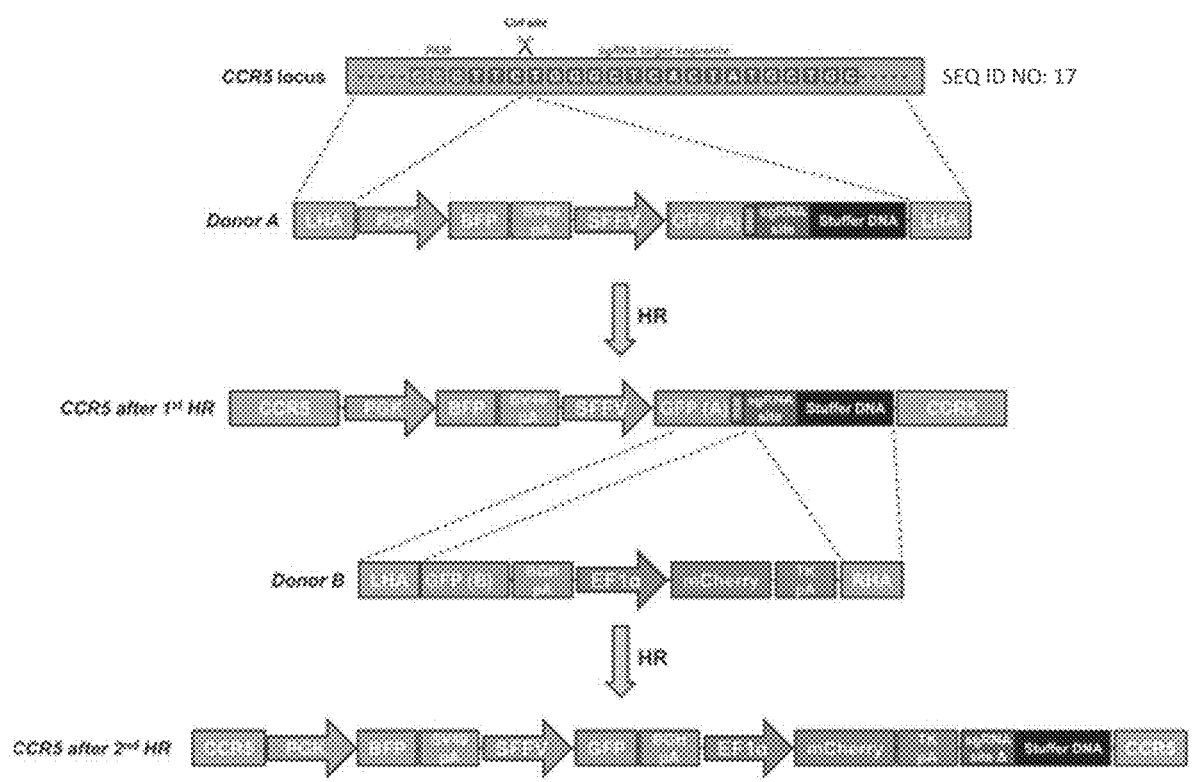
FIG. 4 depicts an overview of donor design for splitting GFP between two donors. The endogenous CCR5 target site is shown with the PAM in red and the 20 nt target site in purple. The Cas9 cut site is between nucleotide 17 and 18 of the target sequence. Donor A is designed with 2×400 bp homology arms (LHA and RHA) that are split at the CCR5 target site. The homology arms flank a PGK-BFP expression cassette, part A of the GFP expression cassette (SFFV-GFP (a)), a sgRNA target site for the same CCR5 sgRNA, and stuffer DNA (to serve as homology arm for donor B to avoid having to re-use the 400 bp CCR5 left homology arm). After HR of donor A, donor B is designed to seamlessly integrate the rest of GFP using the sgRNA target site present in donor A. Donor B has arms homologous to GFP (LHA, begins at amino acid 57 of GFP) and part of the sgRNA target site and the stuffer DNA (RHA), and it also carries an EF1α-mCherry expression cassette. Neither donor expresses GFP on its own (FIGS. 6A and 6B).

Interestingly, in the K562 cell line episomal reconstitution of the GFP expression cassette (FIG. 7) was observed. It was hypothesized that this episomal expression could be generated by annealing of the left homology arm of donor B to the complementary sequence in donor A, which would prime upstream second strand synthesis and regenerate the GFP cassette (FIG. 4). It cannot be ruled out that episomal DNA forms can be generated that serve as donor template for a single-step targeted integration of the full expression cassette. The sequential HR platform uses the same sgRNA for both HR events, which simplifies the design and avoids the use of different sgRNAs, which would presumably double the required Cas9 RNP dose and potentially lead to higher rates of off-target activity and translocations. One rate-limiting step of the procedure is that the sgRNA target site may be mutated by non-homologous end-joining (NHEJ). When this happens after the first HR event it can prevent the second HR step from occurring thereby leaving a truncated but functional expression cassette. To avoid production of a truncated protein, donor A may be designed so that the truncated mRNA transcript does not contain a stop codon in any reading frame downstream of the sgRNA target site so that the transcripts undergo nonsense mediated decay (van Hoof et al., 2002, Frischmeyer et al., 2002), and it may be designed with miRNA binding sites downstream of the sgRNA target site for rapid RNAi-mediated degradation of the transcripts (Brown et al., 2006). Alternatively, a reporter gene may be included for selection of cells that have undergone both HR steps, or the order of the HR steps may be reversed so the promoter is integrated at the second step.

In conclusion, it was demonstrated that the homologous recombination machinery in primary human blood cells is robust enough to facilitate sequential HR for integration of gene expression cassettes that exceed the packaging capacity of AAV. This is desirable for therapeutic genome editing that involves integration of large transgenes, in settings where a multi-cistronic cassette is introduced, or in the setting where two or more full transgene cassettes (Promoter-Transgene-polyA signal) need to be integrated. Each of these examples has features that will enable specific therapeutic and research applications in the future.

IV. Experimental Procedures

AAV Vector Production

The backbone for all AAV vector plasmids were the pAAV-MCS plasmid (Agilent Technologies. Santa Clara, Calif.), which contains ITRs from AAV serotype 2. All homology arms used were 400 bp each. Plasmids were produced using standard molecular cloning techniques. Plasmid pDGM6 plasmid (a kind gift from David Russell, University of Washington, Seattle, Wash., USA) was used in the virus production, which contains the AAV6 cap genes, AAV2 rep genes, and adenovirus helper genes. AAV6 vectors were produced by iodixanol gradient purification as described in (Dever et al., 2016). Vectors were titered using quantitative PCR to measure number of vector genomes as described here (Aurnhammer et al., 2012).

Cell Isolation and Culture

CD34+ HSPCs from cord blood were acquired from donors under informed consent via the Binns Program for Cord Blood Research at Stanford University. CD34+ cells were purified using the CD34+ Microbead Kit Ultrapure (Miltenyi Biotec, San Diego, Calif., USA) according to manufacturer's protocol. All CD34+ HSPCs were used fresh without freezing, and cultured at 37° C., 5% $CO_2$, and 5% $O_2$ in StemSpan SFEM II (Stemcell Technologies, Vancouver, Canada) supplemented with SCF (100 ng/ml), TPO (100 ng/ml), Flt3-Ligand (100 ng/ml), IL-6 (100 ng/ml), StemRegenin1 (0.75 mM), and UM171 (35 nM). Primary human CD3+ T cells were isolated from buffy coats obtained from the Stanford School of Medicine Blood Center using a human Pan T Cell Isolation Kit (Miltenyi Biotec, San Diego, Calif., USA) according to manufacturer's instructions. CD3+ cells were cultured at 37° C., 5% $CO_2$, and 20% $O_2$ in X-VIVO 15 (Lonza, Walkersville, Md., USA) supplemented with 5% human serum (Sigma-Aldrich, St. Louis, Mo., USA), 100 IU/mL human recombinant IL-2 (Peprotech, Rocky Hill, N.J., USA), and 10 ng/mL human recombinant IL-7 (BD Biosciences, San Jose, Calif., USA). Before electroporation, T cells were activated for three days with immobilized anti-CD3 antibodies (clone: OKT3, Tonbo Biosciences, San Diego, Calif., USA) and soluble anti-CD28 antibodies (clone: CD28.2, Tonbo Biosciences). K562 cells were purchased from ATCC (Manassas, Va., USA) and cultured at 37° C., 5% $CO_2$, and 20% $O_2$ in RPMI 1640 (HyClone) supplemented with 10% bovine growth serum, 100 mg/ml streptomycin, 100 units/mi penicillin, and 2 mM L-glutamine.

Electroporation and Transduction of Cells

The CCR5 synthetic sgRNA used were purchased HPLC-purified from TriLink BioTechnologies (San Diego, Calif., USA) and contained chemically modified nucleotides (2'O-Methyl 3'phosphorothioate) at the three terminal positions at both the 5' and 3' ends. The sequence of the CCR5 sgRNA with the modified nucleotides underlined: 5'-GCAG-CAUAGUGAGCCCAGAAGUUUUAGAGCUA-GAAAUAGCAAGUUAAAAUAA GGCUAGU-CCGUUAUCAACUUGAAAAAGUGGCACCGAGU-CGGUGQCUU-3' (SEQ ID NO:1).

Cas9 mRNA containing 5-methylcytidines and pseudouridines was purchased from TriLink BioTechnologies. Cas9 protein was purchased from IDT (San Jose, Calif., USA). Cas9 protein and sgRNAs were complexed by incubation at a molar ratio of 1:2.5 at 25° C. for 10 min immediately prior to electroporation. CD34+ HSPCs were electroporated 2 days after isolation and T cells were electroporated 3 days after stimulation. All electroporations were performed on the Lonza Nucleofector IIb (program U-014 for HSPCs and T cells, and program T-016 for K562 cells). For CD34+ HSPCs and T cells, either the Human T Cell Nucleofection Kit (VPA-1002, Lonza) or the IM electroporation buffer described in (Chicaybam et al., 2013) were used. The following conditions were used for electroporation: 5-10× $10^6$ cells/mL, 300 ug/mL Cas9 protein complexed with sgRNA at 1:2.5 molar ratio. For K562 electroporations, an electroporation buffer containing 100 mM KH2PO4, 15 mM NaHCO3, 12 mM MgCl2×6H2O, 8 mM ATP, 2 mM glucose (pH 7.4) was used with 50 g/mL Cas9 mRNA and 50 µg/mL sgRNA. For experiments with plasmid donors, 2.5 µg of each plasmid was used. For experiments using AAV6 donors, directly following electroporation, cells were incubated for 15 min at 37° C. after which they were added AAV6 at 20% of the final culture volume (multiplicity of infection [MOI] was typically ~2-5×$10^5$ vg/cell per AAV donor). Cells were analyzed 4 days after electroporation and transduction.

Flow Cytometry

Expression of fluorescent proteins or cell surface markers was analyzed by flow cytometry on a BD FACSAria II SORP (Franklin Lakes, N.J., USA) or a CytoFLEX Flow Cytometer (Brea, Calif., USA). The following antiobodies were used: anti-EGFR (PE or APC, clone: AY13, BioLegend, San Diego, Calif., USA), anti-CCR5 (APC, clone: 2D7/CCR5, BD Biosciences), anti-CD3 (BV605, clone: UCHT1, Biolegend), anti-CD4+(PE-Cy7, clone: RPA-T4, Tonbo Biosciences), anti-CD8 (VF450, clone: RPA-T8, Tonbo Biosciences). The blue or violet LIVE/DEAD Fixable Dead Cell Stain Kit (Life Technologies) or the Ghost Dye Red 780 (Tonbo Biosceiences) was used to discriminate live and dead cells according to manufacturer's instructions. For discrimination of apoptotic cells, PE or APC labeled annexin V (BioLegend) was used following manufacturer's instructions.

Methylcellulose Colony-Forming Unit (CFU) Assay and PCR Detection of Integration The CFU assay was performed by FACS sorting of single cells into 96-well plates containing MethoCult Optimum or MethoCult Enriched (Stemcell Technologies) four days after electroporation and transduction. After 12-16 days, colonies were counted and scored based on their morphological appearance in a blinded fashion. Confirmation of on-target integration was performed by PCR on colony-derived genomic DNA that was extracted from colonies by adding PBS to the colonies, mixing followed by pelleting of cells. After washing with PBS, cells were resuspended in 25 µl QuickExtract DNA Extraction Solution (Epicentre, Madison. WL USA) and incubated at 65° C. for 10 min followed by 100° C. for 2 min. Integration was detected by PCR using the following primers: GFP integration 5' end fw: 5'-cc-caacagagccaagctctcc-3' (SEQ ID NO:2); GFP integration 5' end rv: 5'-ccggtggatgtggaatgtgtgc-3' (SEQ ID NO:3); GFP integration 3' end fw: 5'-ggctcgcagccaacgtc-3' (SEQ ID NO:4); GFP integration 3' end rv: 5'-catgatggtgaagataagcct-cacagc-3' (SEQ ID NO:5); EGFR integration 5' end fw: 5'-cccaacagagccaagctctcc-3' (SEQ ID NO:6); EGFR integration 5' end rv: 5'-gcaccggttcaattgccgacc-3' (SEQ ID NO:7); EGFR integration 3' end fw: 5'-ccaaatggcatctttaagggctcc-3' (SEQ ID NO:8); EGFR integration 3' end rv: 5'-gtgcctcttcttctcatttcgacacc-3' (SEQ ID NO:9); HBB fw: 5'-ccaactcctaagccagtgccagaagag-3' (SEQ ID NO: 10); HBB rv: 5'-agtcagtgcctatcagaaacccaagag-3' (SEQ ID NO: 11).

Analysis of IN DEL Rates

Genomic DNA was extracted using QuickExtract DNA (Epicentre, Madison, Wis., USA) following manufacturer's instructions, but using 50 uL QuickExtract solution per 100,000 cells and extending the last incubation step at 100° C. to 10 min. The targeted region of CCR5 was PCR-amplified with primers spanning the sgRNA target sites: CCR5 (fw): 5'-GCACAGGGTGGAACAAGATGG-3' (SEQ ID NO:12); CCR5 (rv): 5'-CACCACCC-CAAAGGTGACCGT-3' (SEQ ID NO: 13).

The iProof High-Fidelity Master Mix was used for PCR-amplification for 35 cycles (Bio-Rad, Hercules, Calif., USA), and the purified PCR products were run on a 1% agarose gel, gel-extracted, and then Sanger-sequenced using both PCR primers. Each sequence chromatogram was analyzed using the TIDE software (at website tide.nki.nl). Mock-electroporated samples were used as reference sequence and parameters were set to an INDEL size of 30 nucleotides and the decomposition window to cover the largest possible window with high quality traces. For TOPO cloning, gel-purified PCR amplicons were cloned into the TOPO plasmid using the Zero Blunt TOPO PCR Cloning Kit (Life Technologies) according to manufacturer's protocol. TOPO plasmids were transformed into XL-1 Blue competent *E. coli*, plated on agar plates with kanamycin, and single colonies were sequenced by McLab (South San Francisco, Calif., USA) by rolling circle amplification and sequencing using the forward primer used for PCR amplification.

Transplantation and Analysis of Human Cells in NSG Mice

For in vivo studies, 6 to 8 week-old NOD scid gamma (NSG) mice were purchased from the Jackson laboratory (Bar Harbor, Me. USA). The experimental protocol was approved by Stanford University's Administrative Panel on Lab Animal Care. Four days after electroporation and transduction, GFP+ cells were sorted and 40,000 cells were injected intrafemorally into each of three male mice, which had been sublethally irradiated the day before transplantation at 200 cGy. 16 weeks post-transplantation, mice were euthanized, bones (2× femur, 2× tibia, 2× pelvis, sternum, and spine) were collected and crushed using mortar and pestle. Mononuclear cells (MNCs) were isolated using Ficoll gradient centrifugation (Ficoll-Paque Plus, GE Healthcare, Sunnyvale, Calif., USA) for 25 min at 2,000×g, room temperature. Cells were blocked for nonspecific antibody binding (10% vol/vol, TruStain FcX, BioLegend) and stained (30 min, 4° C., dark) with the following antibodies: anti-human CD45 (BV786, clone: HI30, BD Biosciences), anti-HLA-ABC (APC-Cy7, clone: W6/32, BioLegend), anti-mouse CD45.1 (PE-Cy7, clone: A20, eBioScience, San Diego, Calif., USA), anti-mouse Ter-119 (BUV395, clone: TER-119, eBioscience). The LIVE/DEAD Fixable Blue Cell Stain Kit (Life Technologies) was used to discriminate live and dead cells according to manufacturer's instructions. Human engraftment was defined by the presence of human CD45+/HLA-ABC+ double-positive cells.

V. References

AURNHAMMER, C., HAASE, M., MUETHER, N., HAUSL, M., RAUSCHHUBER, C., HUBER, I., NITSCHKO, H., BUSCH, U., SING, A., EHRHARDT, A. & BAIKER, A. 2012. Universal real-time PCR for the detection and quantification of adeno-associated virus serotype 2-derived inverted terminal repeat sequences. Hum Gene Ther Methods, 23, 18-28.

BASIRI, M., BEHMANESH, M., TAHAMTANI, Y., KHALOOGHI, K., MORADMAND, A. & BAHARVAND, H. 2017. The Convenience of Single Homology Arm Donor DNA and CRISPR/Cas9-Nickase for Targeted Insertion of Long DNA Fragment. Cell J, 18, 532-539.

BROWN, B. D., VENNERI, M. A., ZINGALE, A., SERGI SERGI, L. & NALDINI, L. 2006. Endogenous microRNA regulation suppresses transgene expression in hematopoietic lineages and enables stable gene transfer. Nat Med, 12, 585-91.

CHAMBERLAIN, K., RIYAD, J. M. & WEBER, T. 2016. Expressing Transgenes That Exceed the Packaging Capacity of Adeno-Associated Virus Capsids. Hum Gene Ther Methods, 27, 1-12.

CHICAYBAM, L., SODRE, A. L., CURZIO, B. A. & BONAMINO, M. H. 2013. An efficient low cost method for gene transfer to T lymphocytes. PLoS One, 8, e60298.

DE RAVIN, S. S., LI, L., WU, X., CHOI, U., ALLEN, C., KOONTZ, S., LEE, J., THEOBALD-WHITING, N., CHU, J., GAROFALO, M., SWEENEY, C., KARDAVA, L., MOIR, S., VILEY, A., NATARAJAN, P., SU, L., KUHNS, D., ZAREMBER, K. A., PESHWA, M. V. & MALECH, H. L. 2017. CRISPR-Cas9 gene repair of hematopoietic stem cells from patients with X-linked chronic granulomatous disease. Sci Transl Med, 9.

DEVER, D. P., BAK, R. O., REINISCH, A., CAMARENA, J., WASHINGTON, G., NICOLAS, C. E., PAVEL-DINU, M., SAXENA, N., WILKENS, A. B., MANTRI, S., UCHIDA, N., HENDEL, A., NARLA, A., MAJETI, R., WEINBERG, K. I. & PORTEUS, M. H. 2016. CRISPR/Cas9 beta-globin gene targeting in human haematopoietic stem cells. Nature, 539, 384-389.

DEWITT, M. A., MAGIS, W., BRAY, N. L., WANG, T., BERMAN, J. R., URBINATI, F., HEO, S. J., MITROS, T., MUNOZ, D. P., BOFFELLI, D., KOHN, D. B., WALTERS, M. C., CARROLL, D., MARTIN, D. I. & CORN, J. E. 2016. Selection-free genome editing of the sickle mutation in human adult hematopoietic stem/progenitor cells. Sci Transl Med, 8, 360ra134.

FRISCHMEYER, P. A., VAN HOOF, A., O'DONNELL, K., GUERRERIO, A. L., PARKER, R. & DIETZ, H. C. 2002. An mRNA surveillance mechanism that eliminates transcripts lacking termination codons. Science, 295, 2258-61.

GENOVESE, P., SCHIROLI, G., ESCOBAR, G., DI TOMASO, T., FIRRITO, C., CALABRIA, A., MOI, D., MAZZIERI, R., BONINI, C., HOLMES, M. C., GREGORY, P. D., VAN DER BURG, M., GENTNER, B., MONTINI, E., LOMBARDO, A. & NALDINI, L. 2014. Targeted genome editing in human repopulating haematopoietic stem cells. Nature, 510, 235-40.

GRIEGER, J. C. & SAMULSKI, R. J. 2005. Packaging capacity of adeno-associated virus serotypes: impact of larger genomes on infectivity and postentry steps. J Virol, 79, 9933-44.

HALBERT, C. L., ALLEN, J. M. & MILLER, A. D. 2002. Efficient mouse airway transduction following recombination between AAV vectors carrying parts of a larger gene. Nat Biotechnol, 20, 697-701.

HENDEL, A., BAK, R. O., CLARK, J. T., KENNEDY, A. B., RYAN, D. E., ROY, S., STEINFELD, I., LUNSTAD, B. D., KAISER, R. J., WILKENS, A. B., BACCHETTA, R., TSALENKO, A., DELLINGER, D., BRUHN, L. & PORTEUS, M. H. 2015. Chemically modified guide RNAs enhance CRISPR-Cas genome editing in human primary cells. Nat Biotechnol, 33, 985-9.

HENDEL, A., KILDEBECK, E. J., FINE, E. J., CLARK, J. T., PUNJYA, N., SEBASTIANO, V., BAO, G. & PORTEUS, M. H. 2014. Quantifying genome-editing outcomes at endogenous loci with SMRT sequencing. Cell Rep, 7, 293-305.

HOBAN, M. D., LUMAQUIN, D., KUO, C. Y., ROMERO, Z., LONG, J., HO, M., YOUNG, C. S., MOJADIDI, M., FITZ-GIBBON, S., COOPER, A. R., LILL, G. R., URBINATI, F., CAMPO-FERNANDEZ, B., BJURSTROM, C. F., PELLEGRINI, M., HOLLIS, R. P. & KOHN, D. B. 2016. CRISPR/Cas9-Mediated Correction of the Sickle Mutation in Human CD34+ cells. Mol Ther, 24, 1561-9.

HOLKERS, M., MAGGIO, I., HENRIQUES, S. F., JANSSEN, J. M., CATHOMEN, T. & GONCALVES, M. A. 2014. Adenoviral vector DNA for accurate genome editing with engineered nucleases. Nat Methods, 11, 1051-7.

KNIPPING, F., OSBORN, M. J., PETRI, K., TOLAR, J., GLIMM, H., VON KALLE, C., SCHMIDT, M. & GABRIEL, R. 2017. Genome-wide Specificity of Highly Efficient TALENs and CRISPR/Cas9 for T Cell Receptor Modification. Mol Ther Methods Clin Dev, 4, 213-224.

KUNG, S. H., RETCHLESS, A. C., KWAN, J. Y. & ALMEIDA, R. P. 2013. Effects of DNA size on transformation and recombination efficiencies in Xylella fastidiosa. Appl Environ Microbiol, 79, 1712-7.

LOMBARDO, A., GENOVESE, P., BEAUSEJOUR, C. M., COLLEONI, S., LEE, Y. L., KIM, K. A., ANDO, D., URNOV, F. D., GALLI, C., GREGORY, P. D., HOLMES, M. C. & NALDINI, L. 2007. Gene editing in human stem cells using zinc finger nucleases and integrase-defective lentiviral vector delivery. Nat Biotechnol, 25, 1298-306.

NAKAI, H., STORM, T. A. & KAY, M. A. 2000. Increasing the size of rAAV-mediated expression cassettes in vivo by intermolecular joining of two complementary vectors. Nat Biotechnol, 18, 527-32.

PEREZ, C., GUYOT, V., CABANIOLS, J. P., GOUBLE, A., MICHEAUX, B., SMITH, J., LEDUC, S., PAQUES, F. & DUCHATEAU, P. 2005. Factors affecting double-strand break-induced homologous recombination in mammalian cells. Biotechniques, 39, 109-15.

RYAN, M. A., NATTAMAI, K. J., XING, E., SCHLEIMER, D., DARIA, D., SENGUPTA, A., KOHLER, A., LIU, W., GUNZER, M., JANSEN, M., RATNER, N., LE CRAS, T. D., WATERSTRAT, A., VAN ZANT, G., CANCELAS, J. A., ZHENG, Y. & GEIGER, H. 2010. Pharmacological inhibition of EGFR signaling enhances G-CSF-induced hematopoietic stem cell mobilization. Nat Med, 16, 1141-6.

SATHER, B. D., ROMANO IBARRA, G. S., SOMMER, K., CURINGA, G., HALE, M., KHAN, I. F., SINGH, S., SONG, Y., GWIAZDA, K., SAHNI, J., JARJOUR, J., ASTRAKHAN, A., WAGNER, T. A., SCHARENBERG, A. M. & RAWLINGS, D. J. 2015. Efficient modification of CCR5 in primary human hematopoietic cells using a megaTAL nuclease and AAV donor template. Sci Transl Med, 7, 307ra156.

SUN, L., LI, J. & XIAO, X. 2000. Overcoming adeno-associated virus vector size limitation through viral DNA heterodimerization. Nat Med, 6, 599-602.

TAKAHASHI, T., YAMADA, K., TANAKA, T., KUMANO, K., KUROKAWA, M., HIRANO, N., HONDA, H., CHIBA, S., TSUJI, K., YAZAKI, Y., NAKAHATA, T. & HIRAI, H. 1998. A potential molecular approach to ex vivo hematopoietic expansion with recombinant epidermal growth factor receptor-expressing adenovirus vector. Blood, 91, 4509-15.

VAN HOOF, A., FRISCHMEYER, P. A., DIETZ, H. C. & PARKER, R. 2002. Exosome-mediated recognition and degradation of mRNAs lacking a termination codon. Science, 295, 2262-4.

WANG, J., EXLINE, C. M., DECLERCQ, J. J., LLEWELLYN, G. N., HAYWARD, S. B., LI, P. W., SHIVAK, D. A., SUROSKY, R. T., GREGORY, P. D., HOLMES, M. C. & CANNON, P. M. 2015. Homology-driven genome editing in hematopoietic stem and progenitor cells using ZFN mRNA and AAV6 donors. Nat Biotechnol, 33, 1256-1263.

YANG, Y., WANG, L., BELL, P., MCMENAMIN, D., HE, Z., WHITE, J., YU, H., XU, C., MORIZONO, H., MUSUNURU, K., BATSHAW, M. L. & WILSON, J. M. 2016. A dual AAV system enables the Cas9-mediated correction of a metabolic liver disease in newborn mice. Nat Biotechnol, 34, 334-8.

YIN, H., SONG, C. Q., DORKIN, J. R., ZHU, L. J., LI, Y., WU, Q., PARK, A., YANG, J., SURESH, S., BIZHANOVA, A., GUPTA, A., BOLUKBASI, M. F., WALSH, S., BOGORAD, R. L., GAO, G., WENG, Z., DONG, Y., KOTELIANSKY, V., WOLFE, S. A., LANGER, R., XUE, W. & ANDERSON, D. G. 2016. Therapeutic genome editing by combined viral and non-viral delivery of CRISPR system components in vivo. Nat Biotechnol, 34, 328-33.

ZHANG, W., CHEN, H., ZHENG, X., WANG, D., JI, H., XIA, H. & MAO, Q. 2014a. Targeted genome correction by a single adenoviral vector simultaneously carrying an inducible zinc finger nuclease and a donor template. J Biotechnol, 188, 1-6.

ZHANG, W., WANG, D., LIU, S., ZHENG, X., JI, H., XIA, H. & MAO, Q. 2014b. Multiple copies of a linear donor fragment released in situ from a vector improve the efficiency of zinc-finger nuclease-mediated genome editing. Gene Ther, 21, 282-8.

Example 2: CFTR—Universal Correction Using Split Strategy

The universal method for gene correction using the split strategy described herein includes three details: (1) the sgRNA, (2) the correction template, and (3) the delivery strategy.

For cystic fibrosis transmembrane conductance regulator gene (CFTR) correction, the DSB was induced in Exon 1 using sgRNA, e.g., a CFTR synthetic sgRNA (UUCCAGAGGCGACCUCUGCA; SEQ ID NO: 14). In the universal strategy, the correction template included a codon diverged CFTR sequence followed by a BGH poly-A tail, truncated-CD19 (tCD19) under the control of a PGK promoter and SV-40 poly-A tail. The PGK promoter-tCD19-SV40 cassette allowed for enrichment of successfully edited cells since CFTR is not expressed in sinus stem cells.

Furthermore, the universal template was delivered using two AAV donors. The first AAV virus contained 400 base pair (bp) left homology arm (LHA) consisting of 400 bp upstream of the DSB site, the first 2883 bp of the CFTR cDNA sequence, CF-Universal sgRNA sequence (UUCCAGAGGCGACCUCUGCA; SEQ ID NO: 14), 400 bp stuffer DNA and 400 base pair (bp) right homology arm (RHA) consisting of 400 bp upstream of the original DSB site. The 2883 bp CFTR cDNA insert was diverged from the native sequence to (i) remove the sgRNA sequence so that it is not recut by the Cas9/sgRNA and (ii) to prevent recombination with native CFTR sequence. The second AAV virus was centered around the sgRNA site included in the first AAV donor. It included the last 400 bp of the CFTR cDNA sequence as LHA-II, the second 1560 bp of the CFTR cDNA sequence, BGH poly-A tail, PGK promoter, truncated-CD19, SV40 poly-A, and finally the stuffer from the first AAV as RHA-II. Two different polyA tails (BGH and SV40) were used to minimize any potential recombination events.

The split strategy uses two correction templates (FIG. 19A). The first template carries the first 2883 bp of CFTR cDNA along to which the sgRNA sequence was added and a stuffer at the end (FIGS. 20A and 20B; SEQ ID NO: 15). The second template included the last 1560 bp of CFTR cDNA along with a PGK promoter, truncated CD19 and sv40 polyA tail (FIGS. 21A and 21B; SEQ ID NO:16). Correction using these two templates resulted in 1-10% tCD19+ cells (FIG. 19B). FACS plots for sinus cells edited using tCD19 strategy (FIG. 19C). FACS enrichment of cells edited using tCD19 strategy results in 40-80% tCD19+ cells (FIG. 19C).

The data described herein show that gene correction using two separate correction templates resulted in 1-10% successfully targeted cells, e.g., targeted stem cells. In addition, the data shows that the targeted cells can be enriched to about 40%-8% targeted cells.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A system for CRISPR/Cas9-mediated integration of a target polynucleotide into a target genetic locus in a cell comprising:
   (a) a first targeting AAV vector comprising a single guide RNA (sgRNA) target site with a protospacer-adjacent motif (PAM), a first donor template, a 5' homology arm that is homologous to a first portion of the target locus, and a 3' homology arm that is homologous to a second portion of the target locus that is not overlapping with the first portion of the target locus,
   wherein the sgRNA target site is recognized by a target locus-specific sgRNA, wherein the first donor template comprises a first nucleotide sequence of the target polynucleotide;
   (b) a second targeting AAV vector comprising a second donor template, a 5' homology arm that is homologous to a first portion of the first donor template, a 3' homology arm that is homologous to a second portion of the first targeting AAV vector,
   wherein the first portion of the first donor template and the second portion of the first targeting AAV vector are not overlapping, the second donor template comprises a second nucleotide sequence of the target polynucleotide, and the nucleotide sequence of the target polynucleotide is split between the first donor template and the second donor template;
   (c) the target locus-specific sgRNA; and
   (d) a CRISPR-associated protein 9 (Cas9) polypeptide or a polynucleotide encoding the Cas9 polypeptide.

2. The system of claim 1, wherein the target locus-specific sgRNA and Cas9 polypeptide are complexed together to form a Cas9 ribonucleoprotein.

3. The system of claim 1, wherein the target locus-specific sgRNA comprises a synthetic sgRNA of SEQ ID NO:1 or SEQ ID NO:14.

4. The system of claim 1, wherein the target locus-specific sgRNA comprises one or more modified nucleotides, and wherein the modified nucleotides comprise a modification in a ribose group, a phosphate group, a nucleobase, or a combination thereof.

5. The system of claim 4, wherein the modification in the ribose group comprises a modification at the 2' position of the ribose group, wherein the modification in the phosphate group comprises a phosphorothioate or 3'-thioPACE modification, and/or the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

6. The system of any one of claim 1, wherein the first targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide and/or wherein the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide.

7. The system of claim 1, wherein the cell is isolated from a subject, and optionally the subject has a genetic disease.

8. A method of introducing a target polynucleotide into a target genetic locus in a cell comprising introducing into the cell:
   (a) a first targeting AAV vector comprising a single guide RNA (sgRNA) target site with a protospacer-adjacent motif (PAM), a first donor template, a 5' homology arm that is homologous to a first portion of the target locus, and a 3' homology arm that is homologous to a second portion of the target locus that is not overlapping with the first portion of the target locus,
   wherein the sgRNA target site is recognized by a target locus-specific sgRNA, wherein the first donor template comprises a first nucleotide sequence of the target polynucleotide(s);
   (b) a second targeting AAV vector comprising a second donor template, a 5' homology arm that is homologous to a first portion of the first donor template, a 3' homology arm that is homologous to a second portion of the first targeting AAV vector,
   wherein the first portion of the first donor template and the second portion of the first targeting AAV vector are not overlapping, the second donor template comprises a second nucleotide sequence of the target polynucle-otide(s), and the nucleotide sequence of the target polynucleotide(s) is split between the first donor template and the second donor template;
   (c) the target locus-specific sgRNA; and
   (d) a CRISPR-associated protein 9 (Cas9) polypeptide or a polynucleotide encoding the Cas9 polypeptide.

9. The method of claim 8, wherein the target locus-specific sgRNA comprises a synthetic sgRNA of SEQ ID NO:1 or SEQ ID NO:14.

10. The method of claim 8, wherein the target locus-specific sgRNA comprises one or more modified nucleotides, and wherein the modified nucleotides comprise a modification in a ribose group, a phosphate group, a nucleobase, or a combination thereof.

11. The method of claim 10, wherein the modification in a ribose group comprises a modification at the 2' position of the ribose group, wherein the modification in the phosphate group comprises a phosphorothioate or 3'-thioPACE modification, and/or wherein the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

12. The method of claim 8, wherein the first targeting AAV vector has an AAV capsid polypeptide selected from the group consisting of a AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide and/or wherein the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide.

13. The method of claim 8, further comprising selecting the cell containing the target polynucleotide and/or further comprising administering the cell containing the target polynucleotide into the subject.

14. The method of claim 8, wherein the cell is selected from the group consisting of an immune cell, a muscle cell, a liver cell, a skin cell, a retinal cell, an airway cell, a lung cell, and a stem cell.

15. A method of treating a genetic disease associated with CCR5 or CFTR in a subject, the method comprising administering to the subject:
(a) a first targeting AAV vector comprising a single guide RNA (sgRNA) target site with a protospacer-adjacent motif (PAM), a first donor template, a 5' homology arm that is homologous to a first portion of a target genetic locus, and a 3' homology arm that is homologous to a second portion of the target locus that is not overlapping with the first portion of the target locus, wherein the sgRNA target site is recognized by a target locus-specific sgRNA, and the first donor template comprises a first nucleotide sequence of a target polynucleotide(s);
(b) a second targeting AAV vector comprising a second donor template, a 5' homology arm that is homologous to a first portion of the first donor template, a 3' homology arm that is homologous to a second portion of the first targeting AAV vector, wherein the first portion of the first donor template and the second portion of the first targeting AAV vector are not overlapping, the second donor template comprises a second nucleotide sequence of the target polynucleotide, and the nucleotide sequence of the target polynucleotide(s) is split between the first donor template and the second donor template;
(c) the target locus-specific sgRNA; and
(d) a CRISPR-associated protein 9 (Cas9) polypeptide or a polynucleotide encoding the Cas9 polypeptide.

16. The method of claim 15, wherein the target locus-specific sgRNA comprises a synthetic sgRNA of SEQ ID NO:1 or SEQ ID NO:14.

17. The method of claim 15, wherein the target locus-specific sgRNA comprises one or more modified nucleotides, and wherein the modified nucleotides comprise a modification in a ribose group, a phosphate group, a nucleobase, or a combination thereof.

18. The method of claim 16, wherein the modification in the ribose group comprises a modification at the 2' position of the ribose group, wherein the modification in the phosphate group comprises a phosphorothioate or 3'-thioPACE modification, and/or wherein the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

19. The method of claim 15, wherein the first targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide and/or the second targeting AAV vector has an AAV capsid polypeptide selected from the group consisting of an AAV-DJ, AAV1, AAV2, AAV3, AAV4, AAV5, AAV6, AAV7, AAV8, AAV9, AAVbb2, AAVcy5, AAVrh10, AAVrh20, AAVrh39, AAVrh43, AAVrh64R1, AAVhu37, engineered AAV, and chimeric AAV capsid polypeptide.

* * * * *

SEQUENCE LISTING

```
<160> NUMBER OF SEQ ID NOS: 23

<210> SEQ ID NO 1
<211> LENGTH: 100
<212> TYPE: RNA
<213> ORGANISM: Artificial Sequence
<220> FEATURE:
<223> OTHER INFORMATION: CCR5 sgRNA

<400> SEQUENCE: 1
gcagcauagu gagcccagaa guuuuagagc uagaaauagc aaguuaaaau aaggcuaguc      60
cguuaucaac uugaaaaagu ggcaccgagu cggugcuuuu                          100

<210> SEQ ID NO 2
<211> LENGTH: 21
<212> TYPE: DNA
<213> ORGANISM: Artificial Sequence
<220> FEATURE:
<223> OTHER INFORMATION: GFP integration 5' end fw

<400> SEQUENCE: 2
cccaacagag ccaagctctc c                                               21

<210> SEQ ID NO 3
<211> LENGTH: 22
<212> TYPE: DNA
<213> ORGANISM: Artificial Sequence
<220> FEATURE:
<223> OTHER INFORMATION: GFP integration 5' end rv

<400> SEQUENCE: 3
ccggtggatg tggaatgtgt gc                                              22

<210> SEQ ID NO 4
<211> LENGTH: 17
<212> TYPE: DNA
<213> ORGANISM: Artificial Sequence
<220> FEATURE:
<223> OTHER INFORMATION: GFP integration 3' end fw

<400> SEQUENCE: 4
ggctcgcagc caacgtc                                                    17

<210> SEQ ID NO 5
<211> LENGTH: 27
<212> TYPE: DNA
<213> ORGANISM: Artificial Sequence
<220> FEATURE:
<223> OTHER INFORMATION: GFP integration 3' end rv
```

<400> SEQUENCE: 5
catgatggtg aagataagcc tcacagc        27

<210> SEQ ID NO 6
<211> LENGTH: 21
<212> TYPE: DNA
<213> ORGANISM: Artificial Sequence
<220> FEATURE:
<223> OTHER INFORMATION: EGFR integration 5' end fw

<400> SEQUENCE: 6
cccaacagag ccaagctctc c        21

<210> SEQ ID NO 7
<211> LENGTH: 21
<212> TYPE: DNA
<213> ORGANISM: Artificial Sequence
<220> FEATURE:
<223> OTHER INFORMATION: EGFR integration 5' end rv

<400> SEQUENCE: 7
gcaccggttc aattgccgac c        21

<210> SEQ ID NO 8
<211> LENGTH: 24
<212> TYPE: DNA
<213> ORGANISM: Artificial Sequence
<220> FEATURE:
<223> OTHER INFORMATION: EGFR integration 3' end fw

<400> SEQUENCE: 8
ccaaatggca tctttaaggg ctcc        24

<210> SEQ ID NO 9
<211> LENGTH: 26
<212> TYPE: DNA
<213> ORGANISM: Artificial Sequence
<220> FEATURE:
<223> OTHER INFORMATION: EGFR integration 3' end rv

<400> SEQUENCE: 9
gtgcctcttc ttctcatttc gacacc        26

<210> SEQ ID NO 10
<211> LENGTH: 27
<212> TYPE: DNA
<213> ORGANISM: Artificial Sequence
<220> FEATURE:
<223> OTHER INFORMATION: HBB fw

<400> SEQUENCE: 10
ccaactccta agccagtgcc agaagag        27

<210> SEQ ID NO 11
<211> LENGTH: 27
<212> TYPE: DNA
<213> ORGANISM: Artificial Sequence
<220> FEATURE:
<223> OTHER INFORMATION: HBB rv

<400> SEQUENCE: 11
agtcagtgcc tatcagaaac ccaagag        27

<210> SEQ ID NO 12
<211> LENGTH: 21

```
<212> TYPE: DNA
<213> ORGANISM: Artificial Sequence
<220> FEATURE:
<223> OTHER INFORMATION: CCR5 (fw)

<400> SEQUENCE: 12
gcacagggtg aacaagatg g                                               21

<210> SEQ ID NO 13
<211> LENGTH: 21
<212> TYPE: DNA
<213> ORGANISM: Artificial Sequence
<220> FEATURE:
<223> OTHER INFORMATION: CCR5 (rv)

<400> SEQUENCE: 13
caccacccca aggtgaccg t                                               21

<210> SEQ ID NO 14
<211> LENGTH: 20
<212> TYPE: RNA
<213> ORGANISM: Artificial Sequence
<220> FEATURE:
<223> OTHER INFORMATION: CF-Universal sgRNA sequence

<400> SEQUENCE: 14
uuccagaggc gaccucugca                                                20

<210> SEQ ID NO 15
<211> LENGTH: 5409
<212> TYPE: DNA
<213> ORGANISM: Artificial Sequence
<220> FEATURE:
<223> OTHER INFORMATION: CFTR template vector 1

<400> SEQUENCE: 15
agaatggccg tgaccagaca gttcccctgg gccgtgcaga cctggtacga cagcctgggc     60
gccatcaaca agatccagga cttttctgcag aagcaggagt acaagaccct ggagtacaac    120
ctgaccacca ccgaggtggt gatggagaat gtgaccgctt tctgggagga gggcttcggc    180
gagctgttcg agaaggccaa gcagaacaac aataacagaa agaccagcaa cggcgacgat    240
tccctgttct ttagcaactt cagcctgctg ggcacccccg tgctcaagga catcaatttc    300
aaaatcgaga ggggccagct gctggccgtg gccggcagca ccggcgccgg aaaaaccagc    360
ctgctgatgg tgatcatggg cgagctcgag cccagcgagg gcaagatcaa gcacagcggc    420
aggatcagct ctgcagcca attcagctgg atcatgcccg gcacaatcaa ggagaacatt     480
atcttcggcg tgagctacga cgagtacaga tacaggtccg tgatcaaggc ctgccagctg    540
gaggaggaca ttagcaagtt cgccgagaag gacaacatcg tactgggcga gggcggcatc    600
accctcagcg gcggccagag agccagaatc agcctggcca gagccgtgta caaggacgcc    660
gacctgtacc tgctggacag ccccttcggc tacctgacg tgctgaccga aggagatc       720 ttcgagagct gcgtgtgcaa gctgatggcc aataagacca ggattctggt gaccagcaag    780
atggagcatc tgaagaaggc cgacaagatc ctgatcctgc acgagggcag cagctacttc    840
tacggcacct tcagcgagct gcagaacctg cagcccgatt tcagcagcaa actgatgggc    900
tgcgacagct tcgatcagtt cagcgccgag aggaggaaca gcatcctgac cgagaccctg    960
cacagattca gcctggaggg cgacgccccc gtgagctgga ccgagaccaa gaagcagagc   1020
ttcaagcaga ccggcgaatt cggcgaaaaa agaaaaaaca gcatcctgaa ccccatcaac   1080
```

-continued

```
agcatcagaa agttctccat cgtgcagaag accccctgc agatgaacgg aattgaggag    1140
gacagcgacg agcccctgga gaggagactg agcctggtgc ccgacagcga gcagggcgag    1200
gccatcctgc ccagaatctc cgtgatctcc accgggccca cctgcaggc ccggcggaga    1260 cagagcgtgc tgaacctgat gacccacagc gtgaatcagg ccagaatat ccatagaaag    1320 accaccgcca gcaccagaaa ggtcagcctg gcccccagg ccaacctgac cgagctggac    1380
atctactcca gcggctgag ccaggaaacc ggcctggaaa tcagcgagga gatcaacgag    1440
gaggacctga aggagtgttt cttcgacgat atggaatcca tccctgccgt taccacctgg    1500
aacacctatc tgagatatat caccgtgcac aaatccctga tcttcgtgct gatctggtgt    1560
ctggtgatct tcctggccga agtggccgcc agcctggtgg tgctgtggct gctgggcaac    1620 accccctgc aggataaggg caatagcacc cacagcagga ataactccta tgccgtgatc    1680
atcacatcta cctcctccta ttacgtgttc tacatctatg tgggcgtggc tgataccctg    1740
ctggccatgg gcttttttcag gggcctgccc ctggtgcaca ccctgatcac cgtgagcaaa    1800
atcctgcacc ataagatgct gcactccgtg ctgcaggctc ccatgcagag gtcgcctctg    1860
gaacctcgaa ccgtcgagga ccccatagta cctcggagac caagtagggc agcctatagt    1920
ttgaagcaga actatttcgg ggggcgagcc ctcatcgtct cttctgcgga tgactcaaca    1980
cgctagggac gtgaagtcga ttccttcgat ggttataaat caaagactca gagtgctgtc    2040
tggagcgtga atctaacggt acgtatctcg attgctcggt cgcttttcgc actccgcgaa    2100
agttcgtacc gctcattcac taggttgcga agcctatgct gatatatgaa tccaaactag    2160
agcagggctc ttaagattcg gagttgtaaa tacttaatac tccaatcggc ttttacgtgc    2220
accaccacgg gcggctgaca agggtctcac atcgagaaac aagagaggtc gcctctggaa    2280
aaggccagcg ttgtctccaa acttttttttc aggtgagaag gtggccaacc gagcttcgga    2340
aagacacgtg cccacgaaag aggagggcgt gtgtatgggt tgggtttggg gtaaaggaat    2400
aagcagtttt taaaaagatg cgctatcatt cattgttttg aaagaaaatg tgggtattgt    2460
agaataaaac agaaagcatt aagaagagat ggaagaatga actgaagctg attgaataga    2520
gagccacatc tacttgcaac tgaaaagtta gaatctcaag actcaagtac gctactatgc    2580
acttgtttta tttcattttt ctaagaaact aaaaatactt gttaataagt acctaagtat    2640
ggtttattgg ttttcccccct tcagcggccg caggaacccc tagtgatgga gttgccact    2700 ccctctctgc gcgctcgctc gctcactgag gccgggcgac caaaggtcgc ccgacgcccg    2760
ggctttgccc gggcggcctc agtgagcgag cgagcgcgca gctgcctgca ggggcgcctg    2820
atgcggtatt ttctccttac gcatctgtgc ggtatttcac accgcatacg tcaaagcaac    2880
catagtacgc gccctgtagc ggcgcattaa gcgcggcggg tgtggtggtt acgcgcagcg    2940
tgaccgctac acttgccagc gccctagcgc ccgctccttt cgctttcttc ccttcctttc    3000
tcgccacgtt cgccggcttt ccccgtcaag ctctaaatcg gggctccct ttagggttcc    3060 gatttagtgc tttacggcac ctcgacccca aaaaacttga tttgggtgat ggttcacgta    3120
gtgggccatc gccctgatag acggttttc gccctttgac gttggagtcc acgttcttta    3180
atagtggact cttgttccaa actggaacaa cactcaaccc tatctcgggc tattcttttg    3240
atttataagg gattttgccg atttcggcct attggttaaa aaatgagctg atttaacaaa    3300
aatttaacgc gaatttttaac aaaatattaa cgtttacaat tttatggtgc actctcagta    3360
caatctgctc tgatgccgca tagttaagcc agccccgaca cccgccaaca cccgctgacg    3420
cgccctgacg ggcttgtctg ctcccggcat ccgcttacag acaagctgtg accgtctccg    3480
```

```
ggagctgcat gtgtcagagg ttttcaccgt catcaccgaa acgcgcgaga cgaaagggcc    3540
tcgtgatacg cctattttta taggttaatg tcatgataat aatggtttct tagacgtcag    3600
gtggcacttt tcggggaaat gtgcgcggaa cccctatttg tttattttt c taaatacatt    3660 caaatatgta tccgctcatg agacaataac cctgataaat gcttcaataa tattgaaaaa    3720
ggaagagtat gagtattcaa catttccgtg tcgcccttat tcccttttt t gcggcatttt    3780 gccttcctgt ttttgctcac ccagaaacgc tggtgaaagt aaaagatgct gaagatcagt    3840
tgggtgcacg agtgggttac atcgaactgg atctcaacag cggtaagatc cttgagagtt    3900
ttcgccccga agaacgtttt ccaatgatga gcacttttaa agttctgcta tgtggcgcgg    3960
tattatcccg tattgacgcc gggcaagagc aactcggtcg ccgcatacac tattctcaga    4020
atgacttggt tgagtactca ccagtcacag aaaagcatct tacggatggc atgacagtaa    4080
gagaattatg cagtgctgcc ataaccatga gtgataacac tgcggccaac ttacttctga    4140
caacgatcgg aggaccgaag gagctaaccg cttttttgca caacatgggg gatcatgtaa    4200
ctcgccttga tcgttgggaa ccggagctga atgaagccat accaaacgac gagcgtgaca    4260
ccacgatgcc tgtagcaatg gcaacaacgt tgcgcaaact attaactggc gaactactta    4320
ctctagcttc ccggcaacaa ttaatagact ggatggaggc ggataaagtt gcaggaccac    4380
ttctgcgctc ggcccttccg gctggctggt ttattgctga taaatctgga gccggtgagc    4440
gtgggtctcg cggtatcatt gcagcactgg ggccagatgg taagccctcc cgtatcgtag    4500
ttatctacac gacggggagt caggcaacta tggatgaacg aaatagacag atcgctgaga    4560
taggtgcctc actgattaag cattggtaac tgtcagacca agtttactca tatatacttt    4620
agattgattt aaaacttcat ttttaattta aaaggatcta ggtgaagatc ctttttgata    4680
atctcatgac caaaatccct taacgtgagt tttcgttcca ctgagcgtca gaccccgtag    4740
aaaagatcaa aggatcttct tgagatcctt ttttt ctgcg cgtaatctgc tgcttgcaaa    4800
caaaaaaacc accgctacca gcggtggttt gtttgccgga tcaagagcta ccaactcttt    4860
ttccgaaggt aactggcttc agcagagcgc agataccaaa tactgtcctt ctagtgtagc    4920
cgtagttagg ccaccacttc aagaactctg tagcaccgcc tacatacctc gctctgctaa    4980
tcctgttacc agtggctgct gccagtggcg ataagtcgtg tcttaccggg ttggactcaa    5040
gacgatagtt accggataag gcgcagcggt cgggctgaac ggggggttcg tgcacacagc    5100
ccagcttgga gcgaacgacc tacaccgaac tgagatacct acagcgtgag ctatgagaaa    5160
gcgccacgct tcccgaaggg agaaaggcgg acaggtatcc ggtaagcggc agggtcggaa    5220
caggagagcg cacgagggag cttccagggg gaaacgcctg gtatctttat agtcctgtcg    5280
ggtttcgcca cctctgactt gagcgtcgat ttttgtgatg ctcgtcaggg gggcggagcc    5340
tatggaaaaa cgccagcaac gcggcctttt tacggttcct ggccttttgc tggccttttg    5400
ctcacatgt                                                           5409
```

<210> SEQ ID NO 16
<211> LENGTH: 7185
<212> TYPE: DNA
<213> ORGANISM: Artificial Sequence
<220> FEATURE:
<223> OTHER INFORMATION: CFTR template vector 2

<400> SEQUENCE: 16

```
cctgaaggag tgtttcttcg acgatatgga atccatccct gccgttacca cctggaacac    60
```

```
ctatctgaga tatatcaccg tgcacaaatc cctgatcttc gtgctgatct ggtgtctggt      120
gatcttcctg gccgaagtgg ccgccagcct ggtggtgctg tggctgctgg gcaacacccc      180
cctgcaggat aagggcaata gcacccacag caggaataac tcctatgccg tgatcatcac      240
atctacctcc tcctattacg tgttctacat ctatgtgggc gtggctgata ccctgctggc      300
catgggcttt tcaggggcc tgcccctggt gcacaccctg atcaccgtga gcaaaatcct      360
gcaccataag atgctgcact ccgtgctgca ggctcccatg agtaccctca ataccctgaa      420
ggccggcggc atcctgaatc gcttctccaa agacatcgcc atcctggacg atctgctgcc      480
actgaccatc ttcgatttca ttcagctgct gctgatcgtg atcggggcca tcgccgtggt      540
ggccgtgctg cagccttaca ttttcgtggc caccgtccct gtgatcgtag ccttcatcat      600
gctgagggcc tacttcctgc agacatccca gcagctgaag caactggaga gcgagggcag      660
atcccccatc tttacccacc tggtgaccag cctgaagggg ctgtggaccc tgagagcctt      720
cgggagacag ccctactttg agaccctctt tcacaaggcc ctgaacctgc acaccgccaa      780
ttggtttctg tacctgagca cccttagatg gttccagatg aggatcgaga tgatcttcgt      840
gatcttcttt atcgccgtga cctttatctc catcctgacc accggcgagg gggaaggcag      900
ggtgggcatc attctgaccc tggccatgaa cataatgagc ccctgcagt gggccgtgaa      960
ctcctccatc gacgtggatt ccctgatgag aagcgtgtcc agggtgttca aatttatcga     1020
catgcccacc gagggcaagc ccaccaagag taccaagccc tataagaacg ccagctgag     1080
caaggtgatg atcatcgaga actcccacgt gaagaaagat gatatttggc ctagcggggg     1140
ccagatgacc gtgaaagatc tgacagccaa gtacaccgag ggcgggaacg ccatcctgga     1200
aaacatctcc ttcagcatct ctcccggaca gagagtgggg ctgctcggca gaacaggctc     1260
cggcaaaagt acactcctga gcgccttcct gaggctgctc aacaccgagg gcgaaatcca     1320
gatcgacggc gtgagctggg acagtatcac actgcagcaa tggaggaaag cctttggagt     1380
gatccccag aaggtgttca tcttttctgg caccttcagg aagaacctgg acccctacga     1440
gcagtggtcc gaccaggaga tctggaaggt ggccgacgaa gtgggcctga ggagcgtgat     1500
cgagcagttc cccggcaagc tcgacttcgt gctggtggac ggcggatgcg tcctgtctca     1560
tggacacaaa cagctgatgt gcctcgcccg ctccgtcctc tccaaggcca agatcctgct     1620
gctcgacgag cccagcgccc acctggaccc cgtgacctac cagatcatca aaggaccct     1680
gaagcaggcc ttcgccgact gcaccgtgat cctgtgcgag cacagaatcg aggccatgct     1740
ggagtgtcag cagttcctgg tgatcgagga gaataaggtg agacagtacg acagcattca     1800
gaagctcctc aatgaaaggt ccctgttcag acaggccatc tctcccagcg atagagtgaa     1860
gctgttcccc cacaggaact cctccaagtg taagagcaag cctcagatcg ccgccctgaa     1920
ggaggagacc gaggaggagg tgcaggacac cagactgtag gccccgctga tcagcctcga     1980
ctgtgccttc tagttgccag ccatctgttg tttgcccctc cccgtgcct tccttgaccc     2040
tggaaggtgc cactcccact gtcctttcct aataaaatga ggaaattgca tcgcattgtc     2100
tgagtaggtg tcattctatt ctggggggtg gggtggggca ggacagcaag ggggaggatt     2160
gggaagacaa tagcaggcat gctgggatg cgtgggcta ctagtgaatt cccacgggt     2220
tggggttgcg ccttttccaa ggcagccctg ggtttgcgca gggacgcggc tgctctgggc     2280
gtggttccgg gaaacgcagc ggcgccgacc ctgggtctcg cacattcttc acgtccgttc     2340
gcagcgtcac ccggatcttc gccgctaccc ttgtgggccc ccggcgacg cttcctgctc     2400
cgcccctaag tcgggaaggt tccttgcggt tcgcggcgtg ccggacgtga caaacggaag     2460
```

```
ccgcacgtct cactagtacc ctcgcagacg gacagcgcca gggagcaatg gcagcgcgcc    2520
gaccgcgatg ggctgtggcc aatagcggct gctcagcggg gcgcgccgag agcagcggcc    2580
gggaaggggc ggtgcgggag gcggggtgtg gggcggtagt gtgggccctg ttcctgcccg    2640
cgcggtgttc cgcattctgc aagcctccgg agcgcacgtc ggcagtcggc tccctcgttg    2700
accgaatcac cgacctctct ccccagatgc cccccccag gctgctgttc ttcctgctgt    2760
tcctgacccc catggaggtg aggcccgagg agccctggt ggtgaaggtg gaggagggcg    2820
acaacgccgt gctgcagtgc ctgaagggca ccagcgacgg ccccacccag cagctgacct    2880
ggagcaggga gagcccctg aagcccttcc tgaagctgag cctgggcctg ccggcctgg    2940 gcatccacat gaggcccctg gccatctggc tgttcatctt caacgtgagc cagcagatgg    3000
gcggcttcta cctgtgccag cccggccccc cagcgagaa ggcctggcag cccggctgga    3060
ccgtgaacgt ggagggcagc ggcgagctgt tcaggtggaa cgtgagcgac ctgggcggcc    3120
tgggctgcgg cctgaagaac aggagcagcg agggccccag cagccccagc ggcaagctga    3180
tgagccccaa gctgtacgtg tgggccaagg acaggcccga gatctgggag ggcgagcccc    3240
cctgcctgcc ccccagggac agcctgaacc agagcctgag ccaggacctg accatggccc    3300
ccggcagcac cctgtggctg agctgcggcg tgcccccgga cagcgtgagc aggggcccc    3360 tgagctggac ccacgtgcac cccaagggcc ccaagagcct gctgagcctg gagctgaagg    3420
acgacaggcc cgccagggac atgtgggtga tggagaccgg cctgctgctg cccagggcca    3480
ccgcccagga cgccggcaag tactactgcc acaggggcaa cctgaccatg agcttccacc    3540
tggagatcac cgccaggccc gtgctgtggc actggctgct gaggaccggc ggctggaagg    3600
tgagcgccgt gaccctggcc tacctgatct tctgcctgtg cagcctggtg ggcatcctgc    3660
acctgcagag ggccctggtg ctgaggagga agaggaagag gatgaccgac cccaccagga    3720
ggttctgata actcgagggc gcgcccgct gatcaacttg tttattgcag cttataatgg    3780
ttacaaataa agcaatagca tcacaaattt cacaaataaa gcatttttt cactgcattc    3840 tagttgtggt ttgtccaaac tcatcaatgt atcagaggtc gcctctggaa cctcgaaccg    3900
tcgaggaccc catagtacct cggagaccaa gtagggcagc ctatagtttg aagcagaact    3960
atttcggggg gcgagccctc atcgtctctt ctgcggatga ctcaacacgc tagggacgtg    4020
aagtcgattc cttcgatggt tataaatcaa agactcagag tgctgtctgg agcgtgaatc    4080
taacggtacg tatctcgatt gctcggtcgc ttttcgcact ccgcgaaagt tcgtaccgct    4140
cattcactag gttgcgaagc ctatgctgat atatgaatcc aaactagagc agggctctta    4200
agattcggag ttgtaaatac ttaatactcc aatcggcttt tacgtgcacc accacgggcg    4260
gctgacaagg gtctcacatc gagaaacaag gcggccgcag gaaccctag tgatggagtt    4320 ggccactccc tctctgcgcg ctcgctcgct cactgaggcc gggcgaccaa aggtcgcccg    4380 acgcccggc tttgcccggg cggcctcagt gagcgagcga gcgcgcagct gcctgcaggg    4440
gcgcctgatg cggtattttc tccttacgca tctgtgcggt atttcacacc gcatacgtca    4500
aagcaaccat agtacgcgcc ctgtagcggc gcattaagcg cggcgggtgt ggtggttacg    4560
cgcagcgtga ccgctacact tgccagcgcc ctagcgcccg ctcctttcgc tttcttccct    4620
tcctttctcg ccacgttcgc cggctttccc cgtcaagctc taaatcgggg gctccctta    4680 gggttccgat ttagtgcttt acggcacctc gaccccaaaa aacttgattt gggtgatggt    4740
tcacgtagtg ggccatcgcc ctgatagacg gttttcgcc ctttgacgtt ggagtccacg    4800
```

```
ttctttaata gtggactctt gttccaaact ggaacaacac tcaaccctat ctcgggctat    4860
tcttttgatt tataagggat tttgccgatt tcggcctatt ggttaaaaaa tgagctgatt    4920
taacaaaaat ttaacgcgaa ttttaacaaa atattaacgt ttacaatttt atggtgcact    4980
ctcagtacaa tctgctctga tgccgcatag ttaagccagc cccgacaccc gccaacaccc    5040
gctgacgcgc cctgacgggc ttgtctgctc ccggcatccg cttacagaca agctgtgacc    5100
gtctccggga gctgcatgtg tcagaggttt tcaccgtcat caccgaaacg cgcgagacga    5160
aagggcctcg tgatacgcct atttttatag gttaatgtca tgataataat ggtttcttag    5220
acgtcaggtg gcacttttcg gggaaatgtg cgcggaaccc ctatttgttt attttttctaa    5280 atacattcaa atatgtatcc gctcatgaga caataaccct gataaatgct tcaataatat    5340
tgaaaaagga gagtatgag tattcaacat ttccgtgtcg cccttattcc cttttttgcg    5400
gcattttgcc ttcctgtttt tgctcaccca gaaacgctgg tgaaagtaaa agatgctgaa    5460
gatcagttgg gtgcacgagt gggttacatc gaactggatc tcaacagcgg taagatcctt    5520
gagagttttc gccccgaaga acgttttcca atgatgagca cttttaaagt tctgctatgt    5580
ggcgcggtat tatcccgtat tgacgccggg caagagcaac tcggtcgccg catacactat    5640
tctcagaatg acttggttga gtactcacca gtcacagaaa agcatcttac ggatggcatg    5700
acagtaagag aattatgcag tgctgccata accatgagtg ataacactgc ggccaactta    5760
cttctgacaa cgatcggagg accgaaggag ctaaccgctt ttttgcacaa catgggggat    5820
catgtaactc gccttgatcg ttgggaaccg gagctgaatg aagccatacc aaacgacgag    5880
cgtgacacca cgatgcctgt agcaatggca acaacgttgc gcaaactatt aactggcgaa    5940
ctacttactc tagcttcccg gcaacaatta atagactgga tggaggcgga taaagttgca    6000
ggaccacttc tgcgctcggc ccttccggct ggctggttta ttgctgataa atctggagcc    6060
ggtgagcgtg ggtctcgcgg tatcattgca gcactggggc cagatggtaa gccctcccgt    6120
atcgtagtta tctacacgac ggggagtcag gcaactatgg atgaacgaaa tagacagatc    6180
gctgagatag gtgcctcact gattaagcat tggtaactgt cagaccaagt ttactcatat    6240
atactttaga ttgatttaaa acttcatttt taatttaaaa ggatctaggt gaagatcctt    6300
tttgataatc tcatgaccaa aatcccttaa cgtgagtttt cgttccactg agcgtcagac    6360
cccgtagaaa agatcaaagg atcttcttga gatcctttt ttctgcgcgt aatctgctgc    6420
ttgcaaacaa aaaaaccacc gctaccagcg gtggtttgtt tgccggatca agagctacca    6480
actctttttc cgaaggtaac tggcttcagc agagcgcaga taccaaatac tgtccttcta    6540
gtgtagccgt agttaggcca ccacttcaag aactctgtag caccgcctac atacctcgct    6600
ctgctaatcc tgttaccagt ggctgctgcc agtggcgata gtcgtgtct taccgggttg    6660 gactcaagac gatagttacc ggataaggcg cagcggtcgg gctgaacggg gggttcgtgc    6720
acacagccca gcttggagcg aacgacctac accgaactga gatacctaca gcgtgagcta    6780
tgagaaagcg ccacgcttcc cgaagggaga aaggcggaca ggtatccggt aagcggcagg    6840
gtcggaacag gagagcgcac gagggagctt ccagggggaa acgcctggta tctttatagt    6900
cctgtcgggt ttcgccacct ctgacttgag cgtcgatttt tgtgatgctc gtcaggggg    6960 cggagcctat ggaaaaacgc cagcaacgcg gcctttttac ggttcctggc cttttgctgg    7020
ccttttgctc acatgtcctg caggcagctg cgcgctcgct cgctcactga ggccgcccgg    7080
gcaaagcccg ggcgtcgggc gacctttggt cgcccgcct cagtgagcga gcgagcgcgc    7140
agagagggag tggccaactc catcactagg ggttccggcg gccgc    7185
```

<210> SEQ ID NO 17
<211> LENGTH: 23
<212> TYPE: DNA
<213> ORGANISM: Artificial Sequence
<220> FEATURE:
<223> OTHER INFORMATION: synthetic polymer

<400> SEQUENCE: 17
cccttctggg ctcactatgc tgc                                              23

<210> SEQ ID NO 18
<211> LENGTH: 18
<212> TYPE: DNA
<213> ORGANISM: Artificial Sequence
<220> FEATURE:
<223> OTHER INFORMATION: synthetic polymer

<400> SEQUENCE: 18
gggggcccca tgttcgcc                                                    18

<210> SEQ ID NO 19
<211> LENGTH: 40
<212> TYPE: DNA
<213> ORGANISM: Artificial Sequence
<220> FEATURE:
<223> OTHER INFORMATION: synthetic polymer

<400> SEQUENCE: 19
cccttcgggg gcccttctgg gctcactatg ctgctgggct                            40

<210> SEQ ID NO 20
<211> LENGTH: 35
<212> TYPE: DNA
<213> ORGANISM: Artificial Sequence
<220> FEATURE:
<223> OTHER INFORMATION: synthetic polymer

<400> SEQUENCE: 20
gggggcccta tgttcgcctg gctcactat gctgc                                  35

<210> SEQ ID NO 21
<211> LENGTH: 286
<212> TYPE: PRT
<213> ORGANISM: Artificial Sequence
<220> FEATURE:
<223> OTHER INFORMATION: synthetic polymer

<400> SEQUENCE: 21

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
                100                 105                 110

```
Asp Gly Met Thr Val Arg Glu Leu Cys Ser Ala Ala Ile Thr Met Ser
            115                 120                 125
Asp Asn Thr Ala Ala Asn Leu Leu Thr Thr Ile Gly Gly Pro Lys
        130                 135                 140
Glu Leu Thr Ala Phe Leu His Asn Met Gly Asp His Val Thr Arg Leu
145                 150                 155                 160
Asp Arg Trp Glu Pro Glu Leu Asn Glu Ala Ile Pro Asn Asp Glu Arg
                165                 170                 175
Asp Thr Thr Met Pro Val Ala Met Ala Thr Thr Leu Arg Lys Leu Leu
            180                 185                 190
Thr Gly Glu Leu Leu Thr Leu Ala Ser Arg Gln Gln Leu Ile Asp Trp
        195                 200                 205
Met Glu Ala Asp Lys Val Ala Gly Pro Leu Leu Arg Ser Ala Leu Pro
    210                 215                 220
Ala Gly Trp Phe Ile Ala Asp Lys Ser Gly Ala Gly Glu Arg Gly Ser
225                 230                 235                 240
Arg Gly Ile Ile Ala Ala Leu Gly Pro Asp Gly Lys Pro Ser Arg Ile
                245                 250                 255
Val Val Ile Tyr Thr Thr Gly Ser Gln Ala Thr Met Asp Glu Arg Asn
            260                 265                 270
Arg Gln Ile Ala Glu Ile Gly Ala Ser Leu Ile Lys His Trp
        275                 280                 285

<210> SEQ ID NO 22
<211> LENGTH: 333
<212> TYPE: PRT
<213> ORGANISM: Artificial Sequence
<220> FEATURE:
<223> OTHER INFORMATION: synthetic polymer

<400> SEQUENCE: 22

Met Pro Pro Pro Arg Leu Leu Phe Phe Leu Leu Phe Leu Thr Pro Met
1               5                   10                  15
Glu Val Arg Pro Glu Glu Pro Leu Val Val Lys Val Glu Glu Gly Asp
            20                  25                  30
Asn Ala Val Leu Gln Cys Leu Lys Gly Thr Ser Asp Gly Pro Thr Gln
        35                  40                  45
Gln Leu Thr Trp Ser Arg Glu Ser Pro Leu Lys Pro Phe Leu Lys Leu
    50                  55                  60
Ser Leu Gly Leu Pro Gly Leu Gly Ile His Met Arg Pro Leu Ala Ile
65                  70                  75                  80
Trp Leu Phe Ile Phe Asn Val Ser Gln Gln Met Gly Gly Phe Tyr Leu
                85                  90                  95
Cys Gln Pro Gly Pro Pro Ser Glu Lys Ala Trp Gln Pro Gly Trp Thr
            100                 105                 110
Val Asn Val Glu Gly Ser Gly Glu Leu Phe Arg Trp Asn Val Ser Asp
        115                 120                 125
Leu Gly Gly Leu Gly Cys Gly Leu Lys Asn Arg Ser Ser Glu Gly Pro
    130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                165                 170                 175
Arg Asp Ser Leu Asn Gln Ser Leu Ser Gln Asp Leu Thr Met Ala Pro
            180                 185                 190
```

```
Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                    325                 330
```

<210> SEQ ID NO 23
<211> LENGTH: 286
<212> TYPE: PRT
<213> ORGANISM: Artificial Sequence
<220> FEATURE:
<223> OTHER INFORMATION: synthetic polymer

<400> SEQUENCE: 23

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
210                 215                 220
```

```
Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```